United States Patent
Barnea

(10) Patent No.: US 11,096,987 B2
(45) Date of Patent: *Aug. 24, 2021

(54) MUTANT PEPTIDES AND METHODS OF TREATING SUBJECTS USING THE SAME

(71) Applicant: BIOINCEPT, LLC, Cherry Hill, NJ (US)

(72) Inventor: Eytan R. Barnea, Cherry Hill, NJ (US)

(73) Assignee: BIOINCEPT, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/756,454

(22) PCT Filed: Mar. 16, 2016

(86) PCT No.: PCT/US2016/022725
§ 371 (c)(1),
(2) Date: Feb. 28, 2018

(87) PCT Pub. No.: WO2017/039751
PCT Pub. Date: Mar. 9, 2017

(65) Prior Publication Data
US 2019/0022181 A1    Jan. 24, 2019

Related U.S. Application Data

(63) Continuation of application No. PCT/US2015/050532, filed on Sep. 16, 2015, and a continuation of application No. PCT/US2015/058877, filed on Nov. 3, 2015.

(60) Provisional application No. 62/211,660, filed on Aug. 28, 2015.

(51) Int. Cl.
| | |
|---|---|
| A61K 38/17 | (2006.01) |
| A61P 37/00 | (2006.01) |
| A61P 31/00 | (2006.01) |
| A61K 9/00 | (2006.01) |
| A61K 38/10 | (2006.01) |
| A61P 3/10 | (2006.01) |
| A61K 45/06 | (2006.01) |
| A61P 7/00 | (2006.01) |
| A61P 25/00 | (2006.01) |
| A61P 37/02 | (2006.01) |
| A61P 31/06 | (2006.01) |
| A61P 9/10 | (2006.01) |

(52) U.S. Cl.
CPC ........ *A61K 38/1709* (2013.01); *A61K 9/0019* (2013.01); *A61K 38/10* (2013.01); *A61K 45/06* (2013.01); *A61P 3/10* (2018.01); *A61P 7/00* (2018.01); *A61P 9/10* (2018.01); *A61P 25/00* (2018.01); *A61P 31/00* (2018.01); *A61P 31/06* (2018.01); *A61P 37/00* (2018.01); *A61P 37/02* (2018.01); *A61K 2300/00* (2013.01); *Y02A 50/30* (2018.01)

(58) Field of Classification Search
CPC .. A61K 38/1709; A61K 45/06; A61K 9/0019; A61K 38/10; A61K 2300/00; A61P 7/00; A61P 25/00; A61P 37/02; A61P 31/06; A61P 9/10; A61P 3/10; A61P 37/00; A61P 31/00; Y02A 50/401; Y02A 50/411
See application file for complete search history.

(56) References Cited

U.S. PATENT DOCUMENTS

| | | |
|---|---|---|
| 4,629,722 A | 12/1986 | Ribi |
| 5,279,941 A | 1/1994 | Lessey |
| 5,393,534 A | 2/1995 | Cavanaugh et al. |
| 5,645,829 A | 7/1997 | Shockley et al. |
| 5,646,003 A | 7/1997 | Barnea |
| 5,648,340 A | 7/1997 | Barnea |
| 5,658,792 A | 8/1997 | Nuell et al. |
| 5,665,355 A | 9/1997 | Primi |
| 5,981,198 A | 11/1999 | Barnea et al. |
| 6,171,591 B1 | 1/2001 | Hall |
| 6,225,097 B1 | 5/2001 | Obata et al. |
| 6,365,727 B1 | 4/2002 | Yoon et al. |
| 6,585,979 B1 | 7/2003 | Berman |
| 7,273,708 B2 | 9/2007 | Barnea et al. |
| 7,670,850 B2 | 3/2010 | Barnea et al. |
| 7,670,851 B2 | 3/2010 | Barnea et al. |
| 7,670,852 B2 | 3/2010 | Barnea et al. |
| 7,678,582 B2 | 3/2010 | Barnea et al. |
| 7,695,977 B2 | 4/2010 | Barnea et al. |
| 7,723,289 B2 * | 5/2010 | Barnea ............... A61K 49/0002 424/184.1 |

(Continued)

FOREIGN PATENT DOCUMENTS

| | | |
|---|---|---|
| CA | 2490538 A1 | 1/2003 |
| DE | 4400640 A1 | 7/1995 |

(Continued)

OTHER PUBLICATIONS

Reeck et al, "Homology" in proteins and nucleic acids: a terminology muddle and a way out of it, Cell, 1987, 50, p. 667.*

(Continued)

*Primary Examiner* — Li N Komatsu
(74) *Attorney, Agent, or Firm* — Ballard Spahr LLP

(57) ABSTRACT

The disclosure relates to a pharmaceutical composition comprising any one or combination of PIF peptides or analogs or pharmaceutically acceptable salts thereof. Methods of treating autoimmune disease using the one or a combination of PIF peptide or analogs thereof or pharmaceutically acceptable salts thereof is also disclosed.

24 Claims, 30 Drawing Sheets
Specification includes a Sequence Listing.

(56) References Cited

U.S. PATENT DOCUMENTS

| | | | |
|---|---|---|---|
| 7,723,290 B2 | 5/2010 | Barnea | |
| 8,222,211 B2 | 7/2012 | Barnea | |
| 8,454,967 B2 | 6/2013 | Barnea | |
| 9,097,725 B2 | 8/2015 | Barnea | |
| 9,737,585 B2 | 8/2017 | Barnea | |
| 10,071,131 B2 | 9/2018 | Barnea | |
| 2002/0004205 A1 | 1/2002 | Consler et al. | |
| 2003/0099643 A1 | 5/2003 | June et al. | |
| 2003/0109690 A1 | 6/2003 | Ruben et al. | |
| 2003/0203410 A1 | 10/2003 | Barnea et al. | |
| 2003/0228256 A1 | 12/2003 | Inverardi et al. | |
| 2005/0003397 A1 | 1/2005 | Hardy et al. | |
| 2005/0064520 A1 | 3/2005 | Barnea et al. | |
| 2007/0136003 A1 | 6/2007 | Choi et al. | |
| 2007/0231310 A1 | 10/2007 | Friedlander et al. | |
| 2008/0003178 A1* | 1/2008 | Barnea | A61K 49/0002 424/1.69 |
| 2008/0227778 A1 | 9/2008 | Dinsmore et al. | |
| 2008/0269137 A1 | 10/2008 | Barnea | |
| 2008/0293149 A1 | 11/2008 | Barnea et al. | |
| 2008/0299677 A1 | 12/2008 | Barnea et al. | |
| 2008/0305468 A1 | 12/2008 | Barnea et al. | |
| 2008/0305552 A1 | 12/2008 | Barnea et al. | |
| 2009/0011427 A1 | 1/2009 | Barnea et al. | |
| 2009/0081225 A1 | 3/2009 | Barnea | |
| 2010/0004430 A1 | 1/2010 | Nilsson et al. | |
| 2010/0197040 A1 | 8/2010 | Barnea et al. | |
| 2011/0033539 A1 | 2/2011 | Quart et al. | |
| 2011/0070184 A1 | 3/2011 | Bernhagen et al. | |
| 2011/0112016 A1 | 5/2011 | Barnea | |
| 2012/0107318 A9 | 5/2012 | Barnea | |
| 2012/0301921 A1 | 11/2012 | Williams et al. | |
| 2013/0058943 A1 | 3/2013 | Fox et al. | |
| 2014/0004545 A1 | 1/2014 | Barnea | |
| 2014/0147414 A1 | 5/2014 | Barnea | |
| 2014/0271652 A1 | 9/2014 | Scoville | |
| 2015/0125886 A9 | 5/2015 | Barnea | |
| 2015/0232418 A1 | 8/2015 | Schlechtingen et al. | |
| 2016/0263186 A1 | 9/2016 | Barnea | |
| 2017/0080047 A1 | 3/2017 | Barnea | |
| 2017/0319645 A1 | 11/2017 | Barnea | |
| 2018/0021401 A1 | 1/2018 | Barnea | |
| 2019/0022181 A1 | 1/2019 | Barnea | |
| 2019/0054139 A1 | 2/2019 | Barnea | |
| 2020/0000874 A1 | 1/2020 | Barnea | |

FOREIGN PATENT DOCUMENTS

| | | |
|---|---|---|
| EP | 1404877 A2 | 4/2004 |
| JP | 2014-508164 A | 4/2014 |
| WO | WO-92/09294 A1 | 6/1992 |
| WO | WO-94/06464 A1 | 3/1994 |
| WO | WO-95/26982 A2 | 10/1995 |
| WO | WO-97/09418 A1 | 3/1997 |
| WO | WO-98/52550 A1 | 11/1998 |
| WO | WO-00/01402 A1 | 1/2000 |
| WO | WO-00/43789 A1 | 7/2000 |
| WO | WO-00/063675 A1 | 10/2000 |
| WO | WO-02/40717 A2 | 5/2002 |
| WO | WO-02/053092 A2 | 7/2002 |
| WO | WO-03/004601 A2 | 1/2003 |
| WO | WO-03/033644 A2 | 4/2003 |
| WO | WO-2004/053086 A2 | 6/2004 |
| WO | WO-2005/030791 A2 | 4/2005 |
| WO | WO-2005/040196 A2 | 5/2005 |
| WO | WO-2006/113898 A2 | 10/2006 |
| WO | WO-2007/131218 A2 | 11/2007 |
| WO | WO-2012/119072 A2 | 9/2012 |
| WO | WO-2014/201118 A2 | 12/2014 |
| WO | WO-2015/040196 A2 | 3/2015 |
| WO | WO-2015/061483 A2 | 4/2015 |
| WO | WO-2016/030901 A1 | 3/2016 |
| WO | WO-2016/073513 A1 | 5/2016 |
| WO | WO-2017/079430 A1 | 5/2017 |

OTHER PUBLICATIONS

Pearson, An Introduction to Sequence Similarity ("Homology") Searching, Current Protocols in Bioinformatics, 2013, pp. 3.1.1-3.1.8.*

Afkhami, F., et al., Investigation of antiangiogenic tumor therapy potential of microencapsulated HEK293 VEGF165b producing cells, J. Biomedicine and Biotechnology, 2010, 2010:645610, 7 pages.

Barnea, E. R., et al., Identification and validation of an assay for preimplantation factor (PIF), The Second World Conference on Implantation and Early Pregnancy in Humans, May 12-14, 1994, Atlantic City, NJ (Abstract).

Barnea, E. R., et al., The role of pre-implantation factor (PIF) in the immune recognition of pregnancy, The Second International Congress on Autoimmunity, Mar. 7-12, 1999, Tel Aviv, Israel (Abstract).

Chen, Y. C., et al., PreImplantation factor prevents atherosclerosis via its immunomodulatory effects without affecting serum lipids, Thromb. Haemost., 2016,115(5):1010-24, Abstract only.

Gurudutta, G. U., et al., Stem cell therapy: A novel & futuristic treatment modality for disaster injuries, Indian J. Med. Res., 2012,135:15-25.

Hayrabedyan, S. B., et al., Structural design-based preimplantation factor (PIF*) fusion peptide synthetic DNA cloning and eukaryote expression aimed for functional proteomic studies and possible chronic immune disorders therapy, J. Reproductive Immunology, 2014, 101-102:60.

Azar, Y., et al. "Preimplantation Factor Reduces Graft-Versus-Host Disease by Regulating Immune Response and Lowering Oxidative Stress (Murine Model)," Biol. Blood Marrow Transplant, 2013, vol. 19, No. 4, pp. 519-528.

Barnea, E., "Embryo Maternal Dialogue: From Pregnancy Recognition to Proliferation Control," Early Pregnancy, vol. 2001, vol. V, No. 1, pp. 65-66.

Barnea, E. R et al., "Preimplantation Factor (PIF) Orchestrates Systemic Antiinflammatory Response by Immune Cells: Effect on Peripheral Blood Mononuclear Cells," Am. J. Obstet. Gynecol., 2012; vol. 207, No. 4, p. 313.e1-11.

Bhattacharya, R., et al., "Impact of Genetic Variation on Three Dimensional Structure and Function of Proteins," PLOS ONE, 2017,12(3): e0171355, pp. 1-22.

Paidas, M. "Treatment of Acute Radiation Syndrome Using PIF, a Natural Immune Modulator," BioIncept, LLC, Project No. 1R41AI120546-01, Jun. 10, 2015, Retrieved from the Internet: https://projectreporter.nih.gov/project/info_description.cfm?projectnumber =1R41AI120546-01 on Nov. 18, 2015.

Roussev, R. G., et al., "Preimplantation Factor Inhibits Circulating Natural Killer Cell Cytotoxicity and Reduces CD69 Expression: Implications for Recurrent Pregnancy Loss Therapy," Reproductive BioMedicine Online, 2013, vol. 26, No. 1, pp. 79-87.

Shainer, R., et al. "Immune Regulation and Oxidative Street Reduction by Preimplantation Factor Following Syngeneic or Allogeneic Bone Marrow Transplantation," Conference Papers in Medicine, 2013, vol. 22, No. 1, 8 pages.

Shainer, R., et al. "PB-277: Pre-Implantation Factor (PIF) as Prophylaxis after Radiation Exposure: Immune-Regulation and iNOS Reduced Expression," Poster presented in The 7th Congress of the Federation of the Israel Societies for Experimental Biology, Feb. 10-13, 2014.

Tokuriki, N., et al., "Stability Effects of Mutations and Protein Evolvability," Current Opinion in Structural Biology, 2009, vol. 19, pp. 596-604.

Weiss. L., et al., "Preimplantation Factor (PIF) Analog Prevents Type I Diabetes Mellitus (TIDM) Development by Preserving Pancreatic Function in NOD Mice," Endocrine, 2011, vol. 40, pp. 42-54.

International Search Report for PCT/US2016/022725 dated Sep. 30, 2016 (5 pages).

International Preliminary Report on Patentability for PCT/US2016/022725 dated Mar. 6, 2018 (10 pages).

International Search Report for PCT/US2015/058877 dated Apr. 13, 2016 (8 pages).

(56) References Cited

OTHER PUBLICATIONS

International Preliminary Report on Patentability for PCT/US2015/058877 dated May 9, 2017 (20 pages).
International Search Report for PCT/US2015/050532 dated Dec. 22, 2015 (4 pages).
International Preliminary Report on Patentability for PCT/US2015/050532 dated Mar. 21, 2017 (9 pages).
Abbas, A. K., et al., Functional diversity of helper T lymphocytes, Nature, 1996, 383(6603):787-793.
Ancsin, J. B., et al., A binding site for highly sulfated heparan sulfate is identified in the N terminus of the circumsporozoite protein: significance for malarial sporozoite attachment to hepatocytes, J. Biol. Chern., 2004, 279(21):21824-21832.
Aplin, J. D., et al., Trophoblast-uterine interactions at implantation, Reprod. Biol, and Endocrinol., 2004, 2:48,12 pages.
Asai, K., et al., Dexamthasone-induced suppression of aortic atherosclerosis in cholesterol fed rabbits—possible mechanisms, Arterosclerol. Thrombos., 1993,13:892-899.
Asano, M., et al., Autoimmune Disease as a Consequence of Developmental Abnormality of a T Cell Subpopulation, J. Exp. Med., 1996,184(2):387-396.
Atkinson, M. A., et al., The NOD mouse model of type 1 diabetes. As good as it gets?, Nat. Med., 1999, 5(6):601-604.
Azar, Y., et al., Preimplantation Factor Reduces Graft-Versus-Host Disease by Regulating Immune Response and Lowering Oxidative Stress (Murine Model), Biol. Blood Marrow Transplant, 2013, 19(4):519-528.
Bainbridge, D., et al., HLA-G remains a mystery, Trends Immunol., 2001,22(10):548-552.
Banker, G. S., et al., Eds., Modern Pharmaceutics, Marcel Dekker, Inc., New York, 1979, TOC only.
Barnea, E. R., et al., Human embryo regulates placental function in first trimester, International Congress of Endocrinology, Kyoto, Japan, 1988, (Abstract).
Barnea, E. R., et al., Human embryonal extracts modulate placental function in the first trimester: effects of visceral tissues upon chorionic gonadotropin and progesterone secretion, Placenta, 1989, 10(4):331-344. .
Barnea, E. R., et al., Endocrinology of the placental and embryo-placental interaction, in Barnea, E. R., et al., Eds., The First Twelve Weeks of Gestation, Berlin: Springer-Verlag, 1992, pp. 128-153.
Barnea, E. R., et al., Epilogue, in Barnea, E. R., et al., Eds., The First Twelve Weeks of Gestation, Berlin: Springer-Verlag, 1992, pp. pp. 542-548.
Barnea, E. R., et al., Eds., The First Twelve Weeks of Gestation, Berlin: Springer-Verlag, 1992, Forward and TOC only.
Barnea, E. R., et al., Use of lymphocyte platelet binding assay for detecting a preimplantation factor: A quantitative assay, Am. J. Reprod. Immunol., 1994, 32:133-138.
Barnea, E. R., Dual effects of embryo-derived factors on hCG secretion by placental explants, in Barnea, E. R., et al., Eds., Implantation and Early Pregnancy in Humans, Camforth: Parthenon Publishing, 1994, pp. 271-282.
Barnea, E. R., et al., Identification and validation of an assay for preimplantation (PIF), The Second World Conference on Implantation and Early Pregnancy in Humans, May 12-14, 1994, (Abstract).
Barnea, E. R., New Frontiers in Early Pregnancy Investigation, Early Pregnancy, Biol. & Med., 1995,1:1-3.
Barnea, E. A., EnVision the Field of Early Pregnancy Investigation, Early Pregnancy, Biol. & Med., 1995, 1:169-170.
Barnea, E. R., et al., Reflections on early pregnancy: organizing chaos or organized chaos?, (Editorial) Early Pregnancy: Biol. & Med., 1996, 2:77-79.
Barnea, E. R., et al., Control of cell proliferation by embryonal-origin factors, Am. J. Reprod.
Immunol., 1996, 35(4):318-324.
Barnea, E. R., et al., New perspectives on prevention of environmentally-induced damage to the embryo, Reproduction - Humaines et Hormones, 1996, 7:423-428. Summary only.

Barnea, E. R., et al., Preimplantation factor (PIF): current developments, Third World Conference on Early Pregnancy - An Interdisciplinary Approach, Atlantic City, NJ, Oct. 3-6, 1996, (Abstract).
Barnea, E. R., et al., Preimplantation signalling by the embryo, The 3r World Conference on Early Pregnancy, Oct. 3-6, 1996, (Abstract).
Barnea, E. R., et al., Partial characterization of embryo-derived preimplantation factor (PIF), IXth World Congress on Human Reproduction, Philadelphia, PA, May 28-Jun. 2, 1996, (Abstract).
Barnea, E. R., et al., Embryonic signals, in Embryonic Medicine and Therapy, Jauniaux, E., et al., Eds., 1997, Oxford: Oxford University Press, pp. 63-75.
Barnea, E. R., The Embryo: a privileged entity in a privileged site: Lessons learnt from embryonal development, (Editorial) Early Pregnancy: Biol. & Med., 1997, 3:77-80.
Barnea, E. R., et al., The Embryo-Trophoblast Paradox, Embryonic Medicine and Therapy, Oxford University Press, 1997,15:256-279.
Barnea, E. R., et al., Partial characterization of mammalian preimplantation factor (PIF) in culture and in vivo, Fourth International Meeting of Alps Adria Society for Immunology of Reproduction (AASIR), Sep. 1998, Opatija, Croatia (abstract).
Barnea, E. R., et al., Progress in characterization of pre-implantation factor in embryo cultures and in vivo, Am. J. Reprod. Immunol., 1999, 42(2):95-99.
Barnea, E. R., et al., Maternal Immune Response to Trophoblast, GTD, and Cancer, in The Decade of Autoimmunity, Shoenfeld Y., Ed., Elsevier Science B.V. Publishers, 1999, pp. 309-316.
Barnea, E. R., Preimplantation Factor: A specific embryo viability factor, The First National Congress on Human Assisted Reproduction with International Participation under the ;ti patronage of the Romanian Academy, Timisoara, Romania, May 27-29, 1999, (Abstract).
Barnea, E. R., Current progress in Early Pregnancy investigation and the steps ahead, (Editorial) Early Pregnancy Biology & Medicine, 2QOQ, IV(1):1-4.
Barnea, E. R., et al., Pregnancy derived compounds that control proliferation, Cancer and Pregnancy, 2000, 22:275-284.
Barnea, E. R., et al., Maternal Immune Response to Trophoblast, GTD and Cancer, In: Cancer and Autoimmunity, Shoenfeld, Y. and Gerhwin, M.E ,eds., Elsevier Science BV Publishers, 2000, pp. 343-350.
Barnea, E. R., Embryo-Maternal dialogue: Linking pregnancy recognition and proliferation control, 4th World Conference on Early Pregnancy, under the auspices of the Hungarian Society of Obstetrics and Gynecology and SIEP, the Society for the Investigation of Early Pregnancy, Pecs, Hungary, Jun. 1-3, 2000, (Abstract).
Barnea, E. R., Embryo-maternal dialogue: from pregnancy recognition to proliferation control, 14th Rochester Trophoblast Conference, by Trophoblast Conference and SIEP, Rochester, NY, Oct. 4-8, 2000, (Abstract).
Barnea, E., Embryo Maternal Dialogue: From Pregnancy Recognition to Proliferation Control, Early Pregnancy, 2001, V(1):65-66.
Barnea, E. R., et al., Immune System (IS) and Proliferation Control (PC) from Embryo to Adulthood: Roles of Preimplantation Factor (PIE) and of Developmental Proteins (DPs), from Renaissance Congress of 21 .sup.st Century: The Woman and Child Before, During and After Pregnancy, Cosmi ed., Monduzzi Editore, Rome, Italy, May 22-26, 2001, pp. 93-102.
Barnea, E. R., et al., Embryo-maternal signaling prior to implantation, Textbook of Obstetrics & Gynecology, Siep, Bbri, 2001, 2:112-117.
Barnea, E. R., et al., From embryo-trophoblastic to feto-placental unit, Implantation in Obstetrics and Gynecology, Section 2 Human Reproduction-Anatomy, Physiology, Embryology, Munteanu, 1., Ed., Romanian Academy of Science Publishers, 2001, TOC and pp. 117-123.
Barnea, E. R., et al., Evolution of Feto-Placental Unit, Textbook of Obstetrics & Gynecology, Siep, Bbri, 2001,2:170-175.
Barnea, E. R., Safeguards established at conception influence pen and postnatal life: Roles of Preimplantation Factor (PIF) and Developmental Proteins (DPs), World Congress of Perinatal Medicine, Parallel Scientific SIEP Meeting, Barcelona, Spain, Sep. 23-27, 2001, (Abstract).

(56) References Cited

OTHER PUBLICATIONS

Barnea, E. R., Underlying mechanisms and treatment of early pregnancy failure, Ferti Magazine (Ferti.Net <http://Ferti.Net> Worldwide Fertility Network), 2001,4 pp.

Barnea, E. R., Novel Preimplantation Factors (PIF) and Developmental Peptides (DPs) are involved in safeguarding pregnancy, The Fetus as a Patient, Budapest, Hungary, 2002, (Abstract).

Barnea, E. R., Critical Elements for Early Development and Beyond: Immune Tolerance (PIF) and Proliferation Control (DPs), Sixth World Conference of Early Pregnancy: Workshop on Embryology Early Pregnancy Investigation, Organized by SIEP, supported by Rotunda the Center for Human Reproduction and Mangeshikar Center for Gynaelogical Endoscopic Surgery, Jodphur, India, 2002, (Abstract).

Barnea, E. R., et al., Immune Modulation, by Embryo-Specific Peptides, Allow for Embryo Tolerance whilst Preserving the Maternal Host's Ability to Fight Pathogens: Preimplantation Factor (PIF), First Brown-Linkoping Meeting on Basic and clinical Aspects of Reproductive Immunology, Providence, RI, Nov. 15, 2002, (Abstract).

Barnea, E. R., Maternal Immune Recognition of Pregnancy is Initiated by Novel Embryo-Derived Preimplantation Factor (PIF). Invited Speaker. Hippokration Congress on Reproductive Immunology (4th Esradi C) European Society for Reproductive and Developmental Immunology, Rhodes, Greece, 2003, pp. 123-124 (Abstract 1.32); also pub. in J. Reprod. Immun. pp. 23-24, (Abstract).

Barnea, E. R., et al., Prediction of Implantation in ART using Molecular Biology, Assisted Reproductive Technology, 2004, pp. 183-194.

Barnea, E. R., Insight into early pregnancy events: the emerging role of the embryo, Am. J. Reprod. Immunol., 2004, 51:319-322.

Barnea, E. R., et al., Embryo-derived Preimplantation Factor (PIF*): Methods to assess embryo viability towards successful pregnancy, 5th Indian Congress of Gynecologic Endoscopy and ART and SIEP, Khajuraho, India, Nov. 2004, (Abstract).

Barnea, E. R., et al., Preimplantation Factor (PIF): Relevance for Human Pregnancy, 24th Ann. Mtg. of the American Society for Reproductive Immunology, St. Louis, MO, 2004, (Abstract).

Barnea, E. R., et al., Expression of Novel Immunomodulators (PIF*) and Proliferation Controllers (DPs) by the Embryo and by the Placenta, Invited Speaker at the 32nd Conference of the European Teratology Society, Thessaloniki, Greece, Sep. 19-22, 2004, Reproductive Toxicology, 2004,18:707-756 (Abstract at p. 715).

Barnea, E. R., et al., Preimplantation Factor (PIF): Novel Immunomodulatory Peptide and Expression by Gestational Tissues, The 12th International Federation of Placenta Association (IFPA), Kobe, Japan, Sep. 6-9, 2006, (Abstract).

Barnea, E. R., et al., Novel Embryo-Derived Preimplantation Factor (PIF): An Immune-Modulatory Therapy Approach for Immune Disorders, 5th International Congress on Autoimmunity, Sorrento, Italy, 2006, (Abstract).

Barnea, E. R., et al., Preimplantation Factor PIF: From Embryo Tolerance to Embryo Viability Detection and Treatment of Autoimmune Diseases, Eleventh International Symposium.

For Immunology of Reproduction. (ISIR) International House of Scientists, Varna, Bulgaria, 2006, (Abstract).

Barnea, E. R., Signaling Between Embryo and Mother in Early Pregnancy: Basis for Development of Tolerance, in Recurrent Pregnancy Loss Causes, Controversies and Treatment. Carp, H. J. A., Ed., Series in Maternal-Fetal Medicine, Informa Healthcare, Taylor and Francis Group publ., 2007, 2:15-22.

Barnea, E. R., Applying embryo-derived immune tolerance to the treatment of immune disorders, Ann. N. Y. Acad. Sci., 2007, 1110: 602-618.

Barnea, E. R., Apply Embryo Derived Tolerance for Managing Reproductive and Immune Disorders: Preimplantation Factor (PIF), 27th Annual Meeting of the American Society for Reproductive Immunology, Toronto, Canada, 2007, (Abstract).

Barnea, E. R., From PIF identification to clinical applications: Immunomodulatory Embryo-Derived Novel Peptide: True BioMarker Dx and Nontoxic Rx Application, Mining the Plasma Proteone Meeting, Success Stories Session, PepTalk Conf., CHI Cambridge Healthtech Institute, Coronado, San Diego CA, Jan. 7-9, 2008, (Abstract).

Barnea, E. R et al., Preimplantation Factor (PIF) Orchestrates Systemic Antiinflammatory Response by Immune Cells: Effect on Peripheral Blood Mononuclear Cells, Am. J. Obstet. Gynecol., 2012; 207(4):313.e1-11. .

Basu, U et al., Translational Regulation of Utrophin by miRNAs, Plos One, 2011, 6(12): e29376, 9 pages.

Bates, M. D., et al., Aberrant cytokine production by peripheral blood mononuclear cells in recurrent pregnancy loss?, Hum. Reprod., 2002,17(9):2439-2444.

Battye, K. M., et al., Production of platelet-activating factor by the pre-implantation sheep embryo, J. Reprod. Fertil., 1991, 93:507-514.

Beausoleil, S. A., et al., Large-scale characterization of HeLa cell nuclear phosphoproteins, Proc. Natl. Acad. Sci. USA, 2004,101(33):12130-12135.

Bell, J. J., et al., In Trans T Cell Tolerance Diminishes Autoantibody Responses and Exacerbates Experimental Allergic Encephalomyelitis, J. Immunology, 2008,180:1508-1516.

Bhattacharya, R., et al., Impact of Genetic Variation on Three Dimensional Structure and Function of Proteins, Plos One, 2017,12(3):e0171355, 22 pages.

Bodian, D. L., et al., Crystal structure of the extracellular region of the human cell adhesion molecule CD2 at 2.5 A resolution, Structure, 1994, 2(8):755-766.

Boklage, C. E., Survival probability of human conceptions from fertilization to term, Int. J. Fertil., 1990, 35(2):75, 79-80, 81-94, Abstract only.

Bose, R., etaL, Purified human early pregnancy factor from preimplantation embryo possesses immunosuppressive properties, Am. J. Obstet. Gynecol,, 1989,160(4):954-960, Abstract only.

Bose, R., Properties of human pre- and post-implantation embryo-associated immunosuppressor factors), Immunol. Letters, 1991, 30(3):325-332.

Bresson, D., et al., Mechanisms underlying type I diabetes, Drug Discovery Today: Disease Mechanisms, 2004,1(3):321-327.

Bringer, R., et al., PIF-1 Improves Graft vs. Host Disease (GVHD) while maintaining Graft vs. Leukemia (GVL) effect after bone marrow transplantation in mice, The 5th Annual Congress of the Federation of the Israel Societies for Experimental Biology, Eilat, Israel, Jan. 28-31, 2008, (Abstract).

Burgess, W. H., et al., Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue, J. Cell Biol., 1990,111(5 Pt 1):2129-2138.

Burt, R. K., et al., Hematopoietic stem cell transplantation for progressive multiple sclerosis:.

Failure of a total body irradiation-based conditioning regimen to prevent disease progression in patients with high disability scores, Blood, 2003, 102(7):2373-2378.

Cavanagh, A. C., et al., The purification of early-pregnancy factor to homogeneity from human platelets and identification as chaperonin 10, Eur. J. Biochem., 1994,222(2):551-560.

Chakrabarti, L., et al., Sequence of simian immunodeficiency virus from macaque and its relationship to other human and simian retroviruses, Nature, 1987, 328(6130):543-547.

Chalasani, N., et al., The Diagnosis and Management of Nonalcoholic Fatty Liver Disease: Practice Guidance From the American Association for the Study of Liver Diseases, Hepatology, 2018, 67(1):328-357.

Chaouat, G., et al., Control of fetal survival in CBAxDBA/2 mice by lymphokine therapy, J. Reprod. Feri., 1990, 89(2):447-458.

Chaouat, G., et al., IL-10 prevents naturally occurring fetal loss in the CBA x DBA/2 mating combination, and local defect in IL-10 production in this abortion-prone combination is corrected by in vivo injection of IFN-tau, J. Immunol., 1995,154(9):4261-4268, Abstract only.

Chaouat, G., et al., Th1/Th2 Paradigm in Pregnancy: Paradigm lost? Cytokines in Pregnancy/Early Abortion Reexamining the Th1/Th2 Paradigm, Int. Arch. Allergy Immunol., 2004, 134(2):93-119.

(56) References Cited

OTHER PUBLICATIONS

Chard, T., et al., Early pregnancy factor, Biol. Res. Pregnancy Perinatol., 1987, 8(2 2D Half):53-56, Abstract only.
Chen, C., et al., Monitoring embryos after in vitro fertilization using early pregnancy factor, Ann. N. Y. Acad. Sci., 1985, 142:420-428.
Chen, J. D., et al., A transcriptional co-repressorthat interacts with nuclear hormone receptors, Nature, 1995, 377(6548):454-457.
Choudhury, S. R., et al. Human reproductive failure I: Immunological factors, Human Reprod. Update, 2001,7(2):113-134. .
Clarke, F. M., et al., Identification of molecules involved in the 'early pregnancy factor' phenomenon, J. Reprod. Fertil., 1991,93(2):525-539.
Clarke, F. M., Identification of molecules and mechanisms involved in the 'early pregnancy factor' system, Reprod. Fertil. Dev., 1992, 4(4):423-433.
Collier, M., et al., Biochemical and pharmacological characterization of human embryo-derived activating factor, Hum. Reprod., 1988, 3(8):993-998, Abstract only.
Constantinescu, C. S., et al., Experimental Autoimmune Encephalomyelitis (EAE) as a Model for Multiple Sclerosis (MS), British J. Pharmacology, 2011,164(4):1079-1106.
Cooper, D. W., et al., Failure to detect altered rosette inhibition titres in human pregnancy serum, J. Reprod. Fertil., 1981,61(1):241-245.
Coulam, C. B., et al., Preimplantation Factor (PIF) Predicts Subsequence Pregnancy Loss, The American Fertility Society 50th Annual Meeting, San Antonio, TX, Nov. 5-10, 1994, (Abstract).
Coulam, C. B., et al., Preimplantation Factor (PIF) Predicts Subsequent Pregnancy Loss, Am. J. Reprod. Immunol., 1995, 34(2):88-92. .
Critser, E. S., et al., The Role of Platelet-Activating Factor in Reproduction, Chapter 15 in Immunological Obstetrics, W. W. Norton, New York, 1993, pp. 202-215.
Cross, K. P., et al., Single dose dexamthasone for mild to moderate asthma exacerbations, Can. Fam. Phys., 2011, 57:1134-1136.
Curti, B. D., Physical barriers to drug delivery in tumors, Crit. Rev. Oncol. Hematol., 1993, 14(1):29-39.
Dasgupta, N., et al. Neuronopathic Gaucher Disease: Dysregulated mRNAs and miRNAs in Brain Pathogenesis and Effects of Pharmacologic Chaperone Treatment in a Mouse Model, Human Molecular Genetics, 2015, 24(24):7031-7048.
Database YbuOrit [Online], Nuclear receptor corepressor 2 (N-CoR2) (Silencing mediator of.
Retinoic acid and thyroid hormone receptor) (SMRT) (SMRTe) (Thyroid-, retinoic-acid-receptor-associated corepressor) (T3 receptor-associating factor) (Trac) (Ctg repeat protein 26) (SMAP270), retrieved from EBI accession No. UNIPROT:Q9Y618 Database accession No. Q9Y618 (Nov. 1, 1999).
Dermer, G. B., Another Anniversary for the War on Cancer, Bio/Technology, 1994, 12:320.
Dinh, T. A., et al., The epidemiology of cancer in pregnancy, In Cancer and Pregnancy, Barnea, E. R et al., Eds., Springer, 2005,1:1-5.
Diouf, I., et al., Monocyte Activation and T Cell Inhibition in Plasmodium +lciparum-+544 nfecied Placenta, J. Infect. Dis., 2004,189(12):2235-2242.
Dong, V. M., et al., Transplantation tolerance: the concept and its applicability, Pediatr. Transplantation, 1999, 3(3):181-192.
Dressman, H. K., et al., Gene expression profiles of multiple breast cancer phenotypes and response to neoadjuvant Chemotherapy, Clin. Cancer Res., 2006,12(3):819-826.
Du, W. W., et al., Inhibition of dexamthasone-induced fatty liver development by reducing miR-17-5p levels, Mol. Ther., 2015, 23(7):1222-1233.
Duzyj, C. M., et al., PreImplantation Factor (PIF*) Promotes Embryotrophic and Neuroprotective Decidual Genes: Effect Negated by Epidermal Growth Factor, J. Neurodevelopmental Disorders, 2014, 6(1):36.
Dyment, D. A., et al., Genetics of multiple sclerosis, Lancet Neurol., 2004, 3(2):104-110.

Eisenbarth, G. S., et al., Anti-thymocyte globulin and prednisone immunotherapy of recent onset type 1 diabetes mellitus, Diabetes Res., 1985, 2(6):271-276.
Elad, S., et al., Budesonide: A novel treatment for oral chronic graft versus host disease, Oral Surg. Oral Med. Oral Pathol. Oral Radiol. Endod., 2003, 95(3):308-311.
Elkin, G., et al., Prevention of diabetes in nonobese diabetic mice by nonmyeloablative allogeneic bone marrow transplantation, Exp. Hematol., 2004, 32(6):579-584.
Fernandez, E., et al., Cancer and pregnancy: Clinical management and biological analogy, in Barnea, E. R., et al. (Eds), Implantation and Early Pregnancy in Humans, Carnforth: Parthenon Publishing, 1994, pp. 355-377.
Ferrara, J. L. M., et al., Acute Graft Versus Host Disease: Pathophysiology, Risk Factors, and Prevention Strategies, Clin. Adv. Hematol. Oncol., 2005, 3(5):415-419, 428.
Fiocchi, C., Intestinal Inflammation: a complex interplay of immune and nonimmune cell interactions, Am. Physiol., 1997, 273(4):G769-G775.
Fischer, D. D., et al., Isolation and Characterization of a Novel Class II Histone Deacetylase, HDAC10, J. Biol. Chern., 2002, 277(8):6656-6666.
Fortin, M., et al., TGF-2 and PGE2 in Rabbit Blastocoelic Fluid Can Modulate GM-CSF Production by Human Lymphocytes, Am. J. Reprod. Immunol., 1997, 38(2):129-139.
Freshney, R. I., Culture of Animal Cells, A Manual of Basic Technique, Alan R. I iss, Inc., New York, NY, 1983, pp. 3-4.
Freshney, R. I., Culture of Animal Cells, A Manual of Basic Technique, Wiley-Liss, Inc., New York, NY, 1994, p. 5.
Fuzzi, B., et al., HLA-G expression in early embryos is a fundamental prerequisite for the obtainment of pregnancy, Eur. J. Immunol., 2002, 32(2):311-315.
Gardner, D., et al., Complex physiologically based serum-free culture media increase mammalian embryo development, 10th World Congress on In Vitro Fertilization and Assisted Reproduction, May 24-28, 1997, p. 187-190.
Gardner, D. K., et al., Culture of viable human blastocysts in defined sequential serum-free media, Hum. Reprod., 1998,13(suppl 3):148-160.
Gonzales, R. R., et al., Preimplantation factors (PIF) embryo-derived immunomodulatory peptides: possible implications for maternal recognition and allograft tolerance, 2002, 22nd Annual Meeting of the American Society for Reproductive Immunology, Chicago, IL (abstract).
Gonzai F7, R. R., et al., Preimplantation Factor (PIF*) May Modulate Maternal Immunity (CD2), Vii International Congress of Reproductive Immunology, Organized by ISIR, The International Society for Immunology of Reproduction, 2001, Opatja, Croatia; also published in Am. J. Reproduction Immunology, 2001, 46(1):68-69 (Abstract).
Gonzales, R. R., et al., Preimplantation factor (PIE) could be a portion of CD2 or a homologue peptide, 57th Annual Meeting of the American Society for Reproductive Medicine, Orlando, FL, Oct. 20-25, 2001, (abstract).
Gonzai F7, R. R., et al., Preimplantation Factors (PIF) embryo-derived immunomodulatory peptides: possible implications for maternal recognition and allograft tolerance, American Journal of Reproductive Immunology, 2002, 47(6):347.
Gonzai F7, R. R., et al., Immunomodulatory features of preimplantation factors (PIF) from mouse embryos, 11th World Congress on Human Reproduction, Montreal, Canada, Jun. 1-4, 2002, (Abstract).
Goodman, et al., The Pharmacological Basis of Therapeutics, 6th Ed., MacMillan Publ. Co., New York, 1980, TOC only.
Goodnow, C. C., Pathways for self-tolerance and the treatment of autoimmune diseases, The Lancet, 2001, 357:2115-2121.
Guenther, M. G., et al., A core SMRT corepressor complex containing HDAC3 and TBL1, a WD40-repeat protein linked to deafness, Genes Dev., 2000,14(9):1048-1057.
Guller, S., et al., The role of placental Fas ligand in maintaining immune privilege at maternal-fetal interfaces, Semin. Reprod. Endocrinol., 1999, 17(1):39-44.
Gura, T., Systems for identifying new drugs are often faulty, Science, 1997, 278(5340): 1041-1042.

(56) References Cited

OTHER PUBLICATIONS

Hafler, D. A., Multiple sclerosis, J. Clin. Invest., 2004, 113(6):7B8-794.

Hardy, K., et al., Growth factor expression and function in the human and mouse preimplantation embryo, J. Endocrinol., 2002,172(2):221-236.

Herold, K. C., et al., Anti-Cd3 Monoclonal Antibody In New-Onset Type 1 Diabetes Mellitus, N. Engl. J. Med., 2002, 346(22):1692-1698.

Heyner, S., Growth factors in preimplantation development: role of insulin and insulin-like growth factors, Early Pregnancy: Biol. & Medicine, 1997, 3(3):153-163.

Ho, H. N., et al., Distribution of Th1 and Th2 cell populations in human peripheral and decidual T cells from normal and anembryonic pregnancies, Fertil..Steril., 2001,76(4):797-803.

Hruby, V. J., et al., Synthesis of oligopeptide and peptidomimetic libraries, Curr. Op. Chern. BioL, 1997, 1(1):114-119.

Hruby, V. J., et al., Conformational and Topographical Considerations in Designing Agonist Peptidomimetics from Peptide Leads, Curr. Med. Cham., 2000, 7(9): 945-970.

Huggett, A. C., et al., Characterization of a hepatic proliferation inhibitor (HPI): effect of HPI on the growth of normal liver cells - comparison with transforming growth factor beta, J. Cell. Biochem., 1987, 35(4):305-314; also published in Growth Regulation of Cancer, pp. 55-64.

Hughes, R.A.C., Systematic Reviews of Treatment for Inflammatory Demyelinating Neuropathy; J. Anat. 2002, 200(4):331-339.

Hunter, C., et al., Selective inhibitors of Kv11.1 regulate IL-6 expression by macrophages in response to TRL/IL-1R ligands, The Scientific World Journal, 2010, 10:1580-1596.

Irving, P. M., et al., Review article: Appropriate use of corticosteroids in Crohn's disease, Alimentary Pharmacol. Ther., 2007, 26:313-329.

Jain, R. K., Barriers to drug delivery in solid tumors, Sci. Am., 1994, 271(1):58-65.

Janeway, Jr., C. A., et al., Eds., Immunobiology, The Immune System in Health and Disease, Third Edition, Garland Publishing Inc., 1997, p. 7:25 and 9:31.

Jauniaux, E., et al., Preface: Future Directions and Limitations, in Jauniaux, E., et al.,.

Eds., Embryonic Medicine and Therapy, Oxford: Oxford University Press, 1997, pp. 7-8.

Jiang, S.-P., et al., Cutting Edge: Multiple Mechanisms of Peripheral T Cell Tolerance to the Fetal "Allograft", J. Immunol., 1998,160(7):3086-3090.

Johnson, K. I., et al., Copolymer 1 reduces relapse rate and improves disability in relapsingremitting multiple sclerosis: Results of phase III multicenter, double-blind placebo-controlled trial, Neurology, 1995, 45(7):1268-1276.

Johnson, 0. L., et al., Peptide and Protein Drug Delivery, in: Encyclopedia of Controlled Drug Delivery, vol. 2,1999, pp. 816-833.

Kaaja, R. J., et al., Manifestations of Chronic Disease During Pregnancy, JAMA, 2005, 294(21):2751-2757.

Karussis, D. M., et al., Inhibition of Acute, Experimental Autoimmune, Encephalomyelitis by the Synthetic Immunomodulator Linomide, Ann. Neurol., 1993, 34(5):654-660.

Kraus, T. A., et al., Oral tolerance and inflammatory bowel disease, Curr. Opin. Gastroenterol., 2005, 21(6):692-696.

Lederman, M. M., et al., Defective Suppressor Cell Generation In Juvenile Onset Diabetes, J. Immunol., 1981, 127(5):2051-2055. .

Li, J., et al., Both corepressor proteins SMRT and N-CoR exist in large protein complexes containing HDAC3, Embo J 2000,19(16):4342-4350.

Liu, J. Q The Yins of T Cell Activation, Sci. STKE, 2005, 2005(265):re1, 8 pages.

Ljungdahl, M., et al., Immune cell distribution in gut-associated lymphoid tissue and synthesis of IL-6 in experimental porcine peritonitis, Eur. Surg. Res., 2000, 32(6):323-330.

Loke, Y, W., et al., Immunology of implantation, Bailliere's Best Pract. Res. Clin. Obstet. Gynaecol., 2000,14(5):827-837.

Margolis, R. L., et al., cDNAs with long CAG trinucleotide repeats from human brain, Hum. Genet., 1997, 100:114-122.

Marketletter, Autoimmune shares collapse on Colloral data in rheumatoid arthritis, Marketletter Publications Ltd., 1999, 2 pp.

Mashima, K., et al., Multiple forms of growth inhibitors secreted from cultured rat liver cells: purification and Characterization, J. Biochem., 1988, 103(6):1020-1026.

Matsuyama, K., et al., Purification of three antibacterial proteins from the culture medium of NIH-Sape-4, an embryonic cell line of Sarcophaga peregrina, J. Biol. Chern., 1988, 263(32):17112-17116.

Mattsson, R., et al., Placental MCH class I antigen expression is induced in mice following in vivo treatment with recombinant interferon gamma, J. Reprod. Immunol., 1991, 19(2):115-129.

Mcfarland, H. F., Correlation between MR and Clinical Findings of Disease Activity in Multiple Sclerosis, AJNR Am. J. NeuroradioL, 1999, 20(10):1777-1778.

Mcguirk, P., et al., Pathogen-specific regulatory T cells provoke a shift in the Th1/Th2 paradigm in immunity to infectious diseases, Trends Immunol., 2002, 23(9):450-455.

Medrano, L., et al., Sequence Analysis of the Polymerase Domain of HIV-1 Reverse Transcriptase in Naive and Zidovudine-Treated Individuals Reveals a Higher Polymorphism in a-Helices as Compared with 3-strands, Virus Genes, 1999,18(3):203-210.

Mellor, A. L, et al., Extinguishing maternal immune responses during pregnancy: implications for immunosuppression, Semin. Immunol., 2001,13(4):213-218.

Mielcarek, M., et al., Graft-vs-host disease after non-myeloablative hematopoietic cell transplantation, Leuk. Lymphona, 2005, 46(9):1251-1260.

Mil I Fr, D. H., et al., A Controlled Trial of Natalizumab for Relapsing Multiple Sclerosis, N. Engl. J. Med., 2003, 348(1):15-23.

Minhas, B.S., et al., Platelet Activating Factor and Conception, Am. J. Reprod. Immunol.,.

1996, 35(3):267-271.

Mirhashemi, R., Cancer and Pregnancy, Edited by Eytan R. Barnea, Eric Jaunlaux, and Peter E. Schwartz, The New England Journal of Medicine Book Review, 2002, 346(24):1921-1922.

Miyamoto, K., et al., Selective COX-2 Inhibitor Celecoxib Prevents Experimental Autoimmune Encephalomyelitis through COX-2-lndependent Pathway, Brain, 2006,129:1984-1992.

Mocellin, S et al., The dual role of IL-10, Trends Immunol., 2003, 24(1):36-43.

Moffett-King, A., Natural Killer Cells and Pregnancy, Nat. Rev. Immunol., 2002, 2(9):656-663.

Moindjie, H., Preimplantation factor is an anti-apoptotic effector in human trophoblasts involving p53 signaling pathway, Cell Death and Disease, 2016, 7, e2504,12 p. .

Morgan, B. A., et al., Approaches to the Discovery of Non-Peptide Ligands for Peptide Receptors and Peptidases, Annual Reports in Medicinal Chemistry, 1989, 24(VI): 243-252.

Morton, H., et al., Studies of the rosette inhibition test in pregnant mice: evidence of immunosuppression?, Proc. R. Sac. Land. B. Biol. Sci., 1976,193(1113):413-419.

Morton, H., et al., An early pregnancy factor detected in human serum by the rosette inhibition test, Lancet, 1977, 1(8008):394-397.

Moschen, A. R., et al., Interleukin-32: A New Proinflammatory Cytokine Involved in Hepatitis C Virus-Related Liver Inflammation and Fibrosis, Hepatology, 2011, 53(6):1819-1829.

Muley, S. A., et al., Treatment of chronic inflammatory demyelinating polyneuropathy with pulsed oral steroids, Arch. Neurol., 2008, 65(11):1460-1464.

Muller, M., et al., Synthetic PreImplantation Factor (sPIF) # Neuroprotective Role in Intracranial Stem Cell Transplantation: Encephalopathy of Prematurity Rat Model, Z. Geburtshilfe Neonatol., DGPM: 26th German Congress for Perinatal Medicine, 2013, 217-V22_3,1 page.

Muller, M., PreImplantation factor promotes neuroprotection by targeting microRNA let-7, PNAS, 2014,111 (38):13882-13887.

Muller, M., et al., 106: Synthetic Preimplantation Factor (sPIF*) Promotes Neuroprotection by Modulating PKA/PKC Kinases, American Journal of Obstetrics & Gynecology, 2015, 212(1):S70-S71.

(56) References Cited

OTHER PUBLICATIONS

Muller, M., et al., PreImplantation Factor Bolsters Neuroprotection via Modulating Protein Kinase A and Protein Kinase C Signaling, Cell Death and Differentiation, 2015, 22:2078-2086.

Nahhas, F., et al., Early Pregnancy Factor (EPF) Determination in Pregnant and IVF/ET Patients, and in Human Embryo Cultures, American Fertility Society 15th Ann. Mtg., San Francisco, CA, 1989, pp. S53-S54 (Abstract).

Nahhas, et al., Human Embryonic Origin Early Pregnancy Factor Before and After Implantation, Am. J. Reprod, Immunol., 1990, 22(3-4):105-108.

Nakamura, K., et al., Delayed and acute effects of interferon-y on activity of an inwardly rectifying K+ channel in cultured human proximal tubule cells, Am. J. Physiol. Renal. Physiol., 2009, 296(1):F46-F53.

Navot, D., et al., Poor oocyte quality rather than implantation failure as a cause of age-related decline in female fertility, Lancet, 1991,337(8754):1375-1377.

Olsen, J. V., et al., Global, In Vivo, and Site-Specific Phosphorylation Dynamics in Signaling Networks, Cell, 2006, 127(3):635-648.

O'Neill, C., Partial characterization of the embryo-derived platelet-activating factor in mice, J. Reprod. FertiL, 1985, 75(2):375-380.

O'Neill, C., et al., Use of a bioassay for embryo-derived platelet activating factor as a means of assessing quality and pregnancy potential of human embryos, FertiL SteriL, 1987, 47(6):969-975.

O'Neill, C., Thrombocytopenia is an initial maternal response to fertilization in the mouse, J. Reprod. Fertil., 1985, 73(2):559-566.

Or, R., et al., The prophylactic potential of fludarabine monophosphate in graft-versus-host disease after bone marrow transplantation in murine models, Bone Marrow Transplantation, 2000, 25(3):263-266.

Or, R., Safety study of preimplantation factor (PIF-1) to treat acute steroid-resistant graft-versus-host disease (GVHD), last updated 2015, available at https://trialbulletin.com/lib/entry/ct-00517907.

Ordentlich, P., et al., Unique forms of human and mouse nuclear receptor corepressor SMRT, Proc. Natl. Acad. Sci. USA, 1999, 96(6):2639-2644.

Paidas, M., et al., Pregnancy Implantation Factor (PIF) Activity Is Correlated With A Pro-Inflammatory Response, 23rd Annual Society for Maternal-Fetal Medicine Conference, San Francisco, CA, Dec. 2002, (Abstract).

Paidas, M., et al., Preimplantation Factor (PIF) Upregulates First Trimester Toll Like Receptor-2, Supporting the Role of PIF as an Embryo Derived Factor Influencing Maternal Innate Immunity, 27th Annual Scientific Meeting of the Society for Maternal-Fetal Medicine, San Francisco, CA, Feb. 5-10, 2007, S140 (Abstract 448).

Paidas, M. J., et al., A Genomic and Proteomic Investigation of the Impact of Preimplantation Factor on Human Decidual Cells, American Journal of Obstetrics and Gynecology, 2010, 202(5):459.e1-459.e8.

Paidas, M. J., et al., Pregnancy and Multiple Sclerosis (Ms): A Beneficial Association. Possible Therapeutic Application of Embryo-Specific Pre-Implantation Factor (PIF*), American Journal of Reproductive Immunology, 2012, 68(6):456-464.

Paidas, M. Treatment of Acute Radiation Syndrome Using PIF, a Natural Immune Modulator, BioIncept, LLC, Project No. 1R41AI120546-01,Jun. 10, 2015, Retrieved from the Internet: https://projectreporter.nih.gov/project/info description.cfm?project-number =1R41AI120546-01 on Nov. 18, 2015.

Park, E.-J., et al., SMRTe, a silencing mediator for retinoid and thyroid hormone receptors-extended isoform that is more related to the nuclear receptor corepressor, Proc. Natl. Acad. Sci. USA, 1999, 96(7):3519-3524.

Pearson, W. R., An Introduction to Sequence Similarity ("Homology") Searching, Current Protocols in Bioinformatics, 2013, Chapters, p. 3.1.1-3.1.8.

Pessina, P., et al., Novel and optimized strategies for inducing fibrosis in vivo: focus on Duchenne Muscular Dystrophy, Skeletal Muscle, 2014, 4(1):7,17 pages.

Piccinni, M. P., et al., Production of IL-4 and leukemia inhibitory factor by T cells of the cumulus oophorus: a favorable microenvironment for pre-implantation embryo development, Eur. J. Immunol., 2001,31(8):2431-2437.

Pinkas, H., et al., Immunosuppressive Activity In Culture Media Containing Oocytes Fertilized In Vitro, Arch. Androl., 1992, 28(1):53-59. .

Pozzilli, P., et al., No. effect of oral insulin on residual beta-cell function in recent-onset type I diabetes (the Imdiab Vii), Diabetologia, 2000, 43(8):1000-1004.

Qin, Z. H., et al., Detection of early pregnancy factor in human sera, Am. J. Reprod. Immunol. Microbial., 1987,13(1):15-18, Abstract only. .

Raghupathy, R., Th1-type immunity is incompatible with successful pregnancy, Immunol. Today, 1997, 18(10):478-482.

Raghupathy, R., Pregnancy: success and failure within the Th1/Th2/Th3 paradigm, Semin. Immunol., 2001, 13(4):219-227.

Rayburn, W. F., Embryonic Medicine and Therapy, (Jauniaux, E., Barnea, E.R., Edwards, R.G., eds.),The New England Journal of Medicine Book Review, 1999, 340(19):1519.

Raz, I., et al., |3-cell function in new-onsettype 1 diabetes and immunomodulation with heat-.

Shock protein peptide (DiaPep277): a randomised, double-blind, phase II trial, Lancet, 2001, 358(9295):1749-1753.

Reeck, G. R., et al., Homology' in Proteins and Nucleic Acids: A Terminology Muddle and A Way Out of It, Cell, 1987, 50(5):667.

Resnick, I. B., et al., Nonmyeloablative stem cell transplantation and cell therapy for malignant and non-malignant diseases, Transpl. Immunol., 2005,14(3-4):207-219.

Rieger, L., et al., Th1- and Th2-like cytokine production by first trimester decidual large granular lymphocytes is influenced by HLA-G and HLA-E, Mol. Hum. Reprod., 2002, 8(3):255-261.

Ripka, A. S., et al., Peptidomimeticdesign, Curr. Op. Chern. Biol., 1998, 2(4):441-452.

Rogers, A. M., et al., Maternal-fetal tolerance is maintained despite transgene-driven trophoblast expression of MHC class I, and defects in Fas and its ligand, Eur. J. Immunol., 1998, 28(11):3479-3487.

Rolfe, B. E Detection of fetal wastage, Fertil. Steril., 1982, 37(5):655-660.

Rolfe, F. G., et al., Cyclosporin A and FK506 Reduce lnterleukin-5 mRNA Abundance by Inhibiting Gene Transcription, Am. J. Respir. Cell Mol. Biol., 1997,17(2):243-250.

Romagnani, S., Lymphokine Production By Human T Cells In Disease States, Annu. Rev. Immunol., 1994, 12:227-257, Abstract only.

Rosario, G. X., et al., Morphological events in the primate endometrium in the presence of a preimplantation embryo, detected by the serum preimplantation factor bioassay, Hum. Reprod., 2005, 20(1):61-71.

Rose, N. R., et al., Manual of Clinical Laboratory Immunology, Fifth Edition, ASM Press, 1997, pp. 20-48.

Roussev, R. G., et al., Clinical Validation Of Preimplantation Factor (PIF) Assay, 2nd World Conference on Preimplantation and Early Pregnancy in Humans, Atlantic City, NJ, May 1994, (Abstract).

Roussev, R. G., et al., A Novel Bioassay for Detection of Preimplantation Factor (PIF), American Society of Reproductive Immunology, XVI Annual Meeting, Jun. 1994, Philadelphia, PA, (abstract).

Roussev, R. G., et al., A Novel Bioassay for Detection of Preimplantation Factor (PIF), Am. J. Reprod. Immunol., 1995, 33(1):68-73. .

Roussev, R. G., et al., Embryonic Origin Of Preimplantation Factor, Society for Gynecological Investigation 42nd Meeting, Chicago, IL, 1995, (Abstract).

Roussev, R. G., et al., Embryonic origin of preimplantation factor (PIF): biological activity and partial characterization, Mol. Hum. Reprod., 1996, 2(11):8B3-887.

Roussev, R. G., et al., Development and Validation of an Assay for Measuring Preimplantation Factor (PIF) of Embryonal Origin, Am. J. Reprod. Immunol., 1996, 35(3):281-287.

Roussev, R. G., et al., Preimplantation Factor Inhibits Circulating Natural Killer Cell Cytotoxicity and Reduces CD69 Expression: Implications for Recurrent Pregnancy Loss Therapy, Reproductive BioMedicine Online, 2013, 26(1):79-87.

(56) References Cited

OTHER PUBLICATIONS

Runmarker, B., et al., Pregnancy is associated with a lower risk of onset and a better diagnosis in multiple sclerosis, Brain, 1995, 118(1):253-261.
Salomon, B., et al., B7/CD28 Costimulation Is Essential for the Homeostasis of the CD4+CD25+ Immunoregulatory T Cells that Control Autoimmune Diabetes, Immunity, 2000, 12(4):431-440.
Sande, S., et al., Identification of Tracs (T3 Receptor-Associating Cofactors), a Family of Cofactors that Associate with, and Modulate the Activity of, Nuclear Hormone Receptors, Mol. Endocrinol., 1996,10(7):813-825.
Sanyal, M. K., et al., Immunoregulatory activity in supernatants from cultures of normal.
Human trophoblast cells of the first trimester, Am. J. Obstet. Gynecol., 1989,161(2):446-453.
Sbracia, M., et al., Preimplantation Factor In Endometriosis: A Potential Role In Inducing Immune Privilege For Ectopic endometrium, PLoS ONE, 2017, 12(9):e0184399, 14 pages.
Schroeder, R. A., et al., Tolerance and the "Holy Grail" of Transplantation, J. ofSurg. Res., 2003, 111:109-119.
Schumacher, Jr., H. R., et al., Primer on the Rheumatic Diseases, Tenth Edition, Arthritis Foundation (1993), pp. 86-89,100-105.
Shainer, R., et al., Immune regulation and oxidative stress reduction by preimplantation factor following syngeneic or allogeneic bone marrow transplantation, Conference Papers In Medicine, 2013, 2013:1-8.
Shainer, R., et al. PB-277: Pre-lmplantation Factor (PIF) as Prophylaxis after Radiation Exposure: Immune-Regulation and iNOS Reduced Expression, Poster presented in The 7th • Congress of the Federation of the Israel Societies for Experimental Biology, Feb. 10-13, 2014.
Shainer, R., et al., PreImplantation Factor (PIF) Therapy Provides Comprehensive Protection against Radiation Induced Pathologies, Oncotarget, 2016, 7(37):58975-58994.
Sharma, S., et al., Genes regulating implantation and fetal development: a focus on mouse knockout models, Front. Biosci., 2006,11:2123-2137.
Shi, Y., et al., Sharp, an inducible cofactor that integrates nuclear receptor repression and activation, Genes Dev., 2001, 15(9): 1140-1151.
Shurtz-Swirski, R., et al., Human Embryo Modulates Placental Function in the First Trimester; Effects of Neural Tissues upon Chorionic Gonadotropin and Progesterone Secretion, Placenta, 1991,12(5):521-531.
Shurtz-Swirski, R., et al., Patterns of secretion of human chorionic gonadotropin by superfused placental explants and the embryoplacental relationship following maternal use of medications, Hum. Reprod., 1992, 7(3):30Q-304.
Shurtz-Swirski, R., et al., In Vitro Effect of Anticardiolipin Autoantibodies Upon Total and Pulsatile Placental hCG Secretion During Early Pregnancy, Am. J. Reprod. Immunol., 1993, 29(4):206-210.
Shurtz-Swirski, R., et al., Anti-Cardiolipin Antibodies Affect Total And Pulsatile Placental Hcg Secretion During Early Pregnancy, Israel Conference of Fertility, Tel Aviv, Israel, 1993, (Abstract).
Sicotte, N. L, et al., Onset of Multiple Sclerosis Associated with Anti-TNF Therapy, Neurology, 2001, 57:1885-1888.
Singh, V. K., et al., Animal models for acute radiation syndrome drug discovery, Expert Opin. Drug Discov., 2015,10(5):497-517.
Sipka, S., et al., Glucocorticosteroid dependent decrease in the activity of calcineurin in the peripheral blood mononuclear cells of patients with systemic lupus erythematosus, Ann. Rheum. Dis., 2001,60(4):380-384. .
Skolnick, J., et al., From genes to protein structure and function: novel applications of computational approaches in the genomic era, Trends Biotechnol., 2000,18(1):34-39.
Skyler, J. S., et al., Use of Inhaled Insulin in a Basal/Bolus Insulin Regimen in Type 1 Diabetic Subjects, Diabetes Care, 2005, 28(7):1630-1635.
Slavin, S., et al., The graft-versus-leukemia (GVL) phenomenon: is GVL separable from GVHD?, Bone Marrow Transplant, 1990, 6(3):155-161.
Slavin, S., et al., Non-myeloablative stem cell transplantation for the treatment of cancer and life-threatening non-malignant disorders; past accomplishments and future goals, Transfusion and Apheresis Sci., 2002, 27(2):159-166.
Smart, Y. C., et al., Early pregnancy factor: its role in mammalian reproduction - research review, Fertil. Steril., 1981, 35(4):397-402.
Smart, Y. C., et al., Validation of the rosette inhibition test for the detection of early.
Pregnancy in women, Fertil. Steril., 1982,37(6):779-785.
Somerset, D. A., et al., Normal human pregnancy is associated with an elevation in the human suppressive CD25+ CD4+ regulatory T-cell subset, Immunology, 2004, 112(1):38-43.
Sospedra, M., et al., Immunology of Multiple Sclerosis, Annu. Rev. Immunol., 2005, 23:683-747.
Stewart, C. L, et al., Preimplantation Development of the Mammalian Embryo and Its Regulation by Growth Factors, Dev. Genetics, 1997, 21:91-101.
Streifler, J., et al., Effects of dexamethasone in myotonic muscular dystrophy, J. Neruol. Neruosurg. Psychiartry, 1987, 50(7):937.
Sturzebecher, S., et al., Expression profiling identifies responder and non-responder phenotypes to interferon- in multiple sclerosis, Brain, 2003,126(6):1419-1429.
Szekeres-Bartho, J., Immunological Relationship Between The Mother And The Fetus, Int. Rev. Immunol., 2002, 21(6):471-495.
Tangri, S., et al., Maternal Anti-Placental Reactivity in Natural, Immunologically-Mediated Fetal Resorptions, J. Immunol., 1994,152(10):4903-4911.
Taubes, G., Vaccines. Malaria Parasite Outwits The Immune System, Science, 2000, 290(5491):435.
Than, N. G., et al., Embryo-Placento-Maternal Interaction and Biomarkers: From Diagnosis to Therapy-A Workshop Report, Placenta, 2007, 28(Suppl. A)(21):S107-S110.
The staff at US Pharmacists, Autoimmune disease, US Pharm., 2016, 41(6):13-14.
Thwaites, G. E., et al., Dexamethasone for the treatment of tuberculosis meningitis in adolescents and adults, N. Engl. J. Med., 2004, 351:1741-1751.
TNF neutralization in MS: results of a randomized, placebo-controlled multicenter study. The Lenercept Multiple Sclerosis Study Group and The University of British Columbia MS/MRI Analysis Group, Neurology, 1999, 53:457-465.
Tokuriki, N., et al., Stability Effects of Mutations and Protein Evolvability, Current Opinion in Structural Biology, 2009,19:596-604.
Treister, N., et al., An open label phase II randomized trial of topical dexamethasone and tacrolimus solutions for the treatment of oral chronic graft vs host disease, Biol. Blood Marrow Transplant, 2016, 22:2084-2091.
Truitt, R. L, The Mortimer M. Bortin Lecture: To destroy by the Reaction of Immunity: the Search for Separation of Graft-versus-Leukemia and Graft Host, Biol. Blood Marrow Transplant, 2004, 10(8):505-523.
U.S. Congress, Office of Technology Assessment, Infertility. Medical and Social Choices, OTA-BA-358, Washington, DC: Government Printing Office, May 1988.
Vallera, D. A., Targeting T Cells for GVHD Therapy, Semin. Cancer Biol., 1996, 7(2):57-64.
Valverde, P., et al., Potassium channel-blockers as therapeutic agents to interfere with bone resorption of periodontal Disease, J. Dental. Res, 2005, 84(6):488-499.
Verma, A. K., et al., Anti-mullerian hormone: A marker of ovarian reserve and its association with polycystic ovarian syndrome, J. Clin. Diagn. Res., 2016, 10(12):QC10-QC12.
Wegmann, T. G., et al., Bidirectional cytokine interactions in the maternal-fetal relationship: is successful pregnancy aTH2 phenomenon?, Immunol. Today, 1993, 14(7):353-356, Abstract only.
Weiss, L., et al., Induction of resistance to diabetes in non-obese diabetic mice by targeting CD44 with a specific monoclonal antibody, Proc. Natl. Acad. Sci. USA, 2000, 97(1):285-290.

(56) References Cited

OTHER PUBLICATIONS

Weiss. L, et al., Preimplantation Factor (PIF) Analog Prevents Type I Diabetes Mellitus (TIDM) Development by Preserving Pancreatic Function in NOD Mice, Endocrine, 2011, 40:42-54.
Weiss, L, et al., Preimplantation factor (PIF) reverses neuroinflammation while promoting.
Neural repair in EAE model, J. Neurol. Sci., 2012, 312(1-2):146-157.
Whyte, A., et al., Reproductive immunology. Early pregnancy factor, Nature, 1983, 304(5922):121-122.
Wickramasinghe, S. N., et al., Blood and bone marrow changes in malaria, Baillieres Best Pract. Res. Clin. Haematol., 2000,13(2):277-299.
Wu, M. Y., et al., Increase in the Production of Interleukin-10 Early After Implantation is Related to the Success of Pregnancy, Am. J. Reprod. Immunol., 2001,46(6):386-392.
Wu, A. I., et al., Tumor necrosis factor-a regulation of CD4+C25+ T cell levels in NOD mice, Proc. Natl. Acad. Sci. USA, 2002, 99(19):12287-12292.
Yampolsky, L. Y., et al., The exchangeability of amino acids in proteins, Genetics, 2005, 170:1459-1472.
Zhang, X., et al., MicroRNA Expression Profile in Hyperoxia-Exposed Newborn Mice during the Development of Bronchopulmonary Dysplasia, Respiratory Care, 2011,56(7):1009-1015.
Zhang, J., et al., The N-CoR-HDAC3 Nuclear Receptor Corepressor Complex Inhibits the INK Pathway through the Integral Subunit GPS2, Mol. Cell, 2002, 9(3):611-623.
Zhou, M., et al., Expanded cohorts of maternal CD8+ T-cells specific for paternal MCH class I accumulate during pregnancy, J. Reprod. Immunol., 1998, 40(1):47-62.

\* cited by examiner

PIF IS A BENIGN STEROID
Regulates Immune Response / Endogenous Cortisone Competitor

VOLTAGE DEPENDENT K+ CHANNEL BETA SUBUNIT

PIF BINDS
Same Binding Site (Receptor) as Cortisone

PIF SPECIFICITY: SINGLE AA MUTATION ABOLISHES ACTIVITY
Effect on Immune and Neural Cells

A BV-2 cells (50 nM)

B N2a cells (300 nM)

mPIF (mutate) effect compared to sPIF (wild type) or PIFscr (scrambled)

INTACT PIF CROSSES THE BLOOD BRAIN BARRIER
Clears Rapidly from Circulation Mouse injected SQ and brain is harvested
after 6 h -HPLC/Mass spec PIF clearance from circulation

PIF PRESENT IN BRAIN, ABSENT IN CIRCULATION
PIF Targets Neurons and Microglia PIF presence in the brain 12h post injection PIF measured in the serum after 12h using mass-spectrometry is not detected

PIF REVERSES ADVANCED BRAIN INJURY
Promotes Nerve Regeneration

Myelin (HBP)

Neuron Markers (NeuN and Cux1)

PIF PREVENTS ACUTE PARALYSIS
Prevents Access of Inflammatory Cells to the Spinal Cord EAE mouse model – injected
PLP / Tuberculin / Pertussis, P<0.002 Mann-Whitney

PIF REVERSES BRAIN INFECTION
Reduces Inflammatory Cells Access to the Brain

PIF REVERSES RELAPSING/REMITTING CHRONIC PARALYSIS
Episodic PIF vs. Episodic Copaxone (GA) (60%) vs. PBS (0%) (EAE)

Subcutaneous episodic injection (SC) 0.75 mg/kg x2/day
$P<0.0001$ vs. control

PIF $<0.05$ vs. PBS, GA

PIF PROTECTS AGAINST VASCULAR DAMAGE
(ApoE + Murine Model + High-Fat Diet

SEQUENCE LISTING

<160> NUMBER OF SEQ ID NOS: 23

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any amino acid except arginine

<400> SEQUENCE: 1

Met Val Xaa Ile Lys Pro Gly Ser Ala Asn Lys Pro Ser Asp Asp
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa is any amino acid except arginine

<400> SEQUENCE: 2

Xaa Val Arg Ile Lys Pro Gly Ser Ala Asn Lys Pro Ser Asp Asp
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa is any amino acid except arginine
<220> FEATURE:
<221> NAME/KEY: VARIANT
<222> LOCATION: (3)..(3)
<223> OTHER INFORMATION: Xaa is any amino acid except arginine

<400> SEQUENCE: 3

Xaa Val Xaa Ile Lys Pro Gly Ser Ala Asn Lys Pro Ser Asp Asp
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)..(6)
<223> OTHER INFORMATION: Xaa is any amino acid except arginine

<400> SEQUENCE: 4

Met Val Arg Ile Lys Xaa Gly Ser Ala Asn Lys Pro Ser Asp Asp
1               5                   10                  15

<210> SEQ ID NO 5
<211> LENGTH: 15
<212> TYPE: PRT
<213> ORGANISM: Artificial Sequence

```
<220> FEATURE:
<223> OTHER INFORMATION: Synthetic peptide
<220> FEATURE:
<221> NAME/KEY: VARIANT
<222> LOCATION: (4)..(4)
<223> OTHER INFORMATION: Xaa is any amino acid except arginine

<400> SEQUENCE: 5

Met Val Arg Xaa Lys Pro Gly Ser Ala Asn Lys Pro Ser Asp Asp
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)..(2)
<223> OTHER INFORMATION: Xaa is any amino acid except arginine

<400> SEQUENCE: 6

Met Xaa Arg Ile Lys Pro Gly Ser Ala Asn Lys Pro Ser Asp Asp
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Met Val Arg Ile Lys Glu Gly Ser Ala Asn Lys Pro Ser Asp Asp
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Met Val Arg Gly Lys Pro Gly Ser Ala Asn Lys Pro Ser Asp Asp
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

Met Glu Arg Ile Lys Pro Gly Ser Ala Asn Lys Pro Ser Asp Asp
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Ala Val Arg Ile Lys Pro Gly Ser Ala Asn Lys Pro Ser Asp Asp
```

```
                1               5                    10                   15
```

<210> SEQ ID NO 11
<211> LENGTH: 15
<212> TYPE: PRT
<213> ORGANISM: Artificial Sequence
<220> FEATURE:
<223> OTHER INFORMATION: Artificial sequence

<400> SEQUENCE: 11

```
Met Val Arg Ile Lys Pro Gly Ser Ala Asn Lys Pro Ser Asp Asp
1               5                   10                  15
```

<210> SEQ ID NO 12
<211> LENGTH: 1019
<212> TYPE: PRT
<213> ORGANISM: Homo sapiens

<400> SEQUENCE: 12

```
Met Arg Tyr Arg Leu Ala Trp Leu Leu His Pro Ala Leu Pro Ser Thr
1               5                   10                  15

Phe Arg Ser Val Leu Gly Ala Arg Leu Pro Pro Glu Arg Leu Cys
                20                  25                  30

Gly Phe Gln Lys Lys Thr Tyr Ser Lys Met Asn Asn Pro Ala Ile Lys
            35                  40                  45

Arg Ile Gly Asn His Ile Thr Lys Ser Pro Glu Asp Lys Arg Glu Tyr
50                  55                  60

Arg Gly Leu Glu Leu Ala Asn Gly Ile Lys Val Leu Leu Ile Ser Asp
65                  70                  75                  80

Pro Thr Thr Asp Lys Ser Ser Ala Ala Leu Asp Val His Ile Gly Ser
                85                  90                  95

Leu Ser Asp Pro Pro Asn Ile Ala Gly Leu Ser His Phe Cys Glu His
                100                 105                 110

Met Leu Phe Leu Gly Thr Lys Lys Tyr Pro Lys Glu Asn Glu Tyr Ser
            115                 120                 125

Gln Phe Leu Ser Glu His Ala Gly Ser Ser Asn Ala Phe Thr Ser Gly
        130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Glu
                165                 170                 175

Ser Cys Lys Asp Arg Glu Val Asn Ala Val Asp Ser Glu His Glu Lys
                180                 185                 190

Asn Val Met Asn Asp Ala Trp Arg Leu Phe Gln Leu Glu Lys Ala Thr
            195                 200                 205

Gly Asn Pro Lys His Pro Phe Ser Lys Phe Gly Thr Gly Asn Lys Tyr
        210                 215                 220

Thr Leu Glu Thr Arg Pro Asn Gln Glu Gly Ile Asp Val Arg Gln Glu
225                 230                 235                 240

Leu Leu Lys Phe His Ser Ala Tyr Tyr Ser Ser Asn Leu Met Ala Val
                245                 250                 255

Cys Val Leu Gly Arg Glu Ser Leu Asp Asp Leu Thr Asn Leu Val Val
                260                 265                 270

Lys Leu Phe Ser Glu Val Glu Asn Lys Asn Val Pro Leu Pro Glu Phe
            275                 280                 285

Pro Glu His Pro Phe Gln Glu Glu His Leu Lys Gln Leu Tyr Lys Ile
        290                 295                 300
```

```
Val Pro Ile Lys Asp Ile Arg Asn Leu Tyr Val Thr Phe Pro Ile Pro
305                 310                 315                 320

Asp Leu Gln Lys Tyr Lys Ser Asn Pro Gly His Tyr Leu Gly His
            325                 330                 335

Leu Ile Gly His Glu Gly Pro Gly Ser Leu Leu Ser Glu Leu Lys Ser
                340                 345                 350

Lys Gly Trp Val Asn Thr Leu Val Gly Gly Gln Lys Glu Gly Ala Arg
            355                 360                 365

Gly Phe Met Phe Phe Ile Ile Asn Val Asp Leu Thr Glu Glu Gly Leu
370                 375                 380

Leu His Val Glu Asp Ile Ile Leu His Met Phe Gln Tyr Ile Gln Lys
385                 390                 395                 400

Leu Arg Ala Glu Gly Pro Gln Glu Trp Val Phe Gln Glu Cys Lys Asp
                405                 410                 415

Leu Asn Ala Val Ala Phe Arg Phe Lys Asp Lys Glu Arg Pro Arg Gly
                420                 425                 430

Tyr Thr Ser Lys Ile Ala Gly Ile Leu His Tyr Tyr Pro Leu Glu Glu
            435                 440                 445

Val Leu Thr Ala Glu Tyr Leu Leu Glu Glu Phe Arg Pro Asp Leu Ile
450                 455                 460

Glu Met Val Leu Asp Lys Leu Arg Pro Glu Asn Val Arg Val Ala Ile
465                 470                 475                 480

Val Ser Lys Ser Phe Glu Gly Lys Thr Asp Arg Thr Glu Glu Trp Tyr
                485                 490                 495

Gly Thr Gln Tyr Lys Gln Glu Ala Ile Pro Asp Glu Val Ile Lys Lys
            500                 505                 510

Trp Gln Asn Ala Asp Leu Asn Gly Lys Phe Lys Leu Pro Thr Lys Asn
            515                 520                 525

Glu Phe Ile Pro Thr Asn Phe Glu Ile Leu Pro Leu Glu Lys Glu Ala
            530                 535                 540

Thr Pro Tyr Pro Ala Leu Ile Lys Asp Thr Ala Met Ser Lys Leu Trp
545                 550                 555                 560

Phe Lys Gln Asp Asp Lys Phe Leu Pro Lys Ala Cys Leu Asn Phe
                565                 570                 575

Glu Phe Phe Ser Pro Phe Ala Tyr Val Asp Pro Leu His Cys Asn Met
            580                 585                 590

Ala Tyr Leu Tyr Leu Glu Leu Leu Lys Asp Ser Leu Asn Glu Tyr Ala
            595                 600                 605

Tyr Ala Ala Glu Leu Ala Gly Leu Ser Tyr Asp Leu Gln Asn Thr Ile
            610                 615                 620

Tyr Gly Met Tyr Leu Ser Val Lys Gly Tyr Asn Asp Lys Gln Pro Ile
625                 630                 635                 640

Leu Leu Lys Lys Ile Ile Glu Lys Met Ala Thr Phe Glu Ile Asp Glu
                645                 650                 655

Lys Arg Phe Glu Ile Ile Lys Glu Ala Tyr Met Arg Ser Leu Asn Asn
            660                 665                 670

Phe Arg Ala Glu Gln Pro His Gln His Ala Met Tyr Tyr Leu Arg Leu
            675                 680                 685

Leu Met Thr Glu Val Ala Trp Thr Lys Asp Glu Leu Lys Glu Ala Leu
            690                 695                 700

Asp Asp Val Thr Leu Pro Arg Leu Lys Ala Phe Ile Pro Gln Leu Leu
705                 710                 715                 720
```

-continued

```
Ser Arg Leu His Ile Glu Ala Leu Leu His Gly Asn Ile Thr Lys Gln
            725                 730                 735

Ala Ala Leu Gly Ile Met Gln Met Val Glu Asp Thr Leu Ile Glu His
        740                 745                 750

Ala His Thr Lys Pro Leu Leu Pro Ser Gln Leu Val Arg Tyr Arg Glu
    755                 760                 765

Val Gln Leu Pro Asp Arg Gly Trp Phe Val Tyr Gln Gln Arg Asn Glu
770                 775                 780

Val His Asn Asn Cys Gly Ile Glu Ile Tyr Tyr Gln Thr Asp Met Gln
785                 790                 795                 800

Ser Thr Ser Glu Asn Met Phe Leu Glu Leu Phe Cys Gln Ile Ile Ser
                805                 810                 815

Glu Pro Cys Phe Asn Thr Leu Arg Thr Lys Glu Gln Leu Gly Tyr Ile
            820                 825                 830

Val Phe Ser Gly Pro Arg Arg Ala Asn Gly Ile Gln Gly Leu Arg Phe
        835                 840                 845

Ile Ile Gln Ser Glu Lys Pro Pro His Tyr Leu Glu Ser Arg Val Glu
    850                 855                 860

Ala Phe Leu Ile Thr Met Glu Lys Ser Ile Glu Asp Met Thr Glu Glu
865                 870                 875                 880

Ala Phe Gln Lys His Ile Gln Ala Leu Ala Ile Arg Arg Leu Asp Lys
                885                 890                 895

Pro Lys Lys Leu Ser Ala Glu Cys Ala Lys Tyr Trp Gly Glu Ile Ile
            900                 905                 910

Ser Gln Gln Tyr Asn Phe Asp Arg Asp Asn Thr Glu Val Ala Tyr Leu
        915                 920                 925

Lys Thr Leu Thr Lys Glu Asp Ile Ile Lys Phe Tyr Lys Glu Met Leu
    930                 935                 940

Ala Val Asp Ala Pro Arg Arg His Lys Val Ser Val His Val Leu Ala
945                 950                 955                 960

Arg Glu Met Asp Ser Cys Pro Val Val Gly Glu Phe Pro Cys Gln Asn
                965                 970                 975

Asp Ile Asn Leu Ser Gln Ala Pro Ala Leu Pro Gln Pro Glu Val Ile
            980                 985                 990

Gln Asn Met Thr Glu Phe Lys Arg Gly Leu Pro Leu Phe Pro Leu Val
        995                 1000                1005

Lys Pro His Ile Asn Phe Met Ala Ala Lys Leu
    1010                1015
```

```
<210> SEQ ID NO 13
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any naturally occurring or non-natural
      amino acid

<400> SEQUENCE: 13

Met Val Xaa Ile Lys Pro Gly Ser Ala Asn Lys Pro Ser Asp Asp
1               5                   10                  15

<210> SEQ ID NO 14
<211> LENGTH: 14
<212> TYPE: PRT
```

<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any naturally occurring or non-natural
      amino acid

<400> SEQUENCE: 14

Met Val Xaa Ile Lys Pro Gly Ser Ala Asn Lys Pro Ser Asp
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any naturally occurring or non-natural
      amino acid

<400> SEQUENCE: 15

Met Val Xaa Ile Lys Pro Gly Ser Ala Asn Lys Pro Ser
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any naturally occurring or non-natural
      amino acid

<400> SEQUENCE: 16

Met Val Xaa Ile Lys Pro Gly Ser Ala Asn Lys Pro
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any naturally occurring or non-natural
      amino acid

<400> SEQUENCE: 17

Met Val Xaa Ile Lys Pro Gly Ser Ala Asn Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any naturally occurring or non-natural amino acid

<400> SEQUENCE: 18

Met Val Xaa Ile Lys Pro Gly Ser Ala Asn
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any naturally occurring or non-natural
      amino acid

<400> SEQUENCE: 19

Met Val Xaa Ile Lys Pro Gly Ser Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any naturally occurring or non-natural
      amino acid

<400> SEQUENCE: 20

Met Val Xaa Ile Lys Pro Gly Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any naturally occurring or non-natural
      amino acid

<400> SEQUENCE: 21

Met Val Xaa Ile Lys Pro Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any naturally occurring or non-natural
      amino acid

<400> SEQUENCE: 22

Met Val Xaa Ile Lys
1               5

```
<210> SEQ ID NO 23
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: Xaa is any naturally occurring or non-natural
      amino acid

<400> SEQUENCE: 23

Met Val Xaa Ile
1
```

MUTANT PEPTIDES AND METHODS OF TREATING SUBJECTS USING THE SAME

CROSS-REFERENCE TO RELATED APPLICATIONS

This application is a U.S. National Stage entry under 35 U.S.C. § 371 of International Application No. PCT/US2016/022725, filed on Mar. 16, 2016, which claims priority to and benefit of International Application Serial No. PCT/US15/58877, filed Nov. 3, 2015, entitled "PIF Binding as a Marker for Immune Dysregulation," International Application Serial No. PCT/US15/50532 filed Sep. 16, 2015, entitled "Compositions and Methods for Treating Acute Radiation Syndrome", and U.S. Provisional Application Ser. No. 62/211,660 filed Aug. 28, 2015, entitled "Compositions and Methods for the Treatment of Neurodamage". The contents of each application are incorporated herein by reference in their respective entireties. This application is related to U.S. application Ser. No. 15/512,001, filed Sep. 16, 2015, Ser. No. 15/524,249, filed Nov. 3, 2015, Ser. No. 15/773,385, filed Nov. 3, 2016, and Ser. No. 15/756,386, filed on Aug. 25, 2016, all of which claim priority to and benefit of U.S. Provisional Application Ser. No. 62/211,660.

TECHNOLOGY FIELD

The present disclosure generally relates to compositions and methods for treatment of neurotrauma, which refers to injury to a peripheral or nerve, especially part of the central nervous system (the brain and/or spinal cord), and autoimmune disorders. The disclosure also relates to pre-implantation factor (PIF) mutants and methods of treatment using the same, including the treatment of neurotrauma and autoimmune disorders

BACKGROUND

Endogenous Pre-Implantation Factor (PIF) is a 15 amino acid peptide (MVRIKPGSANKPSDD—SEQ ID NO: 11) expressed by the embryo/fetus and placenta and is present in circulation of viable mammals throughout pregnancy starting post fertilization, playing a critical determining role to create and maternal tolerance without immune suppression. PIF exerts broad neurotrophic and neuroprotective effects. PIF regulates immunity, inflammation and transplant acceptance. By creating a favorable maternal milieu PIF specifically reduces neural damage while it promotes neural development, protecting against maternal adverse environment. PIF precisely targets proteins in the embryo to reduce oxidative stress and protein misfolding. In vivo PIF reduces spontaneous and LPS induced pregnancy loss by decreasing the pro-inflammatory response in the placenta. Consequently, PIF translation to use as a therapeutic drug in non-pregnant setting was and continues to be pursued.

It has been observed that PIF and synthetic PIF analogs (sPIF) have immune modulatory properties and such peptides are useful in the prevention and/or treatment of various immune-mediated diseases, including, but not limited to, autoimmune disorders, as well as various forms of neurotrauma, including, but not limited to, traumatic brain injury, spinal cord injury, and inflammation of the central nervous system (CNS) and/or peripheral nervous system (PNS). Compositions and methods for treating and/or preventing immune-mediated disorders and neurotrauma are provided herein.

SUMMARY

These observations concerning the ability of PIF and sPIF to modulate immune properties regulate inflammation and promote proper brain development correspond well to the medical needs of patients with trauma to the central nervous system. Compositions and methods for the treatment of patients with in need of treatment for are provided herein.

The present disclosure relates to a method of treating or preventing traumatic injury of the central nervous system in a subject in need thereof, the method comprising administering to the subject at least one pre-implantation factor (PIF) peptide, an analog thereof, or a pharmaceutically acceptable salt thereof.

In some embodiments, the step of administering to the subject at least one PIF peptide, an analog thereof, or a pharmaceutically acceptable salt thereof comprises administering a therapeutically effective dose of the at least one PIF molecule, an analog thereof, or a pharmaceutically acceptable salt thereof.

In some embodiments, the step of administering to the subject at least one PIF peptide, an analog thereof, or a pharmaceutically acceptable salt thereof comprises administering a therapeutically effective dose of the PIF peptide, an analog thereof, or pharmaceutically acceptable salt thereof from about 0.001 mg/kg to about 200 mg/kg.

In some embodiments, the step of administering to the subject at least one PIF peptide, an analog thereof, or a pharmaceutically acceptable salt thereof comprises administering a therapeutically effective dose of the PIF peptide, an analog thereof, or pharmaceutically acceptable salt thereof from about 0.5 mg/kg to about 5 mg/kg.

In some embodiments, the at least the PIF peptide, an analog thereof, or pharmaceutically acceptable salt thereof comprises a chemical targeting moiety and/or a radioactive moiety.

In some embodiments, the at least one inhibitor of nuclear translocation of beta-catenin or pharmaceutically acceptable salt thereof comprises at least one radioactive moiety comprising at least one or a combination of the following isotopes: $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$.

In some embodiments, the method further comprises administering at least one analgesic and/or one anti-inflammatory compound.

In some embodiments, the method further comprises administering at least one analgesic and or one anti-inflammatory compound before, after, or simultaneously with the administration of a therapeutically effective dose of at least one PIF peptide, an analog thereof or pharmaceutically acceptable salt thereof.

In some embodiments, the traumatic injury to the central nervous system comprises a concussion.

In some embodiments, the therapeutically effective dose is from about 1.0 mg/kg to about 5.5 mg/kg, wherein kg is kilograms of the subject and mg is milligrams of the therapeutically effective dose.

In some embodiments, the PIF peptide comprises SEQ ID NO:1, SEQ ID NO:2, and/or SEQ ID NO:3. In some embodiments, the PIF peptide comprises SEQ ID NO:10 or a pharmaceutically acceptable salt thereof. In some embodiments, the PIF peptide comprises SEQ ID NO:5 or a pharmaceutically acceptable salt thereof. In some embodiments, the PIF peptide comprises SEQ ID NO:6 or a pharmaceutically acceptable salt thereof. In some embodiments, the PIF peptide comprises SEQ ID NO:7 or a pharmaceutically acceptable salt thereof. In some embodiments, the PIF peptide comprises SEQ ID NO:8 or a pharmaceutically acceptable salt thereof. In some embodiments, the PIF peptide comprises SEQ ID NO:9 or a pharmaceutically acceptable salt thereof.

The present disclosure also relates to a method of treating or preventing traumatic brain injury in a subject in need thereof, the method comprising administering to the subject at least one pharmaceutical composition comprising: pre-implantation factor (PIF) peptide, an analog thereof, or a pharmaceutically acceptable salt thereof; and a pharmaceutically acceptable carrier.

In some embodiments, the pharmaceutically acceptable carrier is sterile and pyrogen-free water.

In some embodiments, the therapeutically effective dose is about 1.0 mg/kg, wherein kg is kilograms of the subject and mg is milligrams of the therapeutically effective dose. In some embodiments, the therapeutically effective dose is about 2.0 mg/kg, wherein kg is kilograms of the subject and mg is milligrams of the therapeutically effective dose. In some embodiments, the therapeutically effective dose is about 3.0 mg/kg, wherein kg is kilograms of the subject and mg is milligrams of the therapeutically effective dose. In some embodiments, the therapeutically effective dose is about 4.0 mg/kg, wherein kg is kilograms of the subject and mg is milligrams of the therapeutically effective dose. In some embodiments, the therapeutically effective dose is about 0.2 mg/kg, wherein kg is kilograms of the subject and mg is milligrams of the therapeutically effective dose. In some embodiments, the therapeutically effective dose is about 0.3 mg/kg, wherein kg is kilograms of the subject and mg is milligrams of the therapeutically effective dose. In some embodiments, the therapeutically effective dose is about 0.4 mg/kg, wherein kg is kilograms of the subject and mg is milligrams of the therapeutically effective dose. In some embodiments, the therapeutically effective dose is about 0.5 mg/kg, wherein kg is kilograms of the subject and mg is milligrams of the therapeutically effective dose. In some embodiments, the therapeutically effective dose is about 0.6 mg/kg, wherein kg is kilograms of the subject and mg is milligrams of the therapeutically effective dose. In some embodiments, the therapeutically effective dose is about 0.7 mg/kg, wherein kg is kilograms of the subject and mg is milligrams of the therapeutically effective dose. In some embodiments, the therapeutically effective dose is about 0.8 mg/kg, wherein kg is kilograms of the subject and mg is milligrams of the therapeutically effective dose.

The present disclosure also relates to a pharmaceutical composition comprising (i) a therapeutically effective dose of one or a combination of PIF peptide or analogs thereof or pharmaceutically acceptable salts thereof; and (ii) a pharmaceutically acceptable carrier.

In some embodiments, the pharmaceutically acceptable carrier is sterile and pyrogen-free water or Lactated Ringer's solution.

In some embodiments, the composition further comprises a therapeutically effective dose of one or a plurality of active agents.

In some embodiments, the one or plurality of active agents is one or a combination of compounds chosen from: an anti-inflammatory compound, alpha-adrenergic agonist, antiarrhythmic compound, analgesic compound, and an anesthetic compound.

In some embodiments, the therapeutically effective dose of one or a combination of PIF peptide or analogs thereof or pharmaceutically acceptable salts thereof is about 1.0 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 2.0 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 3.0 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 4.0 mg/kg, wherein kg is kilograms of the subject and mg is milligrams of the therapeutically effective dose.

In some embodiments, wherein the therapeutically effective dose of one or a combination of PIF peptide or analogs thereof or pharmaceutically acceptable salts thereof is about 0.2 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.3 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.4 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.5 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.6 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.7 mg/kg, wherein kg is kilograms of the subject and mg is milligrams of the therapeutically effective dose.

In some embodiments, wherein the therapeutically effective dose of one or a combination of PIF peptide or analogs thereof or pharmaceutically acceptable salts thereof is about 0.8 mg/kg, wherein kg is kilograms of the subject and mg is milligrams of the therapeutically effective dose.

In some embodiments, the therapeutically effective dose of one or a combination of PIF peptide or analogs thereof or pharmaceutically acceptable salts thereof is about 0.9 mg/kg, wherein kg is kilograms of the subject and mg is milligrams of the therapeutically effective dose.

In some embodiments, the composition further comprises one or a plurality of stem cells.

In some embodiments, the stem cell is an autologous stem cell.

The present disclosure also relates to a method of treating or preventing bronchopulmonary dysplasia in a subject in need thereof, the method comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to a method of treating or preventing peripheral nerve injury in a subject in need thereof, the method comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to method of treating or preventing Gaucher's disease in a subject in need thereof, the method comprising administering to the subject at least one pharmaceutical composition comprising: pre-implantation factor (PIF) peptide, an analog thereof, or a pharmaceutically acceptable salt thereof; and a pharmaceutically acceptable carrier.

In some embodiments, the pharmaceutical composition is administered via parenteral injection, subcutaneous injection, intravenous injection, intramuscular injection, intraperitoneal injection, transdermally, orally, buccally, ocular routes, intravaginally, by inhalation, by depot injections, or by implants.

In some embodiments, the compositions further comprise one or a combination of active agents chosen from: an anti-inflammatory compound, alpha-adrenergic agonist, antiarrhythmic compound, analgesic compound, and an anesthetic compound.

In some embodiments, the one or combination of active agents is selected from Table Y.

The present disclosure also relates to a method of preserving microglial cell function comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to a method of treating or preventing vascular inflammation simultaneously with preserving microglial cell function comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to a method of improving the clinical outcome in a subject suffering with, diagnosed with or suspected of having peripheral or CNS neurotrauma comprising administering to the subject at least one pharmaceutical composition comprising: pre-implantation factor (PIF) peptide, an analog thereof, or a pharmaceutically acceptable salt thereof; and a pharmaceutically acceptable carrier.

The present disclosure also relates to a method of treating or preventing *Listeria monocytogenes* infection, malaria, Lyme disease, cardiovascular disease, duodenal peptic ulcer, atherosclerosis, peritonitis or tuberculosis in a subject in need thereof, the method comprising administering to the subject at least one pharmaceutical composition comprising:

a therapeutically effective amount of a PIF analog, or a pharmaceutically acceptable salt thereof; and a pharmaceutically acceptable carrier.

BRIEF DESCRIPTION OF THE DRAWINGS

FIG. 5A depicts sPIF treatment that resulted in neuronal rescue. FIG. 5B depicts sPIF treatment that resulted in reduced microglial activation in neuronal and microglial cells. FIG. 5C depicts sPIF co-localization in neuronal and microglial cells in vivo. FIG. 5D depicts sPIF reduction of let-7 levels Akt dependent in vivo. FIG. 5E depicts sPIF reduction of let-7 levels in the brain. FIG. 5F depicts sPIF induced reduction of apoptosis and promotion of neuroprotection in vivo. FIG. 5G depicts a diagram of proposed sPIF mediated molecular pathways.

DETAILED DESCRIPTION OF THE DISCLOSURE

Figure 1:
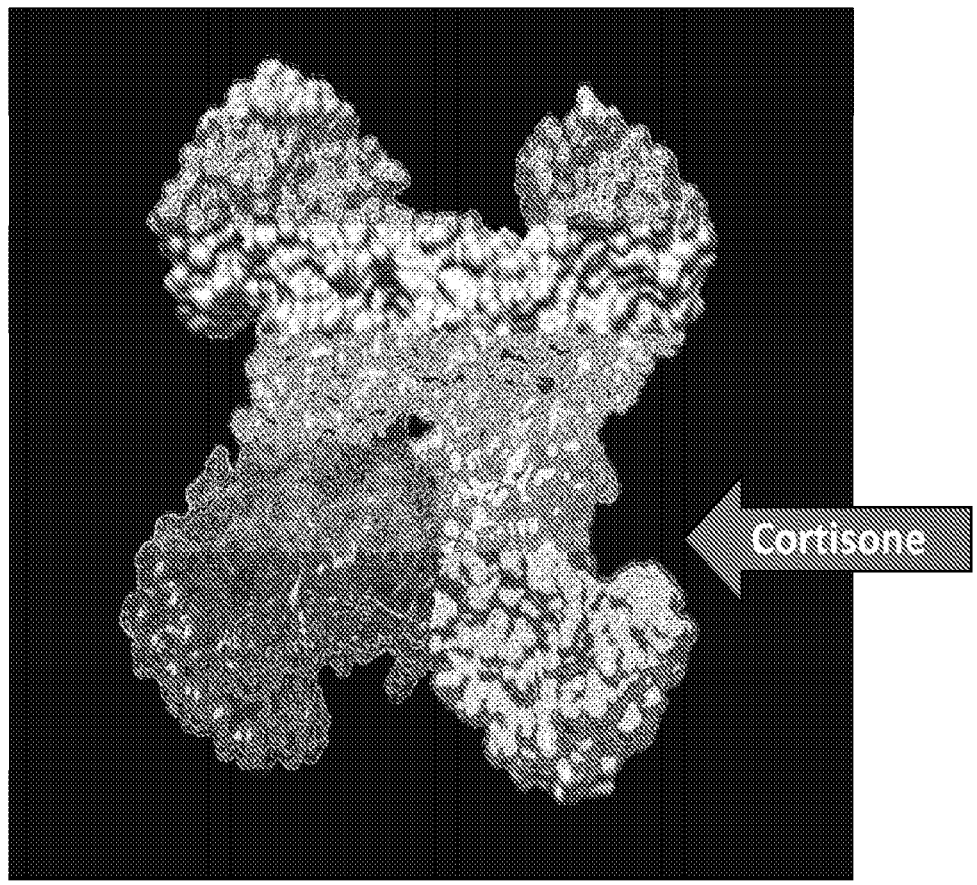
FIG. 1 depicts a crystal structure of PIF binding to the cortisone receptor at the cortisone-binding site. While PIF modulates the immune response, the protein also competes with cortisone.

Before the present compositions and methods are described, it is to be understood that this disclosure is not limited to the particular molecules, compositions, methodologies or protocols described, as these may vary. It is also to be understood that the terminology used in the description is for the purpose of describing the particular versions or embodiments only, and is not intended to limit the scope of the present disclosure which will be limited only by the appended claims. It is understood that these embodiments are not limited to the particular methodology, protocols, cell lines, vectors, and reagents described, as these may vary. It also is to be understood that the terminology used herein is for the purpose of describing particular embodiments only, and is not intended to limit the scope of the present embodiments or claims. The compositions described herein may include D amino acids, L amino acids, a racemic backbone of D and L amino acids, or any mixture thereof at each residue. That is, at each position, the residue may be a D amino acid residue or a L-amino acid residue and each position can be independently D or L of each other position, unless context dictates otherwise.

Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the preferred methods, devices, and materials are now described. All publications mentioned herein are incorporated by reference. Nothing herein is to be construed as an admission that the disclosure is not entitled to antedate such disclosure by virtue of prior disclosure.

As used herein, the phrase "in need thereof" means that the animal or mammal has been identified or suspected as having a need for the particular method or treatment. In some embodiments, the identification can be by any means of diagnosis or observation. In any of the methods and treatments described herein, the animal or mammal can be in need thereof. In some embodiments, the animal or mammal is in an environment or will be traveling to an environment in which a particular disorder or condition is prevalent or more likely to occur.

As used herein, the term "subject," "individual" or "patient," used interchangeably, means any animal, including mammals, such as mice, rats, other rodents, rabbits, dogs, cats, swine, cattle, sheep, horses, or primates, such as humans.

As used herein, the terms "a" or "an" means that "at least one" or "one or more" unless the context clearly indicates otherwise. It must also be noted that as used herein and in the appended claims, the singular forms "a", "an", and "the" include plural reference unless the context clearly dictates otherwise. Thus, for example, reference to "a cell" is a reference to one or more cells and equivalents thereof known to those skilled in the art, and so forth.

As used herein, the term "about" means that the numerical value is approximate and small variations would not significantly affect the practice of the disclosed embodiments. Where a numerical limitation is used, unless indicated otherwise by the context, "about" means the numerical value can vary by 10% and remain within the scope of the disclosed embodiments. Where a numerical value is used with the term "about" the numerical value without the term "about" is also disclosed and can be used without the term "about."

As used herein, the term "animal" includes, but is not limited to, humans and non-human vertebrates such as wild animals, rodents, such as rats, ferrets, and domesticated animals, and farm animals, such as horses, pigs, cows, sheep, goats. In some embodiments, the animal is a mammal. In some embodiments, the animal is a human. In some embodiments, the animal is a non-human mammal.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the phrase "integer from X to Y" means any integer that includes the endpoints. That is, where a range is disclosed, each integer in the range including the endpoints is disclosed. For example, the phrase "integer from X to Y" discloses about 1, 2, 3, 4, or 5 as well as the range from about 1 to about 5.

As used herein, the term "mammal" means any animal in the class Mammalia such as rodent (i.e., a mouse, a rat, or a guinea pig), a monkey, a cat, a dog, a cow, a horse, a pig, or a human. In some embodiments, the mammal is a human.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" can refer to therapeutic treatment and/or prophylactic or preventative measures wherein the object is to prevent or slow down (lessen) an undesired physiological condition, disorder or disease, or obtain beneficial or desired clinical results. For purposes of the embodiments described herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment can also include eliciting a clinically significant response without excessive levels of side effects. Treatment also includes prolonging survival as compared to expected survival if not receiving treatment. Thus, "treatment of a traumatic brain injury" means an activity that prevents, alleviates or ameliorates any of the primary phenomena or secondary symptoms associated with the traumatic brain injury.

This application describes compounds and methods of administering those compounds to a subject in need thereof. In some embodiments, "preimplantation factor" or "PIF" may also refer to synthetic PIF-1, which replicates the native peptide's effect and exerts potent immune modulatory effects on activated peripheral blood mononuclear cell (PBMC) proliferation and cytokine secretion, acting through novel sites on PBMCs and having an effect which is distinct from known immunosuppressive drugs. In some embodiments, "preimplantation factor" or "PIF" or "PIF analog" refers to an amino acid selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or peptidomimetics thereof, and combinations thereof that are about 75, 80, 81, 82, 83, 84 85, 86, 87, 88, 89, 90, 91, 92, 93, 94, 95, 96, 97, 98, or 99% homologous to any such amino acid.

Without being bound by any particular theory, the compounds described herein may act as agonists of PIF-mediated signal transduction via the receptor or receptors of PIF. Thus, these compounds modulate signaling pathways that provide significant therapeutic benefit in the treatment of, but not limited to, traumatic brain injury, such as concussion, and BPD. The compounds of the present disclosure may exist in unsolvated forms as well as solvated forms, including hydrated forms. The compounds of the present disclosure also are capable of forming both pharmaceutically acceptable salts, including but not limited to acid addition and/or base addition salts. Furthermore, compounds of the present disclosure may exist in various solid states including an amorphous form (non-crystalline form), and in the form of clathrates, prodrugs, polymorphs, bio-hydrolyzable esters, racemic mixtures, non-racemic mixtures, or as purified stereoisomers including, but not limited to, optically pure enantiomers and diastereomers. In general, all of these forms can be used as an alternative form to the free base or free acid forms of the compounds, as described above and are intended to be encompassed within the scope of the present disclosure.

A "polymorph" refers to solid crystalline forms of a compound. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Different physical properties of polymorphs can affect their processing. The disclosure relates to a polymorph of any of the disclosed PIF peptides.

As noted above, the compounds of the present disclosure can be administered, inter alia, as pharmaceutically acceptable salts, esters, amides or prodrugs. The term "salts" refers to inorganic and organic salts of compounds of the present disclosure. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977). The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Salts include those formed from hydrochloric, hydrobromic, sulphuric, phosphoric, citric, tartaric, lactic, pyruvic, acetic, succinic, fumaric, maleic, methanesulphonic and benzenesulphonic acids.

In some embodiments, salts of the compositions comprising either a PIF or PIF analog or PIF mutant may be formed by reacting the free base, or a salt, enantiomer or racemate thereof, with one or more equivalents of the appropriate acid. In some embodiments, pharmaceutical acceptable salts of the present disclosure refer to analogs having at least one basic group or at least one basic radical. In some embodiments, pharmaceutical acceptable salts of the present disclosure comprise a free amino group, a free guanidino group, a pyrazinyl radical, or a pyridyl radical that forms acid addition salts. In some embodiments, the pharmaceutical acceptable salts of the present disclosure refer to analogs that are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin. In some embodiments, the salts may be those that are physiologically tolerated by a patient. Salts according to the present disclosure may be found in their anhydrous form or as in hydrated crystalline form (i.e., complexed or crystallized with one or more molecules of water).

Examples of pharmaceutically acceptable esters of the compounds of the present disclosure include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present disclosure may be prepared according to methods that are well known in the art. Examples of pharmaceutically acceptable amides of the compounds of the present disclosure include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present disclosure may be prepared according to methods well known to those skilled in the art.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with PIF, can include, but is not limited to, providing PIF peptide into or onto the target tissue; providing PIF peptide systemically to a patient by, e.g., intravenous injection whereby the therapeutic reaches the target; providing PIF peptide in the form of the encoding sequence thereof to the target (e.g., by so-called gene-therapy techniques). "Administering" a composition may be accomplished by parenteral, oral or topical administration.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal without the production of undesirable physiological effects such as nausea, dizziness, rash, or gastric upset. In a preferred embodiment, the therapeutic composition is not immunogenic when administered to a subject for therapeutic purposes.

As used herein, the term "therapeutic" means an agent utilized to treat, combat, ameliorate, prevent or improve an unwanted condition or disease of a subject. In part, embodiments of the present disclosure are directed to treating, ameloriating, preventing or improving autoimmune disease.

A "therapeutically effective amount" or "effective amount" or "physiologically relevant amount" of a composition is an amount calculated to achieve a desired effect, i.e., to effectively inhibit or reduce symptoms and/or complications associated with traumatic brain injury. Effective amounts of compounds of the present disclosure can objectively or subjectively reduce or decrease the severity or frequency of symptoms associated with traumatic brain injury, such as concussion. The specific dose of a compound administered according to this disclosure to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from about 0.01 mg/kg to about 100 mg/kg, more preferably about 0.1 mg/kg to about 1 mg/kg. In some embodiments, the therapeutically effective dose of PIF or PIF analog or peptide is about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, and 1 mg/kg, where "mg" is milligram of PIF analog or peptide "kg" is kilogram of the subject.

In some embodiments, the pharmaceutical compositions comprise a therapeutically effective amount of PIF peptide or analog but the composition is free of SEQ ID NO:11 or a pharmaceutically acceptable salt thereof.

It will be understood that the effective amount administered will be determined by the physician in the light of the relevant circumstances including the condition to be treated, the choice of compound to be administered, and the chosen route of administration, and therefore the above dosage ranges are not intended to limit the scope of the disclosure in any way. A therapeutically effective amount of compound of this disclosure is typically an amount such that when it is administered in a physiologically tolerable excipient composition, it is sufficient to achieve an effective systemic concentration or local concentration in the tissue. In some embodiments, the term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a co-therapy.

As used herein, "central nervous system" or CNS refers to the part of the nervous system consisting of the brain and the spinal cord. The brain is encased in the skill and protected by the cranium. The spinal cord is continuous with and lies caudally to the brain, and is protected by the vertebra. The spinal cord reaches from the base of the skull, continues through or starting below the foramen magnum, and terminates roughly level with the first or second lumbar vertebra. Arguably, the retina, the optic nerve, the olfactory epithelium, and the olfactory nerves are a part of the CNS, as they synapse directly on to brain tissue without intermediate ganglia. In contrast, the "peripheral nervous system" or PNS is the part of the nervous system that consists of the nerves and ganglia outside the brain spinal cord. The PNS connects the CNS to the limbs and organs of the body, serving as a communication relay. Unlike the CNS, the PNS is not protected by the bones of the vertebra or skull, which leaves it exposed to toxins and mechanical injuries.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein.

Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21st ed., 2005)).

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

"Traumatic Brain Injury", also known as the acronym TBI or intracranial injury, refers to a traumatic injury to the brain from an external force. TBI can be classified based on severity, mechanism (i.e. closed or penetrating), or location. TBI is a major cause of death and disability, especially in children and young adults. Causes of TBI include, but are not limited to, falls, vehicle accidence, and violence. Brain trauma can occur as a consequence of a focal impact upon the cranium, by a sudden acceleration/deceleration within the cranium, or by a complex combination of both movement and sudden impact. Damage caused by TBI includes primary injury (damaged cause at the moment of injury) and secondary injury (a variety of events that take place in the time following the injury). Secondary injury process include, but are not limited to, alterations in cerebral blood flow and pressure within the skull. TBI can cause a host of physical, cognitive, social, emotional, and behavioral effects. TBI outcome can range from complete recovery to permanent disability or death. The force may be internal or external. For example, a traumatic brain injury can result when the head suddenly and violently hits an object, or when an object pierces the skull and enters brain tissue. Symptoms of a traumatic brain injury can be mild, moderate, or severe, depending on the extent of the damage to the brain.

"Spinal Cord Injury", also known as the acronym SCI, refers to an injury to the spinal cord resulting in a change, either temporary or permanent, in the cord's normal motor, sensory, or autonomic function. Common causes of damage are trauma (car accident, gunshot, falls, sports injuries, etc.) or disease (transverse myelitis, polio, spina bifida, Friedreich's ataxia, etc.). The spinal cord does not have to be severed in order for a loss of function to occur. Depending on where the spinal cord and nerve roots are damaged, the symptoms can vary widely, from pain to paralysis to incontinence. Spinal cord injuries are described at various levels of "incomplete", which can vary from having no effect on the patient to a "complete" injury which means a total loss of function. Treatment of spinal cord injuries starts with restraining the spine and controlling inflammation to prevent further damage. The actual treatment can vary widely depending on the location and extent of the injury. In many cases, spinal cord injuries require substantial physical therapy and rehabilitation, especially if the patient's injury interferes with activities of daily life. Research into treatments for spinal cord injuries includes controlled hypothermia and stem cells, though many treatments have not been studied thoroughly and very little new research has been implemented in standard care.

The term "concussion" as used herein refers to a type of traumatic brain injury that is caused by a direct or indirect mechanism, for example a direct blow to the head, face or neck or a blow elsewhere on the body with an "impulsive" force transmitted to the head. A concussion is characterized by an immediate and transient alteration in brain function, including alteration of mental status and level of consciousness. Diagnosis of concussion includes one or more of the following clinical domains. Symptoms include (a) somatic (e.g. Headache), cognitive (e.g. Feeling like in a fog, dullness) and/or emotional symptoms (e.g. lability, depression) (b) physical signs (e.g. loss of consciousness, amnesia, convulsions), (c) behavioral changes (e.g. irritability), (d) cognitive impairment (e.g. slowed reaction times), (e) sleep disturbance (e.g. drowsiness). Sequelae of concussion include recurrent concussion, migraine headaches, depression, Parkinson's disease, Alzheimer's disease, attention deficit hyperactivity disorder, learning disability, sleep disorders, neurotransmitter production disturbance (e.g. dopamine, serotonin, acetylcholine, GABA).

"Disease" or "disorder" refers to an impairment of the normal function of an organism. As used herein, a disease may be characterized by the levels of primary or secondary injury causing the impairment of normal function.

"Immune-modulating" refers to the ability of a compound of the present disclosure to alter (modulate) one or more aspects of the immune system. The immune system functions to protect the organism from infection and from foreign antigens by cellular and humoral mechanisms involving lymphocytes, macrophages, and other antigen-presenting cells that regulate each other by means of multiple cell-cell interactions and by elaborating soluble factors, including lymphokines and antibodies, that have autocrine, paracrine, and endocrine effects on immune cells.

"Auto-immune disease" refers to various diseases that arise from an abnormal immune response of the body against substances and tissues normally present in the body. This may be restricted to certain organs or involve a particular tissue in different places. A large number of auto-immune diseases are recognized, including, but not limited to, Hashimoto's thyroiditis, pernicious anemia, Addison's disease, type I (insulin dependent) diabetes, rheumatoid arthritis, systemic lupus erythematosus, dermatomyositis, Sjogren's syndrome, lupus erythematosus, multiple sclerosis, myasthenia gravis, Reiter's syndrome, and Grave's disease, alopecia greata, anklosing spondylitis, antiphospholipid syndrome, auto-immune hemolytic anemia, auto-immune hepatitis, auto-immune inner ear disease, auto-immune lymphoproliferative syndrome (ALPS), auto-immune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, CREST syndrome, Crohn's disease, Dego's disease, dermatomyositis, dermatomyositis, discoid lupus, essential mixed cryoglobulinemia, fibromyalgia-fibromyositis, Guillain-Barre syndrome, idiopathic pulmonary fibrosis, idiopathic thrombocytopenia purpura (ITP), IgA nephropathy, juvenile arthritis, Meniere's disease, mixed connective tissue disease, pemphigus vulgaris, polyarteritis nodosa, polychondritis, polyglancular syndromes, polymyalgia rheumatica, polymyositis, primary agammaglobulinemia, primary biliary cirrhosis, psoriasis, Raynaud's phenomenon, rheumatic fever, sarcoidosis, scleroderma, stiff-man syndrome, Takayasu arteritis, temporal arteritis/giant cell arteritis, ulcerative colitis, uveitis, vasculitis, vitiligo, and Wegener's granulomatosis.

"Asthma" refers to a chronic inflammatory disorder affecting the bronchial tubes, usually triggered or aggravated by allergens or contaminants. Asthma is characterized by constriction of the bronchial tubes, producing symptoms including, but not limited to, cough, shortness of breath, wheezing, excess production of mucus, and chest constriction "Atopy" refers to the tendency to develop so-called "classic" allergic diseases such as atopic dermatitis, allergic rhinitis (hay fever), and asthma, and is associated with a capacity to produce an immunoglobulin E (IgE) response to common allergens. Atopy is often characterized by skin allergies including but not limited to eczema, urticaria, and atopic dermatitis. Atopy can be caused or aggravated by inhaled allergens, food allergens, and skin contact with allergens, but an atopic allergic reaction, may occur in areas of the body other than where contact with the allergan occurred. A strong genetic (inherited) component of atop is suggested by the observation that the majority of atopic dermatitis patients have at least one relative who suffers from eczema, asthma, or hay fever.

"Pollinosis," "hay fever," or "allergic rhinitis," are terms that refer to an allergy characterized by sneezing, itchy and watery eyes, a runny nose and a burning sensation of the palate and throat. Others seasonal, pollinosis is usually caused by allergies to airborne substances such as pollen, and the disease can sometimes be aggravated in an individual by exposure to other allergens to which the individual is allergic.

"Collagen disease" or "connective tissue disease" refers to systemic diseases associated with defects in collagen, a major component of the connective tissue. In some embodiments, collagen diseases are forms of auto-immune diseases. Types of collagen diseases include, but are not limited to, lupus erythematosus, Sjogren's syndrome, scleroderma, dermatomyositis, and polyarteritis nodosa.

"Inflammatory response" or "inflammation" is a general term for the local accumulation of fluid, plasma proteins, and white blood cells initiated by physical injury, infection, or a local immune response. Inflammation is an aspect of many diseases and disorders, including but not limited to diseases related to immune disorders, viral infection, arthritis, autoimmune diseases, collagen diseases, allergy, asthma, pollinosis, and atopy. Inflammation is characterized by rubor (redness), dolor (pain), calor (heat) and tumor (swelling), reflecting changes in local blood vessels leading to increased local blood flow which causes heat and redness, migration of leukocytes into surrounding tissues (extravasation), and the exit of fluid and proteins from the blood and their local accumulation in the inflamed tissue, which results in swelling and pain, as well as the accumulation of plasma proteins that aid in host defense. These changes are initiated by cytokines produced by activated macrophages. Inflammation is often accompanied by loss of function due to replacement of parenchymal tissue with damaged tissue (e.g., in damaged myocardium), reflexive disuse due to pain, and mechanical constraints on function, e.g., when a joint swells during acute inflammation, or when scar tissue bridging an inflamed joint contracts as it matures into a chronic inflammatory lesion.

"Anti-inflammatory" define Regulation of inflammation not only anti-inflammatory refers to the ability of a compound to prevent or reduce the inflammatory response, or to soothe inflammation by reducing the symptoms of inflammation such as redness, pain, heat, or swelling. Inflammatory responses can be triggered by injury, for example injury to skin, muscle, tendons, or nerves. Inflammatory responses can also be triggered as part of an immune response. Inflammatory responses can also be triggered by infection, where pathogen recognition and tissue damage can initiate an inflammatory response at the site of infection. Generally, infectious agents induce inflammatory responses by activating innate immunity. Inflammation combats infection by delivering additional effector molecules and cells to augment the killing of invading microorganisms by the front-line macrophages, by providing a physical barrier preventing the spread of infection, and by promoting repair of injured tissue. "Inflammatory disorder" is sometimes used to refer to chronic inflammation due to any cause.

Inflammation triggered by various kinds of injuries to muscles, tendons or nerves caused by repetitive movement of a part of the body are generally referred to as repetitive strain injury (RSI). Diseases characterized by inflammation triggered by RSI include, but are not limited to, bursitis, carpal tunnel syndrome, Dupuytren's contracture, epicondylitis (e.g. "tennis elbow"), "ganglion" (inflammation in a cyst that has formed in a tendon sheath, usually occurring on the wrist) rotator cuff syndrome, tendinitis (e.g., inflammation of the Achilles tendon), tenosynovitis, and "trigger finger" (inflammation of the tendon sheaths of fingers or thumb accompanied by tendon swelling).

"Bronchopulmonary dysplasia", also known as BPD or chronic lung disease of infancy, is a chronic lung disorder that develops in patients who receive prolonged mechanical ventilation of high oxygen delivery. Such prolonged delivery, especially in premature infants, causes necrotizing bronchiolitis and alveolar septal injury with inflammation and scarring. Mild cases of BPD can have uniformly dilated acini with thin alveolar septa and little or no interstitial fibrosis. BPD and other inflammation disorders of the lungs can afflict patient requiring ventilation and oxygen delivery for treatment of other disorders, for example, traumatic brain injury or spinal cord injuries.

"Gaucher's disease" is s genetic disease in which glucosylceramide accumulate in cells and certain organs. The disorder is characterized by bruising, fatigue, anemia, low blood platelets, and enlargement of the liver and spleen. Gaucher's disease is the most common lysosomal storage diseases, and is caused by a hereditary deficiency of the enzyme glucorcerebrosidase. This enzyme acts on the glucolipid glucocerebroside. When the enzyme is defective, glucosylceramide accumulates, particularly in white blood cells. Manifestations may include enlarged spleen and liver, liver malfunction, skeletal disorders and bone lesions that may be painful, severe neurologic complications, swelling of lymph nodes and adjacent joints, distended abdomen, a brownish tint to the skin, anemia, low blood platelets, and yellow fatty deposits on the white of the eyes. The disease is caused by a recessive nutation in a gene located on chromosome 1 and affects both males and females.

It is understood that the terms "immune disorder" and "inflammatory response" are not exclusive. It is understood that many immune disorders include acute (short term) or chronic (long term) inflammation. It is also understood that inflammation can have immune aspects and non-immune aspects. The role(s) of immune and nonimmune cells in a particular inflammatory response may vary with the type of inflammatory response, and may vary during the course of an inflammatory response. Immune aspects of inflammation and diseases related to inflammation can involve both innate and adaptive immunity. Certain diseases related to inflammation represent an interplay of immune and nonimmune cell interactions, for example intestinal inflammation (Fiocchi et al., 1997 Am J Physiol Gastrointest Liver Physiol 273: G769-G775), pneumonia (lung inflammation), or glomerulonephritis.

It is further understood that many diseases are characterized by both an immune disorder and an inflammatory response, such that the use of discrete terms "immune disorder" or "inflammatory response" is not intended to limit the scope of use or activity of the compounds of the present invention with respect to treating a particular disease. For example, arthritis is considered an immune disorder characterized by inflammation of joints, but arthritis is likewise considered an inflammatory disorder characterized by immune attack on joint tissues. Thus, the observation that a compound of the invention reduces the inflammation seen in an animal model of arthritis, does not limit the observed activity of the compound to anti-inflammatory activity. In a disease having both immune and inflammatory aspects, merely measuring the effects of a compound of the present invention of inflammation does not exclude the possibility that the compound may also have immune-modulating activity in the same disease. Likewise, in a disease having both immune and inflammatory aspects, merely measuring the effects of a compound of the present invention on immune responses does not exclude the possibility that the compound may also have anti-inflammatory activity in the same disease.

As used herein, "conservative" amino acid substitutions may be defined as set out in Tables A, B, or C below. The PIF compounds of the disclosure include those wherein conservative substitutions (from either nucleic acid or amino acid sequences) have been introduced by modification of polynucleotides encoding polypeptides of the disclosure. Amino acids can be classified according to physical properties and contribution to secondary and tertiary protein structure. A conservative substitution is recognized in the art as a substitution of one amino acid for another amino acid that has similar properties. In some embodiments, the conservative substitution is recognized in the art as a substitution of one nucleic acid for another nucleic acid that has similar properties, or, when encoded, has similar binding affinities or. Exemplary conservative substitutions are set out in Table A.

TABLE A

| Conservative Substitutions I | |
|---|---|
| Side Chain Characteristics Aliphatic | Amino Acid |
| Non-polar | G A P I L V F |
| Polar - uncharged | C S T M N Q |
| Polar - charged | D E K R |
| Aromatic | H F W Y |
| Other | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | Amino Acid |
|---|---|
| Non-polar (hydrophobic) | |
| Aliphatic: | A L I V P |
| Aromatic: | F W Y |
| Sulfur-containing: | M |
| Borderline: | G Y |
| Uncharged-polar | |
| Hydroxyl: | S T Y |
| Amides: | N Q |
| Sulfhydryl: | C |
| Borderline: | G Y |
| Positively Charged (Basic): | K R H |
| Negatively Charged (Acidic): | D E |

Alternately, exemplary conservative substitutions are set out in Table C.

TABLE C

Conservative Substitutions III

| Original Residue | Exemplary Substitution |
|---|---|
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the inhibitors described herein are intended to include nucleic acids and, where the inhibitors include polypeptide, polypeptides bearing one or more insertions, deletions, or substitutions, or any combination thereof, of amino acid residues as well as modifications other than insertions, deletions, or substitutions of amino acid residues.

As used herein, the terms "peptide," "polypeptide" and "protein" are used interchangeably and refer to two or more amino acids covalently linked by an amide bond or non-amide equivalent. The peptides of the disclosure can be of any length. For example, the peptides can have from about two to about 100 or more residues, such as, 5 to 12, 12 to 15, 15 to 18, 18 to 25, 25 to 50, 50 to 75, 75 to 100, or more in length. Preferably, peptides are from about 2 to about 18 residues in length. The peptides of the disclosure also include 1- and d-isomers, and combinations of 1- and d-isomers. The peptides can include modifications typically associated with posttranslational processing of proteins, for example, cyclization (e.g., disulfide or amide bond), phosphorylation, glycosylation, carboxylation, ubiquitination, myristylation, or lipidation. In some embodiments, the compositions or pharmaceutical compositions of the disclosure relate to analogs of any PIF sequence set forth in Table 1 that share no less than about 70%, about 75%, about 79%, about 80%, about 85%, about 86%, about 87%, about 90%, about 93%, about 94% about 95%, about 96%, about 97%, about 98%, about 99% homology with any one or combination of PIF sequences set forth in Table 1. In some embodiments, PIF may refer to an amino acid sequence selected from SEQ ID NOs: 1, 2, 3, 4, 5, 6, 7, 8, 9, or 10, or a functional fragment thereof that is about 70%, 75%, 80%, 85%, 90%, 91%, 92%, 93%, 94%, 95%, 96%, 97%, 98%, or 99% homologous to any such amino acid sequence. In some embodiments, PIF may refer to an amino acid sequence comprising, consisting essentially of, or consisting of a sequence that is at least 70%, 75%, 80%, 85%, 86%, 87%, 90%, 91%, 92%, 93%, 94%, 95%, 96%, 97%, 98%, or 99% homologous to SEQ ID. NO: 1. In some embodiments, the PIF mutant comprises a sequence selected from: MVXIKPGSANKPSDD (SEQ ID NO: 13), MVXIKPGSANKPSD (SEQ ID NO: 14), MVXIKPGSANKPS (SEQ ID NO: 15), MVXIKPGSANKP (SEQ ID NO: 16), MVXIKPGSANK (SEQ ID NO: 17), MVXIKPGSAN (SEQ ID NO: 18), MVXIKPGSA (SEQ ID NO: 19), MVXIKPGS (SEQ ID NO: 20), MVXIKPG (SEQ ID NO: 21), MVXIK (SEQ ID NO: 22), MVXI (SEQ ID NO: 23), or MVX wherein X is a non-natural amino acid or a naturally occurring amino acid.

Peptides disclosed herein further include compounds having amino acid structural and functional analogs, for example, peptidomimetics having synthetic or non-natural amino acids (such as a norleucine) or amino acid analogues or non-natural side chains, so long as the mimetic shares one or more functions or activities of compounds of the disclosure. The compounds of the disclosure therefore include "mimetic" and "peptidomimetic" forms. As used herein, a "non-natural side chain" is a modified or synthetic chain of atoms joined by covalent bond to the α-carbon atom, β-carbon atom, or γ-carbon atom which does not make up the backbone of the polypeptide chain of amino acids. The peptide analogs may comprise one or a combination of non-natural amino-acids chosen from: norvaline, tert-butylglycine, phenylglycine, He, 7-azatryptophan, 4-fluorophenylalanine, N-methyl-methionine, N-methyl-valine, N-methyl-alanine, sarcosine, N-methyl-tert-butylglycine, N-methyl-leucine, N-methyl-phenylglycine, N-methyl-isoleucine, N-methyl-tryptophan, N-methyl-7-azatryptophan, N-methyl-phenylalanine, N-methyl-4-fluorophenyl alanine, N-methyl-threonine, N-methyl-tyrosine, N-methyl-valine, N-methyl-lysine, homocysteine, and Tyr; Xaa2 is absent, or an amino acid selected from the group consisting of Ala, D-Ala, N-methyl-alanine, Glu, N-methyl-glutamate, D-Glu, Gly, sarcosine, norleucine, Lys, D-Lys, Asn, D-Asn, D-Glu, Arg, D-Arg, Phe, D-Phe, N-methyl-phenylalanine, Gin, D-Gln, Asp, D-Asp, Ser, D-Ser, N-methyl-serine, Thr, D-Thr, N-methyl-threonine, D-Pro D-Leu, N-methyl-leucine, D-Ile, N-methyl-isoleucine, D-Val, N-methyl-valine, tert-butylglycine, D-tert-butylglycine, N-methyl-tert-butylglycine, Trp, D-Trp, N-methyl-tryptophan, D-Tyr, N-methyl-tyrosine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, aminoisobutyric acid, (5)-2-amino-3-(1H-tetrazol-5-yl)propanoic acid, Glu, Gly, N-methyl-glutamate, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, octylglycine, tranexamic acid, aminovaleric acid, and 2-(2-aminoethoxy)acetic acid. The natural side chain, or R group, of an alanine is a methyl group. In some embodiments, the non-natural side chain of the composition is a methyl group in which one or more of the hydrogen atoms is replaced by a deuterium atom. Non-natural side chains are disclosed in the art in the following publications: WO/2013/172954, WO2013123267, WO/2014/071241, WO/2014/138429, WO/2013/050615, WO/2013/050616, WO/2012/166559, US Application No. 20150094457, Ma, Z., and Hartman, M. C. (2012). In Vitro Selection of Unnatural Cyclic Peptide Libraries via mRNA Display. In J. A. Douthwaite & R. H. Jackson (Eds.), *Ribosome Display and Related Technologies: Methods and Protocols* (pp. 367-390). Springer New York., all of which are incorporated by reference in their entireties.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below. The term "analog" refers to any polypeptide comprising at least one α-amino acid and at least one non-native amino acid residue, wherein the polypeptide is structurally similar to a naturally occurring full-length PIF protein and shares the biochemical or biological activity of the naturally occurring full-length protein upon which the analog is based. In some embodiments, the compositions, pharmaceutical compositions and kits comprise a peptide or peptidomimeic sharing share no less than about 70%, about 75%, about 79%, about 80%, about 85%, about 86%, about 87%, about 90%, about 93%, about 94% about 95%, about 96%, about 97%, about 98%, about 99% homology with any one or combination of PIF sequences set forth in Table 1; and wherein one or a plurality of amino acid residues is a non-natural amino acid residue or an amino acid residue with a non-natural sidechain. In some embodiments, peptide or peptide mimetics are provided, wherein a loop is formed between two cysteine residues. In some embodiments, the peptidomimetic may have many similarities to natural peptides, such as: amino acid side chains that are not found among the known 20 proteinogenic amino acids, non-peptide-based linkers used to effect cyclization between the ends or internal portions of the molecule, substitutions of the amide bond hydrogen moiety by methyl groups (N-methylation) or other alkyl groups, replacement of a peptide bond with a chemical group or bond that is resistant to chemical or enzymatic treatments, N- and C-terminal modifications, and conjugation with a non-peptidic extension (such as polyethylene glycol, lipids, carbohydrates, nucleosides, nucleotides, nucleoside bases, various small molecules, or phosphate or sulfate groups). As used herein, the term "cyclic peptide mimetic" or "cyclic polypeptide mimetic" refers to a peptide mimetic that has as part of its structure one or more cyclic features such as a loop, bridging moiety, and/or an internal linkage. As used herein, the term "bridging moiety" refers to one or a series of bonded atoms that covalently link one or a plurality of amino acid side chains to one another within an amino acid sequence.

In some embodiments, peptide or peptide mimetics are provided, wherein the loop comprises a bridging moiety selected from the group consisting of:

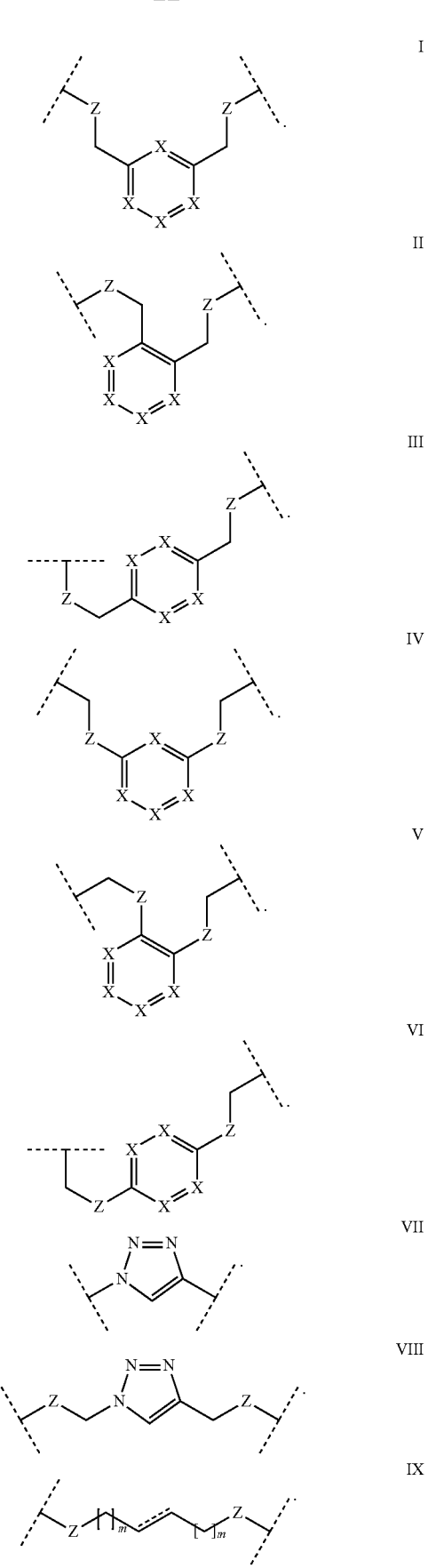

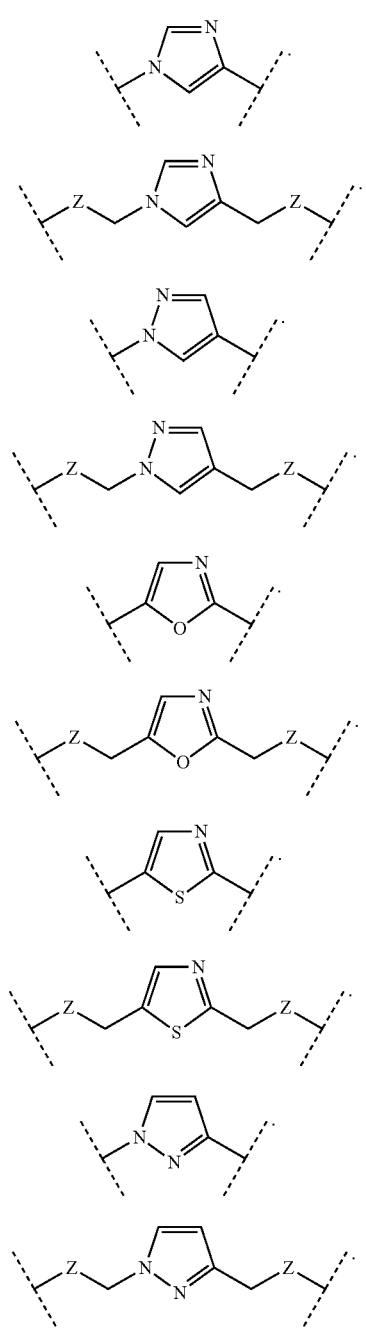

wherein each X is independently N or CH, such that no ring contains more than 2 N; each Z is independently a bond, NR, 0, S, CH2, C(O)NR, NRC(O), S(O)vNR, NRS(O)v; each m is independently selected from 0, 1, 2, and 3; each v is independently selected from 1 and 2; each R is independently selected from H and $C_1$-$C_6$; and each bridging moiety is connected to the peptide by independently selected $C_0$-$C_6$ spacers.

In some embodiments, the PIF peptides of the disclosure are modified to produce peptide mimetics by replacement of one or more naturally occurring side chains of the 20 genetically encoded amino acids (or D amino acids) with other side chains, for instance with groups such as alkyl, lower alkyl, cyclic 4-, 5-, 6-, to 7 membered alkyl, amide, amide lower alkyl, amide di (lower alkyl), lower alkoxy, hydroxy, carboxy and the lower ester derivatives thereof, and with 4-, 5-, 6-, to 7 membered heterocyclics. For example, proline analogs can be made in which the ring size of the proline residue is changed from 5 members to 4, 6, or 7 members. Cyclic groups can be saturated or unsaturated, and if unsaturated, can be aromatic or nonaromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

In a further embodiment a compound of the formula $R_1$-$R_2$-$R_3$-$R_4$-$R_5$-$R_6$-$R_7$-$R_8$-$R_9$-$R_{10}$-$R_{11}$-$R_{12}$-RD-$R_{14}$-$R_{15}$, wherein $R_1$ is Met or a mimetic of Met, $R_2$ is Val or a mimetic of Val, $R_3$ is Arg or a mimetic of Arg, or any amino acid, $R_4$ is Ile or a mimetic of Ile, $R_5$ is Lys or a mimetic of Lys, $R_6$ is Pro or a mimetic of Pro, $R_7$ is Gly or a mimetic of Gly, $R_8$ is Ser or a mimetic of Ser, $R_9$ is Ala or a mimetic of Ala, $R_{10}$ is Asn or a mimetic of Asn, $R_{11}$ is Lys or a mimetic of Lys, $R_{12}$ is Pro or a mimetic of Pro, $R_{13}$ is Ser or a mimetic of Ser, $R_{14}$ is Asp or a mimetic of Asp and $R_{15}$ is Asp or a mimetic of Asp is provided. In a further embodiment, a compound comprising the formula $R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$, wherein $R_1$ is a mimetic of the naturally occurring residue at position 1 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_2$ is a mimetic of the naturally occurring residue at position 2 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_3$ is a mimetic of the naturally occurring residue at position 3 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_4$ is a mimetic of the naturally occurring residue at position 4 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_5$ is a mimetic of the naturally occurring residue at position 5 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_6$ is a mimetic of the naturally occurring residue at position 6 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_7$ is a mimetic of the naturally occurring residue at position 7 of SEQ ID NO:1, SEQ ID NO:2, SEQ ID NO:3, SEQ ID NO:4, SEQ ID NO:6, SEQ ID NO:7, SEQ ID NO: 8, SEQ ID NO:9, or SEQ ID NO:10 or the residue at that position of such sequences; wherein $R_8$ is a mimetic of the naturally occurring residue at position 5 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_9$ is a mimetic of the naturally occurring residue at position 9 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_{10}$ is a mimetic of the naturally occurring residue at position 10 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_{11}$ is a mimetic of the naturally occurring residue at position 11 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_{12}$ is a mimetic of the naturally occurring residue at position 12 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_{13}$ is a mimetic of the naturally occurring residue at position 13 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_{14}$ is a mimetic of the naturally occurring residue at position 14 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences; wherein $R_{15}$ is a mimetic of the naturally occurring residue at position 15 of SEQ ID NO:1, SEQ ID NO:2, SEQ ID NO:3, SEQ ID NO:4, SEQ ID NO:5, SEQ ID NO:6, SEQ ID NO:7, SEQ ID NO: 8, SEQ ID NO:9, or SEQ ID NO:10 or the residue at that position of such sequences.

In some embodiments, the pharmaceutical composition comprising the formula $R_1$-$R_2$-$R_3$-$R_4$-$R_5$-$R_6$-$R_7$-$R_8$-$R_9$-$R_{10}$-$R_{11}$-$R_{12}$-RD-$R_{14}$-$R_{15}$-$R_{16}$-$R_{17}$-$R_{18}$, wherein $R_1$ is Ser or a mimetic of Ser, $R_2$ is Gly or a mimetic of Gly, $R_3$ is Ile or a mimetic of Ile, $R_4$ is Val or a mimetic of Val, $R_5$ is Ile or a mimetic of Ile, $R_6$ is Tyr or a mimetic of Tyr, $R_7$ is Gln or a mimetic of Gln, $R_8$ is Tyr or a mimetic of Tyr, $R_9$ is Met or a mimetic of Met, $R_{10}$ is Asp or a mimetic of Asp, $R_{11}$ is Asp or a mimetic of Asp, $R_{12}$ is Arg or a mimetic of Arg, $R_{13}$ is Tyr or a mimetic of Tyr, $R_{14}$ is Val or a mimetic of Val, $R_{15}$ is Gly or a mimetic of Gly, $R_{16}$ is Ser or a mimetic of Ser, $R_{17}$ is Asp or a mimetic of Asp and $R_{18}$ is Leu or a mimetic of Leu; and a compound comprising the formula $R_1$-$R_2$-$R_3$-$R_4$-$R_5$-$R_6$-$R_7$-$R_8$-$R_9$, wherein $R_1$ is Val or a mimetic of Val, $R_2$ is Ile or a mimetic of Ile, $R_3$ is Ile or a mimetic of Ile, $R_4$ is Ile or a mimetic of Ile, $R_5$ is Ala or a mimetic of Ala, $R_6$ is Gln or a mimetic of Gln, $R_7$ is Tyr or a mimetic of Tyr, $R_8$ is Met or a mimetic of Met, and $R_9$ is Asp or a mimetic of Asp is provided. In some embodiments, $R_3$ is not Arg or a mimetic of Arg.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, Ann. Rep. Med. Chem. 24,243-252, 1989). Certain peptidomimetic compounds are based upon the amino acid sequence of the peptides of the disclosure. Often, peptidomimetic compounds are synthetic compounds having a three dimensional structure (i.e. a "peptide motif") based upon the three-dimensional structure of a selected peptide. The peptide motif provides the peptidomimetic compound with the desired biological activity, i.e., binding to PIF receptors, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life.

Peptidomimetic design strategies are readily available in the art (see, e.g., Ripka & Rich, Curr. Op. Chern. Bioi. 2,441-452, 1998; Hruby et al., Curr. Op.Chem. Bioi. 1,114-119, 1997; Hruby & Baise, Curr. Med. Chern. 9,945-970, 2000). One class of peptidomimetics a backbone that is partially or completely non-peptide, but mimics the peptide backbone atom—for atom and comprises side groups that likewise mimic the functionality of the side groups of the native amino acid residues. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra).

A list of PIF peptides are provided below in Table 1. Antibodies to various PIF peptides and scrambled PIF peptides are also provided.

TABLE 1

| PIF Peptides | | |
|---|---|---|
| (SEQ ID NO) | Peptide | Amino Acid Sequence |
| SEQ ID NO: 1 | PIF (-3) | MVXIKPGSANKPSDD |
| SEQ ID NO: 2 | PIF (-1) | XVRIKPGSANKPSDD |
| SEQ ID NO: 3 | PIF (-1, -3) | XVXIKPGSANKPSDD |
| SEQ ID NO: 4 | PIF (-6) | MVRIKXGSANKPSDD |
| SEQ ID NO: 5 | PIF (-4) | MVRXKPGSANKPSDD |
| SEQ ID NO: 6 | PIF (-2) | MXRIKPGSANKPSDD |
| SEQ ID NO: 7 | mut1 | MVRIKEGSANKPSDD |
| SEQ ID NO: 8 | mut3 | MVRGKPGSANKPSDD |
| SEQ ID NO: 9 | mut4 | MERIKPGSANKPSDD |
| SEQ ID NO: 10 | mut5 | AVRIKPGSANKPSDD | n = native,
mut = mutant,
same AA, ( ) = position of AA,
X = any amino acid, except arginine In some embodiments of the present disclosure, a PIF peptide (or analog) is provided. In some embodiments, the PIF analog binds or associates with human insulin degrading enzyme (IDE—SEQ ID NO:12) at least 1%, 2%, 3%, 4%, 5%, 6%, 7%, 8%, 9%, or 10% or higher than native or wild-type PIF sequences. In some embodiments, the PIF analog may have a binding affinity for insulin degrading enzyme (IDE) that has at least 1%, 2%, 3%, 4%, 5%, 6%, 7%, 8%, 9%, or 10% or higher than native or wild-type PIF sequences. In some embodiments, the PIF analog may have a binding affinity for insulin degrading enzyme that has from about 1% to about 30% or higher than the affinity native or wild-type PIF sequences have for IDE. In some embodiments, the PIF analog may have a binding affinity for insulin degrading enzyme that has from about 1% to about 10% or higher than the affinity native or wild-type PIF sequences have for IDE In some embodiments, the PIF analog may have a binding affinity for insulin degrading enzyme that has from about 1% to about 20% or higher than the affinity native or wild-type PIF sequences have for IDE. In some embodiments, the PIF analog may have a binding affinity for insulin degrading enzyme that has from about 10% to about 20% or higher than the affinity native or wild-type PIF sequences have for IDE. Such PIF peptides in therapeutically effective amounts may be useful for treating any of the diseases or disorder disclosed herein.

In another embodiment, a pharmaceutical composition comprising a PIF peptide is provided. In preferred embodiments, the pharmaceutical composition comprises a therapeutically effective amount of a PIF peptide or a pharmaceutically acceptable salt thereof.

In another embodiment, a method of treating TBI is provided. In a preferred embodiment, the method comprises administering an effective amount of a PIF peptide to a subject in need thereof.

In a further embodiment, a method for treating TBI comprising administering an effective amount of a PIF peptide in combination with one or more immunotherapeutic, anti-epileptic, diuretic, or blood pressure controlling drugs or compounds to a subject in need thereof is provided. Such a combination may enhance the effectiveness of the treatment of either component alone, or may provide less side effects and/or enable a lower dose of either component.

In one embodiment of the present invention, a PIF peptide is provided. Such PIF peptides may be useful for treating or ameliorating immune-mediated disorders, such as autoimmune diseases.

In another embodiment, a pharmaceutical composition comprising a PIF peptide or a pharmaceutically acceptable salt thereof is provided. In preferred embodiments, the pharmaceutical composition comprises a therapeutically effective amount of a PIF peptide or a pharmaceutically acceptable salt thereof.

In another embodiment, a method of treating or presenting immune-mediated disorders is provided. In a preferred embodiment, the method comprises administering an effective amount of a PIF peptide to a subject in need thereof. The methods are particularly useful in treating or preventing immune-mediated disorders, including, but not limited to, graft-versus-host disease type 1 diabetes, multiple sclerosis, ulcerative colitis, Crohn's disease, rheumatoid arthritis and the like.

In a further embodiment, a method for treating or preventing immune-mediated disorders comprising administering an effective amount of a PIF peptide in combination with one or more immunotherapeutic drugs to a subject in need thereof is provided. Such a combination may enhance the effectiveness of the treatment of either component alone, or may provide less side effects and/or enable a lower dose of either component.

PIF-1's action appears to be independent of TCR, calcium-channels or PKC pathways, mechanisms through which most immunosuppressive agents act, and CD4+/CD25+ cells (T reg) cells that are of relevance in various autoimmune diseases. On the other hand, PIF-1's action may involve NFAT-1 suppression.

Ultimately, a novel embryo-derived peptide, PIF, creates a tolerogenic state at low doses following short-term treatment leading to long-term protection in several distinct severe autoimmune models. This effect is exerted without apparent toxicity.

For therapeutic treatment of the specified indications, a PIF peptide may be administered as such, or can be compounded and formulated into pharmaceutical compositions in unit dosage form for parenteral, transdermal, rectal, nasal, local intravenous administration, or, preferably, oral administration. Such pharmaceutical compositions are prepared in a manner well known in the art and comprise at least one active PIF peptide associated with a pharmaceutically carrier. The term "active compound", as used throughout this specification, refers to at least one compound selected from compounds of the formulas or pharmaceutically acceptable salts thereof.

In such a composition, the active compound is known as "active ingredient." In making the compositions, the active ingredient will usually be mixed with a carrier, or diluted by a carrier, or enclosed within a carrier that may be in the form of a capsule, sachet, paper or other container. When the carrier serves as a diluent, it may be a solid, semisolid, or liquid material that acts as a vehicle, excipient of medium for the active ingredient. Thus, the composition can be in the form of tablets, pills, powders, lozenges, sachets, cachets, elixirs, emulsion, solutions, syrups, suspensions, soft and hard gelatin capsules, sterile injectable solutions, and sterile packaged powders.

The terms "pharmaceutical preparation" or "pharmaceutical composition" includes preparations suitable for administration to mammals, e.g., humans. When the compounds of the present disclosure are administered as pharmaceuticals to mammals, e.g., humans, they can be given per se or as a pharmaceutical composition containing, for example, from about 0.1 to about 99.5% of active ingredient in combination with a pharmaceutically acceptable carrier.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in "Remington's Pharmaceutical Sciences" by E. W. Martin, which is incorporated herein by reference in its entirety. In some embodiments, the pharmaceutically acceptable carrier is sterile and pyrogen-free water. In some embodiments, the pharmaceutically acceptable carrier is Ringer's Lactate, sometimes known as lactated Ringer's solution.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, .alpha.-tocopherol, and the like; and metal chelating agents, such as citric acid, ethylenediamine tetraacetic acid (EDTA), sorbitol, tartaric acid, phosphoric acid, and the like.

Formulations of the present disclosure include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water, or the like, and administered intravenously or by injection.

The local delivery of inhibitory amounts of active compound for the treatment of immune disorders can be by a variety of techniques that administer the compound at or near the targeted site. Examples of local delivery techniques are not intended to be limiting but to be illustrative of the techniques available. Examples include local delivery catheters, site specific carriers, implants, direct injection, or direct applications, such as topical application.

Local delivery by an implant describes the surgical placement of a matrix that contains the pharmaceutical agent into the affected site. The implanted matrix releases the pharmaceutical agent by diffusion, chemical reaction, or solvent activators.

For example, in some aspects, the disclosure is directed to a pharmaceutical composition comprising a PIF peptide, and a pharmaceutically acceptable carrier or diluent, or an effective amount of pharmaceutical composition comprising a PIF peptide.

The compounds of the present disclosure can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, ocular routes, intravaginally, by inhalation, by depot injections, or by implants. Thus, modes of administration for the compounds of the present disclosure (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular mammal or human treated, age, weight, health, types of concurrent treatment, if any, and frequency of treatments, and can be easily determined by one of skill in the art (e.g., by the clinician).

Pharmaceutical formulations containing the compounds of the present disclosure and a suitable carrier can be solid dosage forms which include, but are not limited to, tablets, capsules, cachets, pellets, pills, powders and granules; topical dosage forms which include, but are not limned to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present disclosure. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

The compounds of the present disclosure can be formulated for parenteral administration by injection, e.g., by bolus injection or continuous infusion. The compounds can be administered by continuous infusion subcutaneously over a predetermined period of time. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, alter adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragecanth, methyl cellulose, hydroxypropylmethyl-celllose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, scaled capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present disclosure can also be formulated in rectal compositions such as suppositories or retention enemas, e.g., containing conventional suppository bases such as cocoa butter or other glycerides.

In addition to the formulations described previously, the compounds of the present disclosure can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present disclosure, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivates, gelatin, and polymers such as, e.g., polyethylene glycols.

For parenteral administration, analog can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of analog in 0.9% sodium chloride solution.

The present invention relates to routes of administration include intramuscular, sublingual, intravenous, intraperitoneal, intrathecal, intravaginal, intraurethral, intradermal, intrabuccal, via inhalation, via nebulizer and via subcutaneous injection. Alternatively, the pharmaceutical composition may be introduced by various means into cells that are removed from the individual. Such means include, for example, microprojectile bombardment and liposome or other nanoparticle device.

Solid dosage forms for oral administration include capsules, tablets, pills, powders and granules. In solid dosage forms, the analogs are generally admixed with at least one inert pharmaceutically acceptable carrier such as sucrose, lactose, starch, or other generally regarded as safe (GRAS) additives. Such dosage forms can also comprise, as is normal practice, an additional substance other than an inert diluent, e.g., lubricating agent such as magnesium state. With capsules, tablets, and pills, the dosage forms may also comprise a buffering agent. Tablets and pills can additionally be prepared with enteric coatings, or in a controlled release form, using techniques know in the art.

Liquid dosage forms for oral administration include pharmaceutically acceptable emulsions, solutions, suspensions and syrups, with the elixirs containing an inert diluent commonly used in the art, such as water. These compositions can also include one or more adjuvants, such as wetting agent, an emulsifying agent, a suspending agent, a sweetening agent, a flavoring agent or a perfuming agent.

In another embodiment of the invention the composition of the invention is used to treat a patient suffering from, or susceptible to Type I adult or juvenile diabetes, multiple sclerosis, Crohn's, or autoimmune hepatitis.

One of skill in the art will recognize that the appropriate dosage of the compositions and pharmaceutical compositions may vary depending on the individual being treated and the purpose. For example, the age, body weight, and medical history of the individual patient may affect the therapeutic efficacy of the therapy. Further, a lower dosage of the composition may be needed to produce a transient cessation of symptoms, while a larger dose may be needed to produce a complete cessation of symptoms associated with the disease, disorder, or indication. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response. Dosages may also depend on the strength of the particular analog chosen for the pharmaceutical composition.

The dose of the composition or pharmaceutical compositions may vary. The dose of the composition may be once per day. In some embodiments, multiple doses may be administered to the subject per day. In some embodiments, the total dosage is administered in at least two application periods. In some embodiments, the period can be an hour, a day, a month, a year, a week, or a two-week period. In an additional embodiment of the invention, the total dosage is administered in two or more separate application periods, or separate doses over the course of about an hour, 2 hours, 3 hours, 4 hours, 5 hours, 6 hours, 7 hours, 8 hours, 9 hours, 10 hours, 11 hours, 12 or more hours. a day, a month, a year, a week, or a two-week period.

In some embodiments, subjects can be administered the composition in which the composition is provided in a daily dose range of about 0.0001 mg/kg to about 5000 mg/kg of the weight of the subject. The dose administered to the subject can also be measured in terms of total amount of PIF peptide or PIF analog or pharmaceutically acceptable salt thereof administered per day. In some embodiments, a subject is administered from about 0.001 to about 3000 milligrams of PIF peptide or PIF analog or pharmaceutically acceptable salt thereof per day. In some embodiments, a subject is administered up to about 2000 milligrams of PIF peptide or PIF analog or pharmaceutically acceptable salt thereof per day. In some embodiments, a subject is administered up to about 1800 milligrams of PIF peptide or PIF analog or pharmaceutically acceptable salt thereof per day. In some embodiments, a subject is administered up to about 1600 milligrams of PIF peptide or PIF analog or pharmaceutically acceptable salt thereof per day. In some embodiments, a subject is administered up to about 1400 milligrams of PIF peptide or PIF analog or pharmaceutically acceptable salt thereof per day. In some embodiments, a subject is administered up to about 1200 milligrams of PIF peptide or PIF analog or pharmaceutically acceptable salt thereof per day. In some embodiments, a subject is administered up to about 1000 milligrams of PIF peptide or PIF analog or pharmaceutically acceptable salt thereof per day. In some embodiments, a subject is administered up to about 800 milligrams of PIF peptide or PIF analog or pharmaceutically acceptable salt thereof per day. In some embodiments, a subject is administered from about 0.001 milligrams to about 700 milligrams of PIF peptide or PIF analog or pharmaceutically acceptable salt thereof per dose. In some embodiments, a subject is administered up to about 700 milligrams of PIF peptide or PIF analog per dose. In some embodiments, a subject is administered up to about 600 milligrams of PIF peptide or PIF analog or pharmaceutically acceptable salt thereof per dose. In some embodiments, a subject is administered up to about 500 milligrams of PIF peptide or PIF analog or pharmaceutically acceptable salt thereof per dose. In some embodiments, a subject is administered up to about 400 milligrams of PIF peptide or PIF analog or pharmaceutically acceptable salt thereof per dose. In some embodiments, a subject is administered up to about 300 milligrams of PIF peptide or PIF analog or pharmaceutically acceptable salt thereof per dose. In some embodiments, a subject is administered up to about 200 milligrams of PIF peptide or PIF analog or pharmaceutically acceptable salt thereof per dose. In some embodiments, a subject is administered up to about 100 milligrams of PIF peptide or PIF analog or pharmaceutically acceptable salt thereof per dose. In some embodiments, a subject is administered up to about 50 milligrams of PIF peptide or PIF analog or pharmaceutically acceptable salt thereof per dose.

In some embodiments, subjects can be administered the composition in which the composition comprising a PIF peptide or PIF analog or pharmaceutically acceptable salt thereof is administered in a daily dose range of about 0.0001 mg/kg to about 5000 mg/kg of the weight of the subject. In some embodiments, the composition comprising a PIF analog or pharmaceutically acceptable salt thereof is administered in a daily dosage of up to about 450 mg/kg of the weight of the subject. In some embodiments, the composition comprising a PIF peptide or PIF analog or pharmaceutically acceptable salt thereof is administered in a daily dosage of up to about 400 mg/kg of the weight of the subject. In some embodiments, the composition comprising a PIF peptide or PIF analog or pharmaceutically acceptable salt thereof is administered in a daily dosage of up to about 350 mg/kg of the weight of the subject. In some embodiments, the composition comprising a PIF peptide or PIF analog or pharmaceutically acceptable salt thereof is administered in a daily dosage of up to about 300 mg/kg of the weight of the subject. In some embodiments, the composition comprising a PIF peptide or PIF analog or pharmaceutically acceptable salt thereof is administered in a daily dosage of up to about 250 mg/kg of the weight of the subject. In some embodiments, the composition comprising PIF peptide or a PIF analog or pharmaceutically acceptable salt thereof is administered in a daily dosage of up to about 200 mg/kg of the weight of the subject. In some embodiments, the composition comprising PIF peptide or a PIF analog or pharmaceutically acceptable salt thereof is administered in a daily dosage of up to about 150 mg/kg of the weight of the subject. In some embodiments, the composition comprising a PIF peptide or a PIF analog or pharmaceutically acceptable salt thereof is administered in a daily dosage of up to about 100 mg/kg of the weight of the subject. In some embodiments, the composition comprising a PIF peptide or a PIF analog or pharmaceutically acceptable salt thereof is administered in a daily dosage of up to about 50 mg/kg of the weight of the subject. In some embodiments, the composition comprising PIF peptide or a PIF analog or pharmaceutically acceptable salt thereof is administered in a daily dosage of up to about 25 mg/kg of the weight of the subject.

In some embodiments, the composition comprising a PIF peptide or a PIF analog or pharmaceutically acceptable salt thereof is administered in a daily dosage of up to about 10 mg/kg of the weight of the subject. In some embodiments, the composition comprising PIF peptide or a PIF analog or pharmaceutically acceptable salt thereof is administered in a daily dosage of up to about 5 mg/kg of the weight of the subject. In some embodiments, the composition comprising PIF peptide or a PIF analog or pharmaceutically acceptable salt thereof is administered in a daily dosage of up to about 1 mg/kg of the weight of the subject. In some embodiments, the composition comprising a PIF peptide or a PIF analog or pharmaceutically acceptable salt thereof is administered in a daily dosage of up to about 0.1 mg/kg of the weight of the subject. In some embodiments, the composition comprising a PIF analog or pharmaceutically acceptable salt thereof is administered in a daily dosage of up to about 0.01 mg/kg of the weight of the subject. In some embodiments, the composition comprising a PIF analog or pharmaceutically acceptable salt thereof is administered in a daily dosage of up to about 0.001 mg/kg of the weight of the subject. The dose administered to the subject can also be measured in terms of total amount of a PIF peptide or PIF analog administered per day.

In some embodiments, a subject in need thereof is administered from about 1 ng to about 500 µg of analog or pharmaceutically salt thereof per day. In some embodiments, a subject in need thereof is administered from about 1 ng to about 10 ng of analog or pharmaceutically salt thereof per day. In some embodiments, a subject in need thereof is administered from about 10 ng to about 20 ng of analog or pharmaceutically salt thereof per day. In some embodiments, a subject in need thereof is administered from about 10 ng to about 100 ng of analog or pharmaceutically salt thereof per day. In some embodiments, a subject in need thereof is administered from about 100 ng to about 200 ng of analog or pharmaceutically salt thereof per day. In some embodiments, a subject in need thereof is administered from about 200 ng to about 300 ng of analog or pharmaceutically salt thereof per day. In some embodiments, a subject in need thereof is administered from about 300 ng to about 400 ng of analog or pharmaceutically salt thereof per day. In some embodiments, a subject in need thereof is administered from about 400 ng to about 500 ng of analog or pharmaceutically salt thereof per day. In some embodiments, a subject in need thereof is administered from about 500 ng to about 600 ng of analog or pharmaceutically salt thereof per day. In some embodiments, a subject in need thereof is administered from about 600 ng to about 700 ng of analog or pharmaceutically salt thereof per day. In some embodiments, a subject in need thereof is administered from about 800 ng to about 900 ng of analog or pharmaceutically salt thereof per day. In some embodiments, a subject in need thereof is administered from about 900 ng to about 1 µg of analog or pharmaceutically salt thereof per day. In some embodiments, a subject in need thereof is administered from about 1 µg to about 100 µg of analog or pharmaceutically salt thereof per day. In some embodiments, a subject in need thereof is administered from about 100 µg to about 200 µg of analog or pharmaceutically salt thereof per day. In some embodiments, a subject in need thereof is administered from about 200 µs to about 300 µg of analog or pharmaceutically salt thereof per day. In some embodiments, a subject in need thereof is administered from about 300 µg to about 400 µg of analog or pharmaceutically salt thereof per day. In some embodiments, a subject in need thereof is administered from about 400 µg to about 500 µg of analog or pharmaceutically salt thereof per day. In some embodiments, a subject in need thereof is administered from about 500 µg to about 600 µg of analog or pharmaceutically salt thereof per day. In some embodiments, a subject in need thereof is administered from about 600 µg to about 700 µg of analog or pharmaceutically salt thereof per day. In some embodiments, a subject in need thereof is administered from about 800 µs to about 900 µg of analog or pharmaceutically salt thereof per day. In some embodiments, a subject in need thereof is administered from about 900 µg to about 1 mg of analog or pharmaceutically salt thereof per day.

In some embodiments, a subject in need thereof is administered from about 0.0001 to about 3000 milligrams of a PIF peptide or PIF analog or pharmaceutically salt thereof per day. In some embodiments, a subject is administered up to about 2000 milligrams of a PIF peptide or PIF analog or pharmaceutically salt thereof day. In some embodiments, a subject is administered up to about 1800 milligrams of a PIF peptide or PIF analog or pharmaceutically salt thereof per day. In some embodiments, a subject is administered up to about 1600 milligrams of a PIF peptide or PIF analog or pharmaceutically salt thereof per day. In some embodiments, a subject is administered up to about 1400 milligrams of a PIF peptide or PIF analog or pharmaceutically salt thereof per day. In some embodiments, a subject is administered up to about 1200 milligrams of a PIF peptide or PIF analog or pharmaceutically salt thereof per day. In some embodiments, a subject is administered up to about 1000 milligrams of a PIF peptide or PIF analog or pharmaceutically salt thereof per day. In some embodiments, a subject is administered up to about 800 milligrams of a PIF peptide or PIF analog or pharmaceutically salt thereof per day. In some embodiments, a subject is administered from about 0.0001 milligrams to about 700 milligrams of a PIF peptide or PIF analog or pharmaceutically salt thereof per dose. In some embodiments, a subject is administered up to about 700 milligrams of a PIF peptide or PIF analog or pharmaceutically salt thereof per dose. In some embodiments, a subject is administered up to about 600 milligrams of a PIF peptide or PIF analog or pharmaceutically salt thereof per dose. In some embodiments, a subject is administered up to about 500 milligrams of a PIF peptide or PIF analog or pharmaceutically salt thereof per dose. In some embodiments, a subject is administered up to about 400 milligrams of a PIF peptide or PIF analog or pharmaceutically salt thereof per dose. In some embodiments, a subject is administered up to about 300 milligrams of a PIF peptide or PIF analog or pharmaceutically salt thereof per dose. In some embodiments, a subject is administered up to about 200 milligrams of a PIF peptide or PIF analog or pharmaceutically salt thereof per dose. In some embodiments, a subject is administered up to about 100 milligrams of a PIF peptide or PIF analog or pharmaceutically salt thereof per dose. In some embodiments, a subject is administered up to about 50 milligrams of a PIF peptide or PIF analog or pharmaceutically salt thereof per dose. In some embodiments, a subject is administered up to about 25 milligrams of a PIF peptide or PIF analog or pharmaceutically salt thereof per dose. In some embodiments, a subject is administered up to about 15 milligrams of a PIF peptide or PIF analog or pharmaceutically salt thereof per dose.

In some embodiments, a subject is administered up to about 10 milligrams of a PIF peptide or PIF analog or pharmaceutically salt thereof per dose. In some embodiments, a subject is administered up to about 5 milligrams of a PIF peptide or PIF analog or pharmaceutically salt thereof per dose. In some embodiments, a subject is administered up to about 1 milligram of a PIF peptide or PIF analog or pharmaceutically salt thereof per dose. In some embodiments, a subject is administered up to about 0.1 milligrams of a PIF peptide or PIF analog or pharmaceutically salt thereof per dose. In some embodiments, a subject is administered up to about 0.001 milligrams of a PIF peptide or PIF analog or pharmaceutically salt thereof per dose.

The dose administered to the subject can also be measured in terms of total amount of a PIF peptide or PIF analog or pharmaceutically salt thereof administered per ounce of liquid prepared. In some embodiments, the PIF peptide or PIF analog or pharmaceutically salt thereof is at a concentration of about 2.5 grams per ounce of solution. In some embodiments, the PIF peptide or PIF analog or pharmaceutically salt thereof is at a concentration of about 2.25 grams per ounce of solution. In some embodiments, the PIF peptide or PIF analog or pharmaceutically salt thereof is at a concentration of about 2.25 grams per ounce of solution. In some embodiments, the PIF peptide or PIF analog or pharmaceutically salt thereof is at a concentration of about 2.0 grams per ounce of solution. In some embodiments, the PIF peptide or PIF analog or pharmaceutically salt thereof is at a concentration of about 1.9 grams per ounce of solution. In some embodiments, the PIF peptide or PIF analog or pharmaceutically salt thereof is at a concentration of about 1.8 grams per ounce of solution. In some embodiments, the PIF analog or pharmaceutically salt thereof is at a concentration of about 1.7 grams per ounce of solution. In some embodiments, the PIF peptide or PIF analog or pharmaceutically salt thereof is at a concentration of about 1.6 grams per ounce of solution. In some embodiments, the PIF peptide or PIF analog or pharmaceutically salt thereof is at a concentration of about 1.5 grams per ounce of solution. In some embodiments, the PIF peptide or PIF analog or pharmaceutically salt thereof is at a concentration of about 1.4 grams per ounce of solution. In some embodiments, the PIF peptide or PIF analog or pharmaceutically salt thereof is at a concentration of about 1.3 grams per ounce of solution. In some embodiments, the PIF peptide or PIF analog or pharmaceutically salt thereof is at a concentration of about 1.2 grams per ounce of solution. In some embodiments, the PIF peptide or PIF analog or pharmaceutically salt thereof is at a concentration of about 1.1 grams per ounce of solution. In some embodiments, the PIF peptide or PIF analog or pharmaceutically salt thereof is at a concentration of about 1.0 grams per ounce of solution. In some embodiments, the PIF peptide or PIF analog or pharmaceutically salt thereof is at a concentration of about 0.9 grams per ounce of solution. In some embodiments, the PIF peptide or PIF analog or pharmaceutically salt thereof is at a concentration of about 0.8 grams per ounce of solution. In some embodiments, the PIF peptide or PIF analog or pharmaceutically salt thereof is at a concentration of about 0.7 grams per ounce of solution. In some embodiments, the PIF peptide or PIF analog or pharmaceutically salt thereof is at a concentration of about 0.6 grams per ounce of solution. In some embodiments, the PIF peptide or PIF analog or pharmaceutically salt thereof is at a concentration of about 0.5 grams per ounce of solution. In some embodiments, the PIF peptide or PIF analog or pharmaceutically salt thereof is at a concentration of about 0.4 grams per ounce of solution. In some embodiments, the PIF peptide or PIF analog or pharmaceutically salt thereof is at a concentration of about 0.3 grams per ounce of solution. In some embodiments, the PIF peptide or PIF analog or pharmaceutically salt thereof is at a concentration of about 0.2 grams per ounce of solution. In some embodiments, the PIF peptide or PIF analog or pharmaceutically salt thereof is at a concentration of about 0.1 grams per ounce of solution. In some embodiments, the PIF peptide or PIF analog or pharmaceutically salt thereof is at a concentration of about 0.01 grams per ounce of solution. In some embodiments, the PIF peptide or PIF analog or pharmaceutically salt thereof is at a concentration of about 0.001 grams per ounce of solution prepared. In some embodiments, the PIF peptide or PIF analog or pharmaceutically salt thereof is at a concentration of about 0.0001 grams per ounce of solution prepared. In some embodiments, the PIF peptide or PIF analog or pharmaceutically salt thereof is at a concentration of about 0.00001 grams per ounce of solution prepared. In some embodiments, the PIF peptide or PIF analog or pharmaceutically salt thereof is at a concentration of about 0.000001 grams per ounce of solution prepared.

Dosage may be measured in terms of mass amount of analog per liter of liquid formulation prepared. One skilled in the art can increase or decrease the concentration of the analog in the dose depending upon the strength of biological activity desired to treat or prevent any above-mentioned disorders associated with the treatment of subjects in need thereof. For instance, some embodiments of the invention can include up to 0.00001 grams of analog per 5 mL of liquid formulation and up to about 10 grams of analog per 5 mL of liquid formulation In some embodiments, the pharmaceutical compositions comprising a PIF analog or any of such compositions in any of the disclosed methods are free of SEQ ID NO:1. In some embodiments, the pharmaceutical compositions comprising a PIF analog or any of such compositions in any of the disclosed methods are free of SEQ ID NO:2. In some embodiments, the pharmaceutical compositions comprising a PIF analog or any of such compositions in any of the disclosed methods are free of SEQ ID NO:3. In some embodiments, the pharmaceutical compositions comprising a PIF analog or any of such compositions in any of the disclosed methods are free of SEQ ID NO:4. In some embodiments, the pharmaceutical compositions comprising a PIF analog or any of such compositions in any of the disclosed methods are free of SEQ ID NO:5. In some embodiments, the pharmaceutical compositions comprising a PIF analog or any of such compositions in any of the disclosed methods are free of SEQ ID NO:6. In some embodiments, the pharmaceutical compositions comprising a PIF analog or any of such compositions in any of the disclosed methods are free of SEQ ID NO:7. In some embodiments, the pharmaceutical compositions comprising a PIF analog or any of such compositions in any of the disclosed methods are free of SEQ ID NO:8. In some embodiments, the pharmaceutical compositions comprising a PIF analog or any of such compositions in any of the disclosed methods are free of SEQ ID NO:9. In some embodiments, the pharmaceutical compositions comprising a PIF analog or any of such compositions in any of the disclosed methods are free of SEQ ID NO:10.

In some embodiments the pharmaceutical compositions of the claimed invention comprises at least one or a plurality of active agents other than the PIF peptide, analog or pharmaceutically acceptable salt thereof. In some embodiments the active agent is covalently linked to the PIF peptide or PIF analog disclosed herein optionally by a protease cleavable linker (including by not limited to Pro-Pro or Cituline-Valine di-α-amino acid linkers). In some embodiments, the one or plurality of active agents is one or a combination of compounds chosen from: an anti-inflammatory compound, alpha-adrenergic agonist, antiarrhythmic compound, analgesic compound, and an anesthetic compound.

TABLE Y

Examples of anti-inflammatory compounds include:

aspirin
celecoxib
diclofenac
diflunisal
etodolac
ibuprofen
indomethacin
ketoprofen
ketorolac nabumetone
naproxen
oxaprozin
piroxicam
salsalate
sulindac
tolmetin Examples of alpha-adrenergic agonists include:

Methoxamine
Methylnorepinephrine
Midodrine
Oxymetazoline
Metaraminol
Phenylephrine
Clonidine (mixed alpha2-adrenergic and imidazoline-I1 receptor agonist)
Guanfacine, (preference for alpha2A-subtype of adrenoceptor)
Guanabenz (most selective agonist for alpha2-adrenergic as opposed to imidazoline-I1)
Guanoxabenz (metabolite of guanabenz)
Guanethidine (peripheral alpha2-receptor agonist)
Xylazine,
Tizanidine
Medetomidine
Methyldopa
Fadolmidine
Dexmedetomidine Examples of antiarrhythmic compound include:

Amiodarone (Cordarone, Pacerone)
Bepridil Hydrochloride (Vascor)
Disopyramide (Norpace)
Dofetilide (Tikosyn)
Dronedarone (Multaq)
Flecainide (Tambocor)
Ibutilide (Corvert)
Lidocaine (Xylocaine)
Procainamide (Procan, Procanbid)
Propafenone (Rythmol)
Propranolol (Inderal)
Quinidine (many trade names)
Sotalol (Betapace)
Tocainide (Tonocarid)

Examples of analgesic compound include:

codeine
hydrocodone (Zohydro ER),
oxycodone (OxyContin, Roxicodone),
methadone
hydromorphone (Dilaudid, Exalgo),
morphine (Avinza, Kadian, MSIR, MS Contin), and
fentanyl (Actiq, Duragesic)

Examples of anesthetic compounds include:

Desflurane
Isoflurane
Nitrous oxide
Sevoflurane
Xenon

The compounds of the present disclosure can also be administered in combination with other active ingredients, such as, for example, adjuvants, or other compatible drugs or compounds where such combination is seen to be desirable or advantageous in achieving the desired effects of the methods described herein.

Methods

International Application Serial Number PCT/US2012/027480 is incorporated by reference in its entirety and any of the methods disclosed therein may be performed with the PIF analogs of this application in place of or in addition to the experiments performed with native PIF sequences. Comparative experimentation may demonstrate that the PIF analogs of this application may share one or more properties tested in International Application Serial Number PCT/US2012/027480.

The methods disclosed herein can be used with any of the compounds, compositions, preparations, and kits disclosed herein.

The disclosure relates to methods for treating a bronchopulmonary dysplasia trauma comprising administering an effective amount of the compositions described herein to a subject in need thereof. The disclosure also includes the use of the compositions described here for simultaneously treating a subject who has suffered a neurodamage, for instance a traumatic neural damage and bronchopulmonary dysplasia.

The disclosure relates to methods for treating a CNS trauma comprising administering an effective amount of the compositions described herein to a subject in need thereof. The disclosure also includes the use of the compositions described here for treating a subject who has suffered a CNS trauma. In some embodiments, the CNS trauma is traumatic brain injury (TBI). In some embodiments, the CNS trauma is spinal cord injury (SCI).

In some embodiments, the CNS trauma is a concussion. Accordingly, the disclosure also relates to methods for treating a concussion comprising administering an effective amount of the compositions described herein to a subject in need thereof. The disclosure also relates to the use of the compositions described here for treating a subject who has suffered a concussion. In some embodiments, the present methods are used for treating a subject who has at least 1, 2, 3, 4 or 5 concussion symptoms. Concussion symptoms include, but are not limited to, headache, pressure in head, neck pain, nausea or vomiting, dizziness, blurred vision, sensitivity to light, sensitivity to noise, feeling slowed down, feeling "in a fog", "not feeling right", difficulty concentrating, difficulty remembering, fatigue or low energy, confusion, drowsiness, trouble falling asleep, increased emotions, irritability sadness and nervousness or anxiety. Optionally, the present methods are used for treating a subject who has been diagnosed with a traumatic brain injury or a concussion.

In another embodiment, the present methods are used for treating a post-concussive syndrome. Post-concussive syndromes include, but are not limited to, post-concussion disease, prolonged post-concussion disease, mild cognitive impairment, chronic traumatic encephalopathy and dementia pugilistica. In further embodiments the present methods are used for treating long-term complications of concussion such as post-concussive depression.

In an embodiment, the composition is administered once a day to a subject in need thereof. In another embodiment, the composition is administered every other day, every third day or once a week. In another embodiment, the composition is administered twice a day. In still another embodiment, the composition is administered three times a day or four times a day. In a further embodiment, the composition is administered at least once a day for at least 1, 2, 3, 4, 5, 6, 7, 8, 9, 10, 11 or 12 weeks. In still a further embodiment, the composition is administered at least once a day for a longer term such as at least 4, 6, 8, 10, 12 or 24 months. Administration in some embodiments includes but is not limited to a dosage of 10-50 mg of composition at a frequency of minimum 1, 2, 3 or 4 times per day. Optionally, administration continues until all symptoms are resolved and cleared by medical personnel via standardized testing such as SCAT 2.

In some embodiments, the composition is administered within 1, 2, 3, 5 or 7 days of the CNS trauma. In other embodiments, the composition is administered within 1, 2, 3, 5 or 7 days of the appearance of symptoms of a CNS trauma.

In some embodiments, the composition is administered at least once a day until the condition has ameliorated to where further treatment is not necessary. In another embodiment, the composition is administered until all symptoms of the traumatic brain injury are resolved. In another embodiment, the composition is administered until the subject is able to return to physical activity or "cleared to play" in a particular sport.

In further embodiments, the composition is administered for at least 1, 2, 3, 6, 8, 10 or 12 or 24 months after the subject is asymptomatic. Optionally, the composition is administered for at least 1, 2, 3, 6, 8, 10 or 12 or 24 months after the subject is able to return to physical activity or "cleared to play" in a particular sport.

The compositions of the present disclosure are useful and effective when administered to treat a CNS trauma such as, TBI, SCI, cerebral herniation or a concussion. The amount of each component present in the composition will be the amount that is therapeutically effective, i.e., an amount that will result in the effective treatment of the condition (e.g., traumatic brain injury) when administered. The therapeutically effective amount will vary depending on the subject and the severity and nature of the injury and can be determined routinely by one of ordinary skill in the art.

In some embodiments, the disclosure relates to a method of treating or preventing any of the indications set forth in U.S. Pat. Nos. 8,222,211, 7,723,289, 7,723,290, 8,454,967, 9,097,725, (each of which are incorporated by reference in their entireties) comprising administering compositions or pharmaceutical compositions comprising any one or plurality of PIF peptides, analogs, or pharmaceutically acceptable salts thereof disclosed herein.

In some methods, the disclosure relates to a method of stimulating the differentiation and/or proliferation of stem cells in a subject in need thereof comprising administering compositions or pharmaceutical compositions comprising any one or plurality of PIF peptides, analogs, or pharmaceutically acceptable salts thereof disclosed herein.

In some embodiments, the disclosure relates to any of the methods disclosed in U.S. Pat. Nos. 7,273,708, 7,695,977, 7,670,852, 7,670,851, 7,678,582, 7,670,850, 8,012,700 (each of which are incorporated by reference in their entireties) comprising administering compositions or pharmaceutical compositions comprising any one or plurality of PIF peptides, analogs, or pharmaceutically acceptable salts thereof disclosed herein.

This disclosure also incorporates by reference in their entireties U.S. Pat. Nos. 7,789,289, 7,723,290, 8,222,211, and 8,454,967.

In some embodiments, the disclosure relates to a method of treating traumatic injury of the central nervous system by administering at least one or a plurality of compositions disclosed herein comprising PIF peptide, an analog thereof, or a pharmaceutically acceptable salt thereof.

In some embodiments, the disclosure relates to a method of treating traumatic injury of the central nervous system by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating traumatic injury of the central nervous system by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of traumatic injury of the central nervous system.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of traumatic injury of the central nervous system.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of traumatic injury of the central nervous system.

In some embodiments, the disclosure relates to a method of inducing an immunomodulation effect in a subject in need thereof, when subject has been or is suspect of having traumatic injury of the central nervous system.

In some embodiments, the disclosure relates to a method of treating traumatic brain injury by administering at least one or a plurality of compositions disclosed herein comprising PIF peptide, an analog thereof, or a pharmaceutically acceptable salt thereof.

In some embodiments, the disclosure relates to a method of treating traumatic brain injury by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating traumatic brain injury by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of traumatic brain injury.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of traumatic brain injury.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of traumatic brain injury.

In some embodiments, the disclosure relates to a method of inducing an immunomodulation effect in a subject in need thereof, when subject has been or is suspect of having traumatic brain injury.

In some embodiments, the disclosure relates to a method of treating auto-immune hepatitis by administering at least one or a plurality of compositions disclosed herein comprising PIF peptide, an analog thereof, or a pharmaceutically acceptable salt thereof.

In some embodiments, the disclosure relates to a method of treating auto-immune hepatitis by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating auto-immune hepatitis by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of auto-immune hepatitis.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of auto-immune hepatitis.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of auto-immune hepatitis.

In some embodiments, the disclosure relates to a method of inducing an immunomodulation effect in a subject in need thereof, when subject has been or is suspect of having auto-immune hepatitis.

In some embodiments, the disclosure relates to a method of treating graft-versus-host disease by administering at least one or a plurality of compositions disclosed herein comprising PIF peptide, an analog thereof, or a pharmaceutically acceptable salt thereof.

In some embodiments, the disclosure relates to a method of treating graft-versus-host disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating graft-versus-host disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of graft-versus-host disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of graft-versus-host disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of graft-versus-host disease.

In some embodiments, the disclosure relates to a method of inducing an immunomodulation effect in a subject in need thereof, when subject has been or is suspect of having graft-versus-host disease.

In some embodiments, the disclosure relates to a method of treating type I diabetes by administering at least one or a plurality of compositions disclosed herein comprising PIF peptide, an analog thereof, or a pharmaceutically acceptable salt thereof.

In some embodiments, the disclosure relates to a method of treating type I diabetes by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating type I diabetes by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of type I diabetes.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of type I diabetes.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of type I diabetes.

In some embodiments, the disclosure relates to a method of inducing an immunomodulation effect in a subject in need thereof, when subject has been or is suspect of having type I diabetes.

In some embodiments, the disclosure relates to a method of treating multiple sclerosis by administering at least one or a plurality of compositions disclosed herein comprising PIF peptide, an analog thereof, or a pharmaceutically acceptable salt thereof.

In some embodiments, the disclosure relates to a method of treating multiple sclerosis by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating multiple sclerosis by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of multiple sclerosis.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of multiple sclerosis.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of multiple sclerosis.

In some embodiments, the disclosure relates to a method of inducing an immunomodulation effect in a subject in need thereof, when subject has been or is suspect of having multiple sclerosis.

In some embodiments, the disclosure relates to a method of treating ulcerative colitis by administering at least one or a plurality of compositions disclosed herein comprising PIF peptide, an analog thereof, or a pharmaceutically acceptable salt thereof.

In some embodiments, the disclosure relates to a method of treating ulcerative colitis by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating ulcerative colitis by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of ulcerative colitis.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of ulcerative colitis.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of ulcerative colitis.

In some embodiments, the disclosure relates to a method of inducing an immunomodulation effect in a subject in need thereof, when subject has been or is suspect of having ulcerative colitis.

In some embodiments, the disclosure relates to a method of treating Crohn's disease by administering at least one or a plurality of compositions disclosed herein comprising PIF peptide, an analog thereof, or a pharmaceutically acceptable salt thereof.

In some embodiments, the disclosure relates to a method of treating Crohn's disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating Crohn's disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of Crohn's disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of Crohn's disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of Crohn's disease.

In some embodiments, the disclosure relates to a method of inducing an immunomodulation effect in a subject in need thereof, when subject has been or is suspect of having Crohn's disease.

In some embodiments, the disclosure relates to a method of treating inflammatory bowel disease by administering at least one or a plurality of compositions disclosed herein comprising PIF peptide, an analog thereof, or a pharmaceutically acceptable salt thereof.

In some embodiments, the disclosure relates to a method of treating inflammatory bowel disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating inflammatory bowel disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of inflammatory bowel disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of inflammatory bowel disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of inflammatory bowel disease.

In some embodiments, the disclosure relates to a method of inducing an immunomodulation effect in a subject in need thereof, when subject has been or is suspect of having inflammatory bowel disease.

In some embodiments, the disclosure relates to a method of treating inflammation by administering at least one or a plurality of compositions disclosed herein comprising PIF peptide, an analog thereof, or a pharmaceutically acceptable salt thereof.

In some embodiments, the disclosure relates to a method of treating inflammation by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating inflammation by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of inflammation.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of inflammation.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of inflammation.

In some embodiments, the disclosure relates to a method of inducing an immunomodulation effect in a subject in need thereof, when subject has been or is suspect of having inflammation.

In some embodiments, the disclosure relates to a method of treating arthritis by administering at least one or a plurality of compositions disclosed herein comprising PIF peptide, an analog thereof, or a pharmaceutically acceptable salt thereof.

In some embodiments, the disclosure relates to a method of treating arthritis by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating arthritis by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of arthritis.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of arthritis.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of arthritis.

In some embodiments, the disclosure relates to a method of inducing an immunomodulation effect in a subject in need thereof, when subject has been or is suspect of having arthritis.

In some embodiments, the disclosure relates to a method of treating allergies by administering at least one or a plurality of compositions disclosed herein comprising PIF peptide, an analog thereof, or a pharmaceutically acceptable salt thereof.

In some embodiments, the disclosure relates to a method of treating allergies by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating allergies by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of allergies.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of allergies.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of allergies.

In some embodiments, the disclosure relates to a method of inducing an immunomodulation effect in a subject in need thereof, when subject has been or is suspect of having allergies.

In some embodiments, the disclosure relates to a method of treating asthma by administering at least one or a plurality of compositions disclosed herein comprising PIF peptide, an analog thereof, or a pharmaceutically acceptable salt thereof.

In some embodiments, the disclosure relates to a method of treating asthma by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating asthma by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of asthma.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of asthma.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of asthma.

In some embodiments, the disclosure relates to a method of inducing an immunomodulation effect in a subject in need thereof, when subject has been or is suspect of having asthma.

In some embodiments, the disclosure relates to a method of treating eczema by administering at least one or a plurality of compositions disclosed herein comprising PIF peptide, an analog thereof, or a pharmaceutically acceptable salt thereof.

In some embodiments, the disclosure relates to a method of treating eczema by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating eczema by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of eczema.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of eczema.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of eczema.

In some embodiments, the disclosure relates to a method of inducing an immunomodulation effect in a subject in need thereof, when subject has been or is suspect of having eczema.

In some embodiments, the disclosure relates to a method of treating urticaria by administering at least one or a plurality of compositions disclosed herein comprising PIF peptide, an analog thereof, or a pharmaceutically acceptable salt thereof.

In some embodiments, the disclosure relates to a method of treating urticaria by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating urticaria by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of urticaria.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of urticaria.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of urticaria.

In some embodiments, the disclosure relates to a method of inducing an immunomodulation effect in a subject in need thereof, when subject has been or is suspect of having urticaria.

In some embodiments, the disclosure relates to a method of treating atopic dermatitis by administering at least one or a plurality of compositions disclosed herein comprising PIF peptide, an analog thereof, or a pharmaceutically acceptable salt thereof.

In some embodiments, the disclosure relates to a method of treating atopic dermatitis by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating atopic dermatitis by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of atopic dermatitis.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of atopic dermatitis.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of atopic dermatitis.

In some embodiments, the disclosure relates to a method of inducing an immunomodulation effect in a subject in need thereof, when subject has been or is suspect of having atopic dermatitis.

In some embodiments, the disclosure relates to a method of treating bronchopulminary dysplasia by administering at least one or a plurality of compositions disclosed herein comprising PIF peptide, an analog thereof, or a pharmaceutically acceptable salt thereof.

In some embodiments, the disclosure relates to a method of treating bronchopulminary dysplasia by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating bronchopulminary dysplasia by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of bronchopulminary dysplasia.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of bronchopulminary dysplasia.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of bronchopulminary dysplasia.

In some embodiments, the disclosure relates to a method of inducing an immunomodulation effect in a subject in need thereof, when subject has been or is suspect of having bronchopulminary dysplasia.

In some embodiments, the disclosure relates to a method of treating Gaucher's disease by administering at least one or a plurality of compositions disclosed herein comprising PIF peptide, an analog thereof, or a pharmaceutically acceptable salt thereof.

In some embodiments, the disclosure relates to a method of treating Gaucher's disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating Gaucher's disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of Gaucher's disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of Gaucher's disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of Gaucher's disease.

In some embodiments, the disclosure relates to a method of inducing an immunomodulation effect in a subject in need thereof, when subject has been or is suspect of having Gaucher's disease.

In some embodiments, the disclosure relates to a method of treating auto-immune disease by administering at least one or a plurality of compositions disclosed herein comprising PIF peptide, an analog thereof, or a pharmaceutically acceptable salt thereof.

In some embodiments, the disclosure relates to a method of treating auto-immune disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating auto-immune disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of auto-immune disease in a subject in need thereof.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of auto-immune disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of auto-immune disease.

In some embodiments, the disclosure relates to a method of inducing an immunomodulation effect in a subject in need thereof, when subject has been or is suspect of having auto-immune disease.

In some embodiments, the disclosure relates to a method of treating collagen disease by administering at least one or a plurality of compositions disclosed herein comprising PIF peptide, an analog thereof, or a pharmaceutically acceptable salt thereof.

In some embodiments, the disclosure relates to a method of treating collagen disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating collagen disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of collagen disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of collagen disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of collagen disease.

In some embodiments, the disclosure relates to a method of inducing an immunomodulation effect in a subject in need thereof, when subject has been or is suspect of having collagen disease.

In some embodiments, the disclosure relates to a method of treating connective tissue disease by administering at least one or a plurality of compositions disclosed herein comprising PIF peptide, an analog thereof, or a pharmaceutically acceptable salt thereof.

In some embodiments, the disclosure relates to a method of treating connective tissue disease by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating connective tissue disease by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of connective tissue disease.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of connective tissue disease.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of connective tissue disease.

In some embodiments, the disclosure relates to a method of inducing an immunomodulation effect in a subject in need thereof, when subject has been or is suspect of having connective tissue disease.

In some embodiments, the disclosure relates to a method of treating inflammation disorders by administering at least one or a plurality of compositions disclosed herein comprising PIF peptide, an analog thereof, or a pharmaceutically acceptable salt thereof.

In some embodiments, the disclosure relates to a method of treating inflammation disorders by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating inflammation disorders by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of inflammation disorders.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of inflammation disorders.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of inflammation disorders.

In some embodiments, the disclosure relates to a method of inducing an immunomodulation effect in a subject in need thereof, when subject has been or is suspect of having inflammation disorders.

In some embodiments, the disclosure relates to a method of treating repetitive strain injuries by administering at least one or a plurality of compositions disclosed herein comprising PIF peptide, an analog thereof, or a pharmaceutically acceptable salt thereof.

In some embodiments, the disclosure relates to a method of treating repetitive strain injuries by administering a therapeutically effective amount or dose of one or a plurality of compositions disclosed herein comprising at least one PIF peptide, an analog thereof, or a pharmaceutically acceptable salt thereof.

In some embodiments, the disclosure relates to a method of treating repetitive strain injuries by administration of a pharmaceutical composition comprising a therapeutically effective amount or dose of at least one PIF peptide, an analog thereof, or a pharmaceutically acceptable salt thereof, and a pharmaceutically acceptable carrier.

In some embodiments, the disclosure relates to a pharmaceutical composition comprising a therapeutically effective amount or dose of at least one PIF peptide, an analog thereof, or a pharmaceutically acceptable salt thereof, and a pharmaceutically acceptable carrier for the treatment of repetitive strain injuries.

In some embodiments, the disclosure relates to the use of a therapeutically effective amount or dose of any one or plurality of compositions disclosed herein comprising at least one PIF peptide, an analog thereof, or a pharmaceutically acceptable salt thereof, and a pharmaceutically acceptable carrier in the manufacture of a medicament for the treatment of repetitive strain injuries.

In some embodiments, the disclosure relates to the use of a pharmaceutical composition comprising a therapeutically effective amount or dose at least one PIF peptide, an analog thereof, or a pharmaceutically acceptable salt thereof, and a pharmaceutically acceptable carrier in the manufacture of a medicament for the treatment of repetitive strain injuries.

In some embodiments, the disclosure relates to a method of inducing an immunomodulation effect in a subject in need thereof, when subject has been or is suspect of having repetitive strain injuries.

Kits

According to some embodiments of the invention, the formulation may be supplied as part of a kit. In some embodiments, the kit comprises comprising a PIF peptide and/or a PIF analog or pharmaceutically acceptable salt thereof, the PIF peptide and/or a PIF analog or pharmaceutically acceptable salt thereof comprises a non-natural amino acid or is at least 70% homologous to SEQ ID NO: 1. In some embodiments, the kit comprises comprising a PIF peptide and/or a PIF analog or pharmaceutically acceptable salt thereof, the PIF peptide and/or a PIF analog or pharmaceutically acceptable salt thereof comprises a non-natural amino acid or is at least 70% homologous to SEQ ID NO: 2. In some embodiments, the kit comprises comprising a PIF peptide and/or a PIF analog or pharmaceutically acceptable salt thereof, the PIF peptide and/or a PIF analog or pharmaceutically acceptable salt thereof comprises a non-natural amino acid or is at least 70% homologous to SEQ ID NO: 3. In some embodiments, the kit comprises comprising a PIF peptide and/or a PIF analog or pharmaceutically acceptable salt thereof, the PIF peptide and/or a PIF analog or pharmaceutically acceptable salt thereof comprises a non-natural amino acid or is at least 70% homologous to SEQ ID NO: 4. In some embodiments, the kit comprises comprising a PIF peptide and/or a PIF analog or pharmaceutically acceptable salt thereof, the PIF peptide and/or a PIF analog or pharmaceutically acceptable salt thereof comprises a non-natural amino acid or is at least 70% homologous to SEQ ID NO: 5. In some embodiments, the kit comprises comprising a PIF peptide and/or a PIF analog or pharmaceutically acceptable salt thereof, the PIF peptide and/or a PIF analog or pharmaceutically acceptable salt thereof comprises a non-natural amino acid or is at least 70% homologous to SEQ ID NO: 6. In some embodiments, the kit comprises comprising a PIF peptide and/or a PIF analog or pharmaceutically acceptable salt thereof, the PIF peptide and/or a PIF analog or pharmaceutically acceptable salt thereof comprises a non-natural amino acid or is at least 70% homologous to SEQ ID NO: 7. In some embodiments, the kit comprises comprising a PIF peptide and/or a PIF analog or pharmaceutically acceptable salt thereof, the PIF peptide and/or a PIF analog or pharmaceutically acceptable salt thereof comprises a non-natural amino acid or is at least 70% homologous to SEQ ID NO: 8. In some embodiments, the kit comprises comprising a PIF peptide and/or a PIF analog or pharmaceutically acceptable salt thereof, the PIF peptide and/or a PIF analog or pharmaceutically acceptable salt thereof comprises a non-natural amino acid or is at least 70% homologous to SEQ ID NO: 9. In some embodiments, the kit comprises comprising a PIF peptide and/or a PIF analog or pharmaceutically acceptable salt thereof, the PIF peptide and/or a PIF analog or pharmaceutically acceptable salt thereof comprises a non-natural amino acid or is at least 70% homologous to SEQ ID NO: 10. In another embodiment, the kit comprises a pharmaceutically acceptable salt of an analog with a rehydration mixture. In another embodiment, the pharmaceutically acceptable salt of an analog are in one container while the rehydration mixture is in a second container. The rehydration mixture may be supplied in dry form, to which water or other liquid solvent may be added to form a suspension or solution prior to administration. Rehydration mixtures are mixtures designed to solubilize a lyophilized, insoluble salt of the invention prior to administration of the composition to a subject takes at least one dose of a purgative. In another embodiment, the kit comprises a pharmaceutically acceptable salt in orally available pill form.

The kit may contain two or more containers, packs, or dispensers together with instructions for preparation and administration. In some embodiments, the kit comprises at least one container comprising the pharmaceutical composition or compositions described herein and a second container comprising a means for delivery of the compositions such as a syringe. In some embodiments, the kit comprises a composition comprising an analog in solution or lyophilized or dried and accompanied by a rehydration mixture. In some embodiments, the analog and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

In another embodiment, a packaged kit is provided that contains the pharmaceutical formulation to be administered, i.e., a pharmaceutical formulation containing PIF peptide and/or a PIF analog or pharmaceutically acceptable salt thereof, a container (e.g., a vial, a bottle, a pouch, an envelope, a can, a tube, an atomizer, an aerosol can, etc.), optionally sealed, for housing the formulation during storage and prior to use, and instructions for carrying out drug administration in a manner effective to treat any one or more of the indications disclosed herein. The instructions will typically be written instructions on a package insert, a label, and/or on other components of the kit.

Depending on the type of formulation and the intended mode of administration, the kit may also include a device for administering the formulation (e.g., a transdermal delivery device). The administration device may be a dropper, a swab, a stick, or the nozzle or outlet of an atomizer or aerosol can. The formulation may be any suitable formulation as described herein. For example, the formulation may be an oral dosage form containing a unit dosage of the active agent, or a gel or ointment contained within a tube. The kit may contain multiple formulations of different dosages of the same agent. The kit may also contain multiple formulations of different active agents.

The present kits will also typically include means for packaging the individual kit components, i.e., the pharmaceutical dosage forms, the administration device (if included), and the written instructions for use. Such packaging means may take the form of a cardboard or paper box, a plastic or foil pouch, etc.

This disclosure and embodiments illustrating the method and materials used may be further understood by reference to the following non-limiting examples. Examples are intended to create a context to present neurotrauma as an integrated multiprong disease and PIF's ability to address the disease locally and systemically addressing its cause not only consequences as they were to become apparent.

```
                                        SEQ ID NO: 12
MRYRLAWLLH PALPSTFRSV LGARLPPPER LCGFQKKTYS

KMNNPAIKRI GNHITKSPED KREYRGLELA NGIKVLLISD

PTTDKSSAAL DVHIGSLSDP PNIAGLSHFC EHMLFLGTKK

YPKENEYSQF LSEHAGSSNA FTSGEHTNYY FDVSHEHLEG

ALDRFAQFFL CPLFDESCKD REVNAVDSEH EKNVMNDAWR

LFQLEKATGN PKHPFSKFGT GNKYTLETRP NQEGIDVRQE

LLKFHSAYYS SNLMAVCVLG RESLDDLTNL VVKLFSEVEN

KNVPLPEFPE HPFQEEHLKQ LYKIVPIKDI RNLYVTFPIP
```

```
                     -continued
DLQKYYKSNP GHYLGHLIGH EGPGSLLSEL KSKGWVNTLV

GGQKEGARGF MFFIINVDLT EEGLLHVEDI ILHMFQYIQK

LRAEGPQEWV FQECKDLNAV AFRFKDKERP RGYTSKIAGI

LHYYPLEEVL TAEYLLEEFR PDLIEMVLDK LRPENVRVAI

VSKSFEGKTD RTEEWYGTQY KQEAIPDEVI KKWQNADLNG

KFKLPTKNEF IPTNFEILPL EKEATPYPAL IKDTAMSKLW

FKQDDKFFLP KACLNFEFFS PFAYVDPLHC NMAYLYLELL

KDSLNEYAYA AELAGLSYDL QNTIYGMYLS VKGYNDKQPI

LLKKIIEKMA TFEIDEKRFE IIKEAYMRSL NNFRAEQPHQ

HAMYYLRLLM TEVAWTKDEL KEALDDVTLP RLKAFIPQLL

SRLHIEALLH GNITKQAALG IMQMVEDTLI EHAHTKPLLP

SQLVRYREVQ LPDRGWFVYQ QRNEVHNNCG IEIYYQTDMQ

STSENMFLEL FCQIISEPCF NTLRTKEQLG YIVFSGPRRA

NGIQGLRFII QSEKPPHYLE SRVEAFLITM EKSIEDMTEE

AFQKHIQALA IRRLDKPKKL SAECAKYWGE IISQQYNFDR

DNTEVAYLKT LTKEDIIKFY KEMLAVDAPR RHKVSVHVL

REMDSCPVVG EFPCQNDINL SQAPALPQPE VIQNMTEFKR

GLPLFPLVKP HINFMAAKL
```

Example 1: sPIF has Similar Binding to Lymphocytes Compared to Standard PIF

The sPIF sequences provided herein (SEQ ID NOs: 1-10) are non-naturally occurring mutants of PIF. In order to determine if they sPIF sequences provided herein have similar properties to PIF, FITC-PIF assays was performed to examine sPIF binding to monocytes. SEQ ID NO: 8 and SEQ ID NO: 10 were compared to natural PIF in binding to CD11b (macrophage) and CD19 (B cell) monocytes.

TABLE 2

| PIF v sPIF binding | | |
|---|---|---|
| PIF type | CD11b % | CD19 % |
| SEQ ID NO: 8 | 35.48% | 5.60% |
| control PIF | 27.94% | 3.23% |
| SEQ ID NO: 10 | 33.54% | 5.90% |
| control PIF | 27.11% | 4.34% |

The sPIF sequences SEQ ID NOs: 8 and 10 showed higher binding affinity to both CD11b and CD19 monocytes. This result lends support to the idea that the sPIF sequences provided here (SEQ ID NOs: 1-10) may bind to PIF receptors at least as well as, if not better than, native PIF.

Example 2: sPIF Therapy to Arrest and/or Reverse Both Acute and Chronic Neurotrauma Preimplantation Factor (PIF) is a 15 amino-acid peptide produced by solid phase synthesis at human grade quality (sPIF). [3-6] Following severe neurotrauma, sPIF reduces inflammation, while promoting myelin repair and nerve regeneration, also reverses advanced paralysis and severe neurologic injury through local and systemic protection. PIF targets directly the CNS and promotes endogenous stems cells proliferation and differentiation. PIF could be a safe and effective drug to address acute and long-term neurotrauma sequela. Due to its high safety profile and comprehensive preclinical results, [7-14] sPIF is currently FAST-TRACK awarded, FDA approved University-sponsored clinical trial for autoimmune disorder. (<ClinicalTrials.gov>NCT02239562). PIF could be a safe and effective drug to address acute and long-term neurotrauma sequela. Overall, PIF could be a novel approach for the comprehensive management of neurotrauma from acute to the chronic phase integrating both local and systemic protection.

Preliminary Data

Pregnancy perspective: PIF exerts broad neurotrophic and neuroprotective effects. Native PIF is endogenously expressed by the embryo/fetus and placenta and its presence in circulation is associated with favorable pregnancy outcome (absence in non-viable embryos). Starting post fertilization PIF plays a determining role to create maternal tolerance without immune suppression, regulating immunity, inflammation and transplant acceptance. In short, PIF comprehensively regulates inflammation, immunity and transplant acceptance. PIF specifically promotes neural development and protects against maternal adverse environment. PIF targets the embryo to reduce oxidative stress and protein misfolding, both critical elements of neurotrauma. In vivo PIF reduces spontaneous and LPS induced pregnancy loss decreasing placental inflammation.[3-5, 15, 16-22] Synthetic PIF (sPIF) successfully translates pregnancy-induced native's peptide effect, including its beneficial neuroprotective properties to clinically relevant models outside pregnancy. As such PIF presents qualities for a comprehensive neurotrauma preventative and therapeutic. PIF-based therapy is a paradigm-shift approach regulating inflammation locally and systemically, early or later, and in acute or chronic neurotrauma. The data comprehensively address the unmet need. Therefore herein, the following examples are representative of a comprehensive, synergizing therapeutic platform.

Results

PIF Targets and Regulates Human Immune Cells to Create Th2/Th1 Bias—In Vivo PIF Reduces Activated Macrophages/Neutrophil Extravasation Systemically.

The resulting systemic inflammatory response is a key for both short and long term neurotrauma. sPIF orchestrates global anti-inflammatory effects in human mononuclear cells (PBMCs) (Barnea, et al. 2012, Roussev et al. 2013, Barnea et al. 2015). Preserving basal immunity sPIF blocks mixed lymphocyte reaction (MLR) and activated PBMCs proliferation. By increasing IL-10 (rather than IFN-γ expression) sPIF may counteract several pro-inflammatory (TNF-α, IFN-γ IL-12B) macrophage activators (Barnea, et al. 2012). sPIF also reduces NK cells cytotoxicity by inhibiting pro-inflammatory CD69 expression. PIF targets systemic immunity independent of early Ca++ mobilization hallmark of immune suppressive drugs.

sPIF direct anti-inflammatory effect was tested in vivo. In a murine model following LPS-induced peritonitis sPIF injection reduced macrophage migration. Neutrophil extravasation was reduced in post-chemically induced peritonitis. (Karl-Heintz et al. 2015). In addition in a cremasteric muscle induced inflammation model, PIF reduces neutrophils rolling and extravasdation post TNF-induced inflammation. sPIF targets Kv1.3b the K+ alpha pore acts as competitive inhibitor of cortisone. sPIF acts as cortisone to reduce K+ flux which was confirmed in vivo (Karl-Heintz et al. 2015). The Kv1.3 is critical for neurotransmission. sPIF regulates Ca+ flux through the K+ flux, thereby not acting as an immune suppressor as cortisone does. Due to peptide's small size and its high flexibility sPIF through its core R-I-K-P sequence targets multiple proteins. This is complemented by changes in protein targets folding structure which can affect sPIF binding. Among them, sPIF targets insulin degrading enzyme when protein is attached to insulin thereby regulates the growth factor function. IDE is critical for Alzheimer's disease—prevents b-amyloid accumulation. PIF reduces oxidative stress and protein misfolding by targeting protein-disulfide isomerase and heat shock protein 70 (Barnea et al. 2104, Barnea et al. 2015) Almogi-Hazan et al. 2014). Thus sPIF acts to regulate systemic immunity restoring homeostasis. As such sPIF has a critical integrating anti-inflammatory role.

sPIF: A Single Amino Acid Mutation Leads to Loss of Activity in Both Neural Cells and Systemic Immune Cells— Relevance of sPIF for Neuroprotection.

Figure 2:
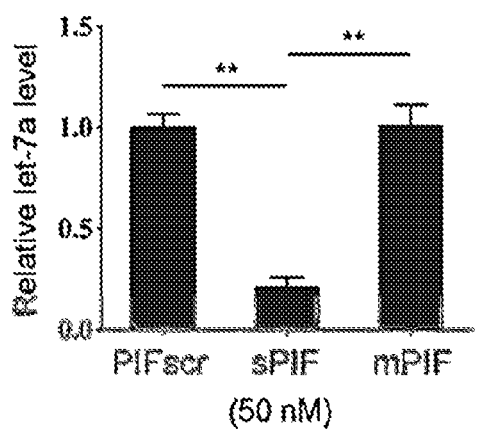
FIG. 2 depicts a measurement of let-7a levels in two identified cell lines (A: BV-2 cells; B: N2a cells) after exposure of the cells to a scrambled PIF negative control sequence (PIFscr), a synthetic PIF sequence (sPIF), and a mutated PIF sequence (mPIF).
Figure 2:
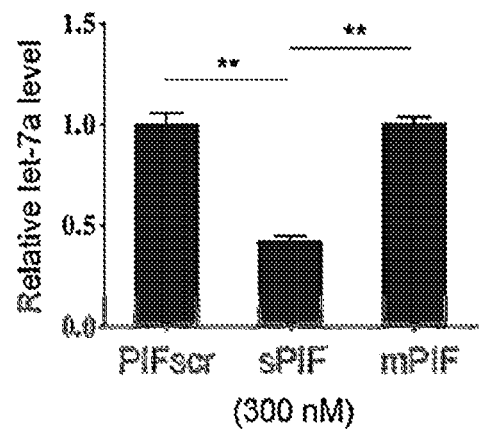
Figure 3:
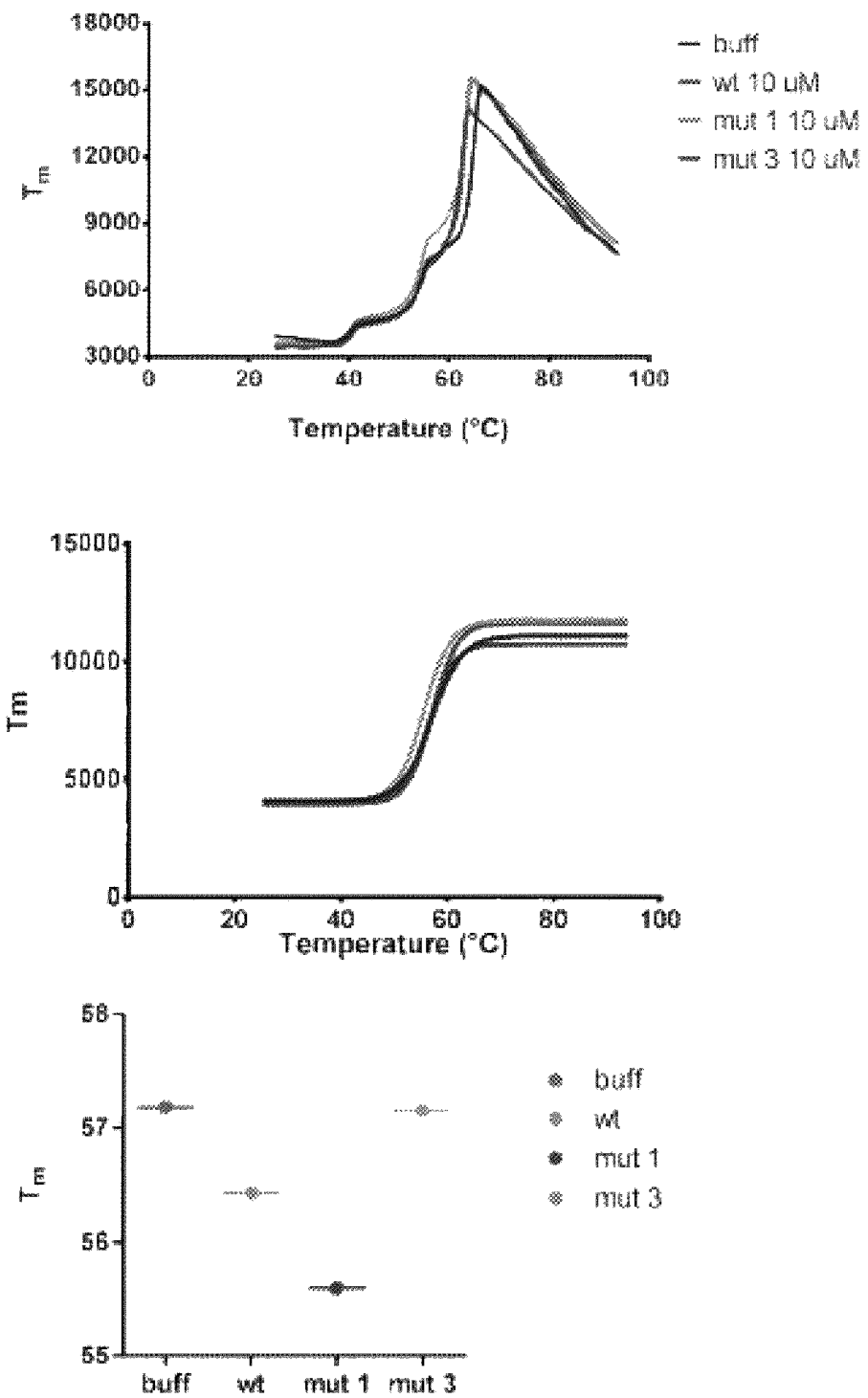
FIG. 3 depicts a fluorescent based thermal shift assay, showing the binding of two PIF mutants to the insulin degrading enzyme (IDE). Concentrations of the ligands 10 uM and 1 uM of the receptor, buffer consisting of 10 mM HEPES-HCL, 150 mM MaCl, and protein folding sensitive dye SyO 1:1000. The PIF(mutant-1) ("mut 1") had a decreased Tm compared to the PIF(wt) ("wt"), suggesting higher affinity of binding to the receptor, while PIF(mutant-3) ("mut 3") had an actually increased Tm, compared to the PIF(wt), suggesting decreased binding affinity of this mutant to the IDE.
Figure 4:
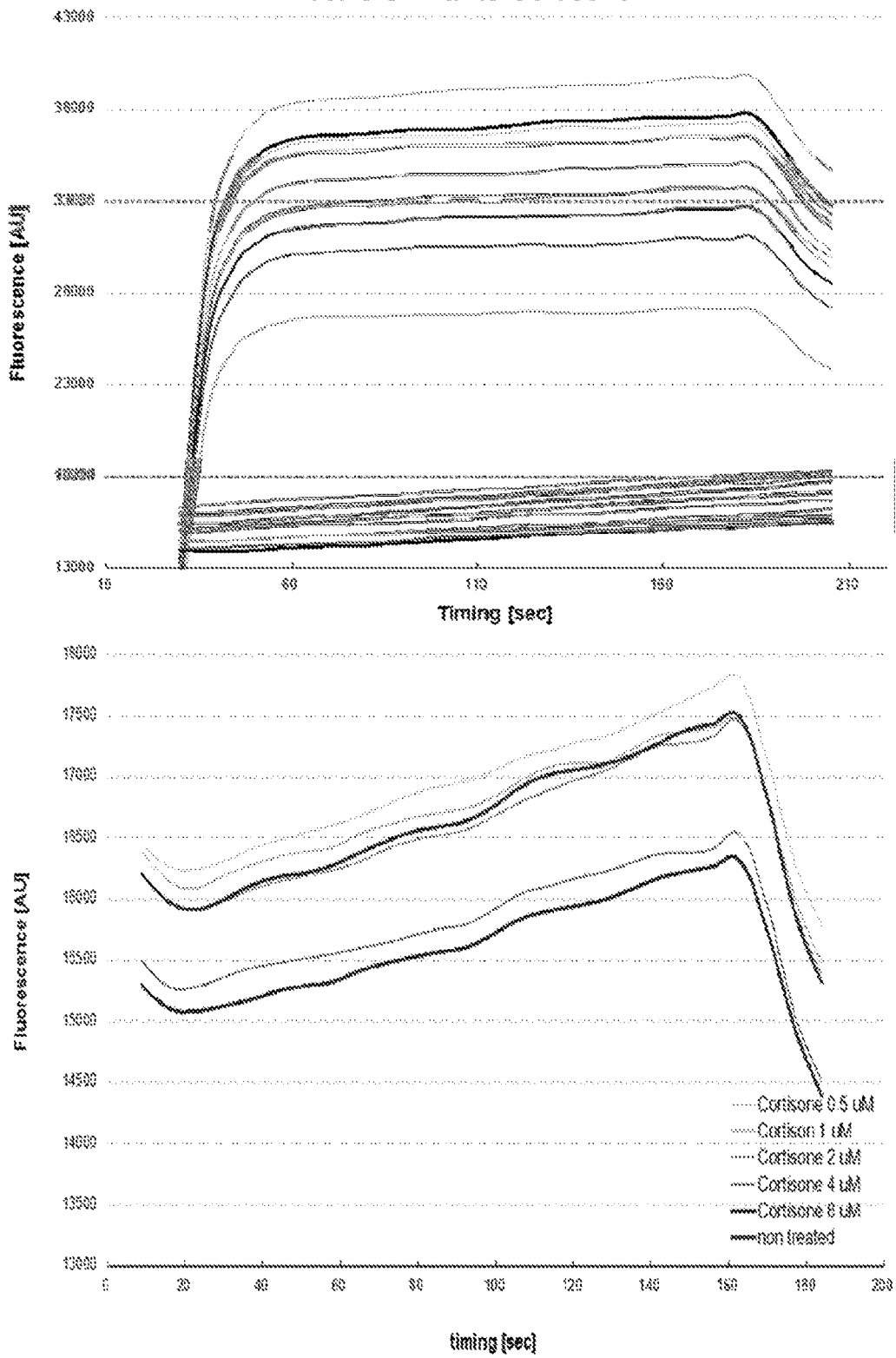
FIG. 4 depicts a comparison of fluorescence measurements correlating the effect of PIF, PIF mutants (1 or 3) or cortisone on K+ flux inhibition in Jurkat T-cells.

Modifications of the sPIF sequence lead to altered biological activity. sPIF binding to PDI was compared to scrambled PIF (the same amino acid in random sequence). Due to the modified peptide structure rigidity, its interaction with PDI target was greatly reduced. (FIG. 2). Using Kv1.3b (potassium channel beta) as a binding target, the modifications of a single amino acid of sPIF were assessed. The data showed that most the changes at the 4 and 6 positions may be relevant for biologic activity. (FIG. 3). Thermal shift assay for insulin degrading enzyme (IDE), a zinc metallopeptidase that degrades intracellular insulin demonstrated that mut-1 likely increases the biologic activity since it has a reduced thermal shift when compared with the wild type PIF. On the other hand, the mut-3 PIF activity was decreased which was also confirmed in lack of effect on let-7 micrtoRNA in both microglia as well as neural cell lines. Consequently sPIF effect was examined in cell based systems. Using the Jurkat cells line the effect of sPIF was compared to the mutated sPIF (Mut-3 and Mut 1) as it reflected on K+ flux. Data demonstrated that the effect was significant reducing the K+ flux as compared with control. Both mutated sPIF at high doses (control) had no effect. (FIG. 4). In addition when compared to cortisone, sPIF had a similar inhibitory effect on K+ flux. Thus dependent on the target Kv1.3 or IDE the mutated PIF-1 can have a target-specific effect which can also translate to diverse biological activity.

sPIF Reduces Gaucher, and Gaucher-Like Disease—Mucopolysaccharidosis Induced Systemic Inflammation In Vitro.

Figure 23:
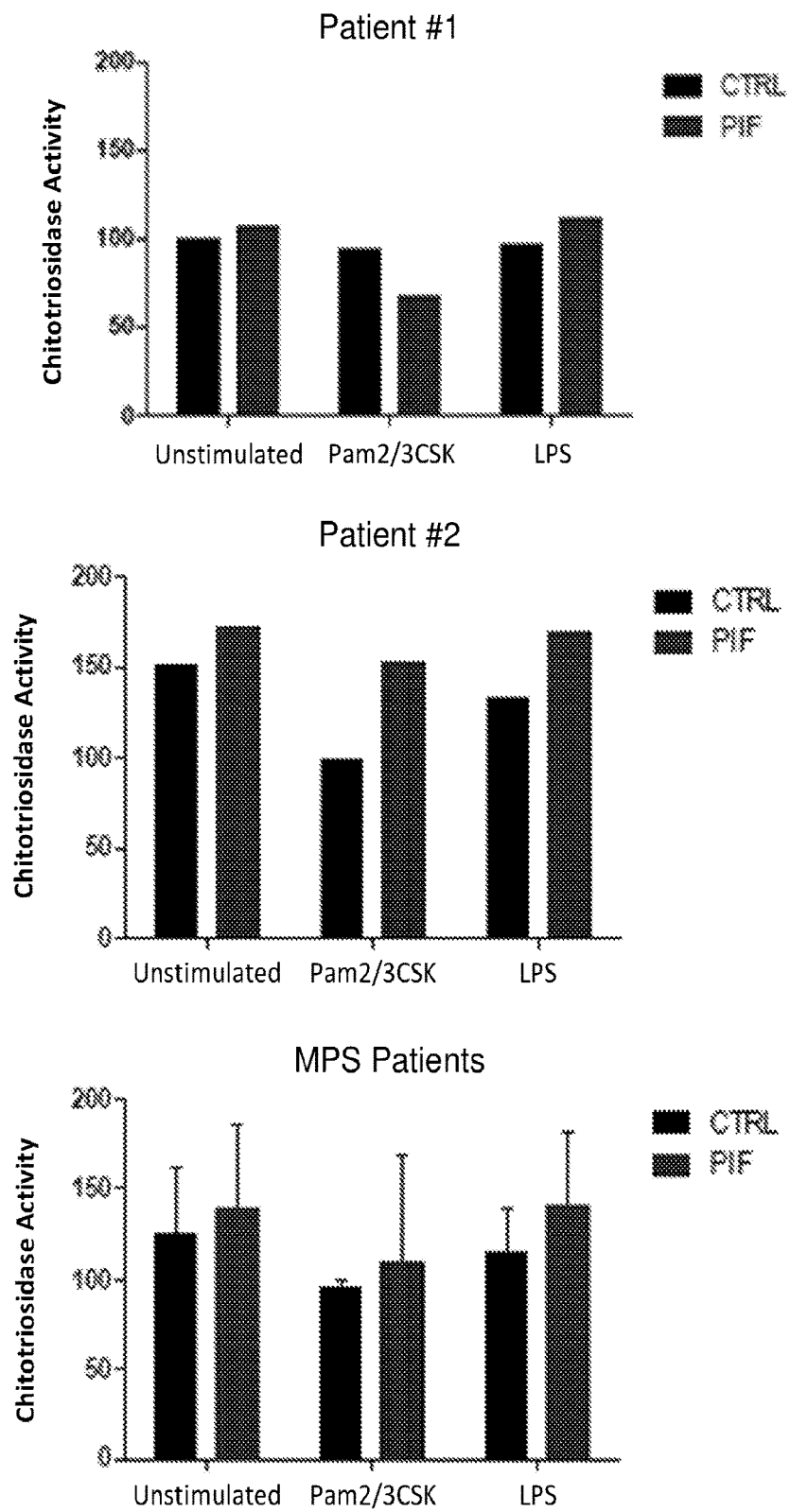
FIG. 23 depicts a measurement of enzymatic activity in a Gaucher's disease model. PIF was able to increase the enzymatic defect of mucopolysaccharidosis.

Gaucher Disease (typically diagnosed in childhood) is defined as a rare hereditary disorder of lipid metabolism caused by an enzyme deficiency and characterized by enlargement of the spleen and liver, bone lesions, and neurological impairment. Beyond the potential neural dysfunction (local), patients with the disease can also have systemic inflammation. Whether PIF can alter immune response in children with Gaucher disease was examined. Blood collected from two children PBMCs were separated and the effect of PIF also or following activation by LPS was determined. PIF increased chitotriosidase levels as compared to unstimulated, Pam2/3csk (marker inducer) and LPS-treated PBMC. (FIG. 23). PIF reduced LPS-induced chitotriosidase activity reflecting an anti-inflammatory response. This data substantiates that sPIF may control systemic manifestations of central neuroinflammatory disease thereby reducing the resulting central inflammatory response.

sPIF Reverses Brain Injury HIE Model: Acute-Neurotrauma Intervention.

Acute injury blunt/blast/penetrating injury of the brain and spinal cord can create a compromised blood supply, strong inflammatory response (activated microglia, oligodendrocytes) and decreased oxygen supply. In addition the CNS may initiate an infectious process, if the wound is severe. Following acute-neurotrauma, immediate specialized care is frequently not available in military setting. In civilian cases rapid evacuation to a hospital can take place. Once the patient is in the hospital, if the neuroinjury is severe, neurosurgery has to be involved. However mostly supportive measures are initiated which are followed by long-term rehabilitation. Thus, an acute intervention to mitigate initiation and uncontrolled progression of inflammation caused by neurotrauma would be a major breakthrough.

For effective immediate intervention sPIF is readily available, stable in harsh environment (RT) and has rapid and sustained action. The hypoxic ischemic (HIE) model provides a clinically relevant model to examine sPIF efficacy in acute neurotrauma setting. The HIE model is associated with high morbidity and mortality. The HIE clinically-relevant model is three-prong: 1. ligation of the carotid artery in one side, 2. exposure to low oxygen for several minutes and 3. LPS-induced inflammation. Thus, HIE closely represents an acute/severe CNS injury.

Figure 5A:
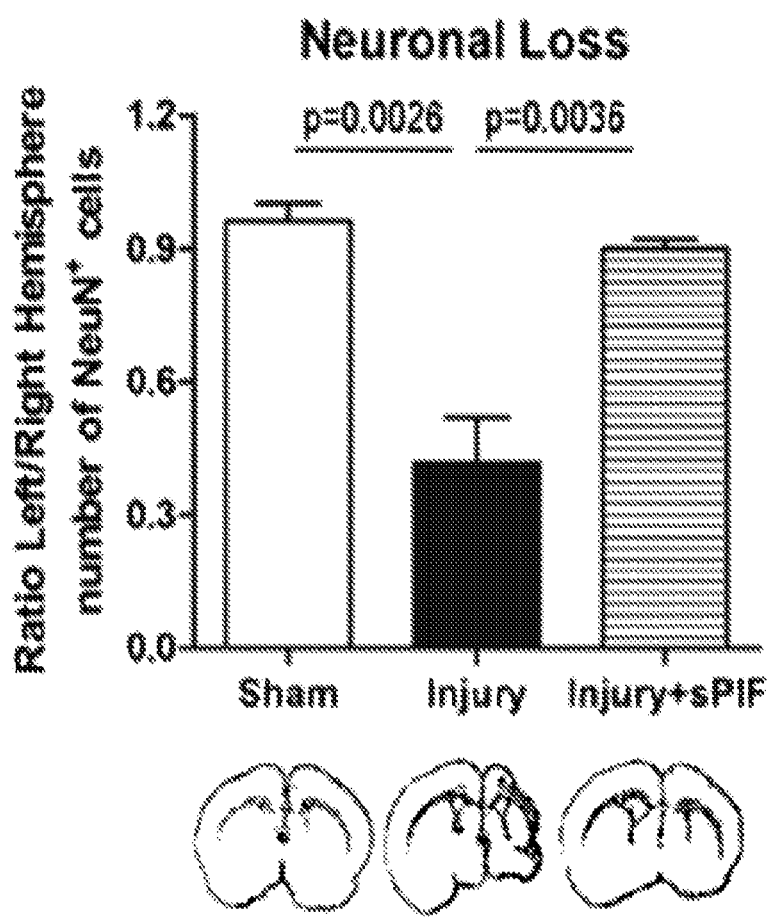
FIGS. 5A-5G depict sPIF treatment results and proposed molecular pathways.
Figure 5B:
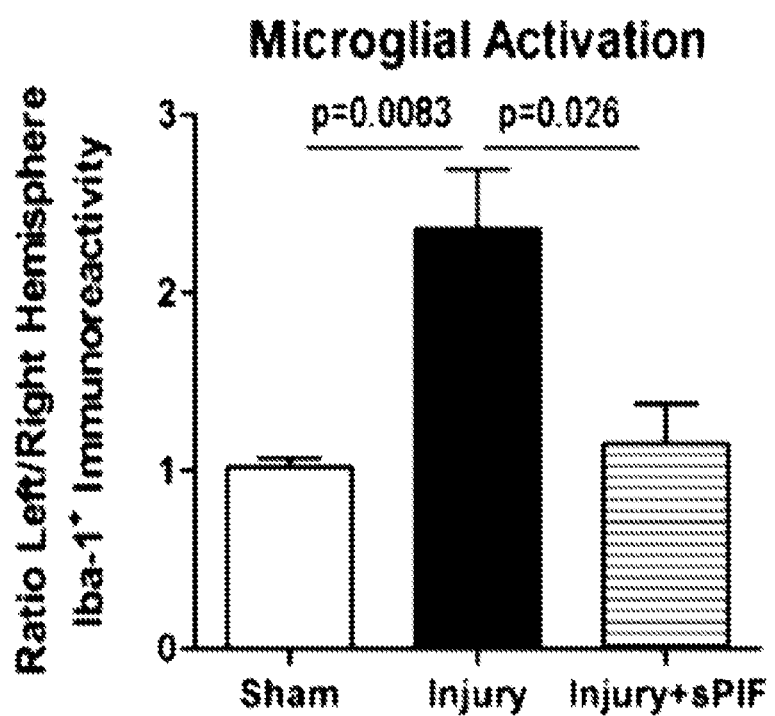

To mimic clinical scenarios seen frequently in the battlefield and sometimes with civilians if rapid intervention is not available subcutaneous sPIF therapy was started only 3 days post-injury and has lasted only for 6 days. sPIF led to significant neuroprotection assessed clinically and revealing effect on pathways relevant for neurologic disorders and specific to CNS injury. Remarkably, sPIF reduces brain cells death, reverses neuronal loss and restores proper cortical architecture and reduced microglial activation (FIGS. 5A, 5B) The effect of sPIF was direct (or local) targeting both microglia (macrophages) and neural cells. It is important to remark that in order for sPIF to act since one carotid artery was obstructed therefore to reverse neuronal injury sPIF had to pass from the apparently healthy to the injured hemisphere. Thus we observed sPIF to traverse the BBB intact.

Figure 5C:
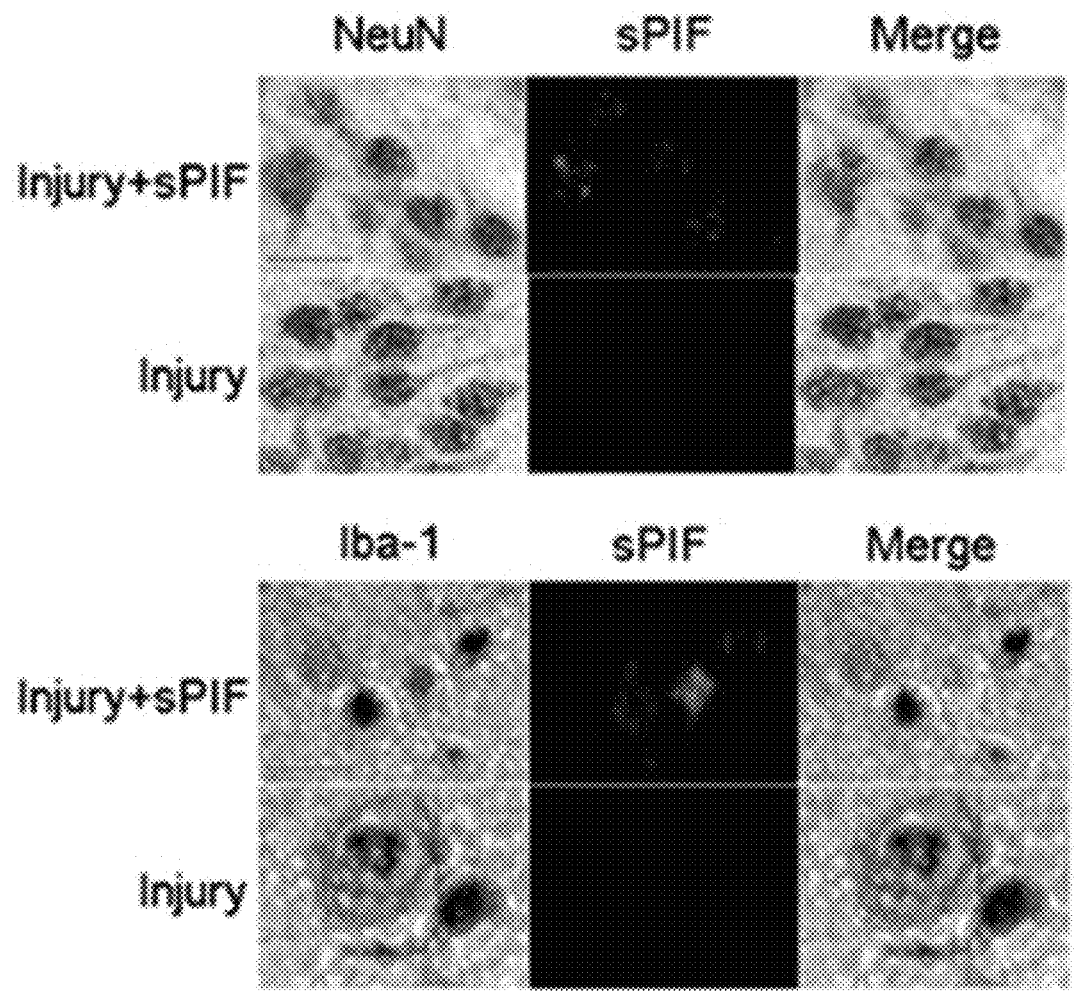
Figure 5D:
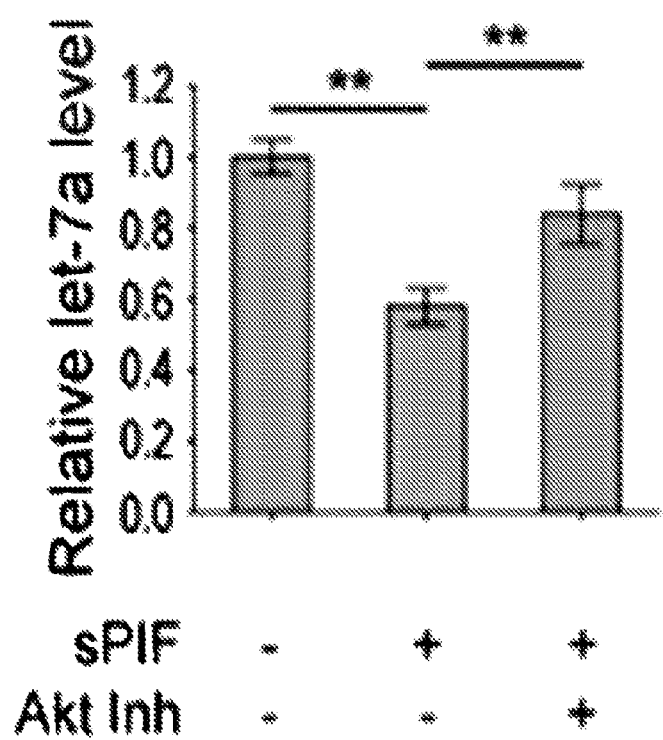
Figure 5E:
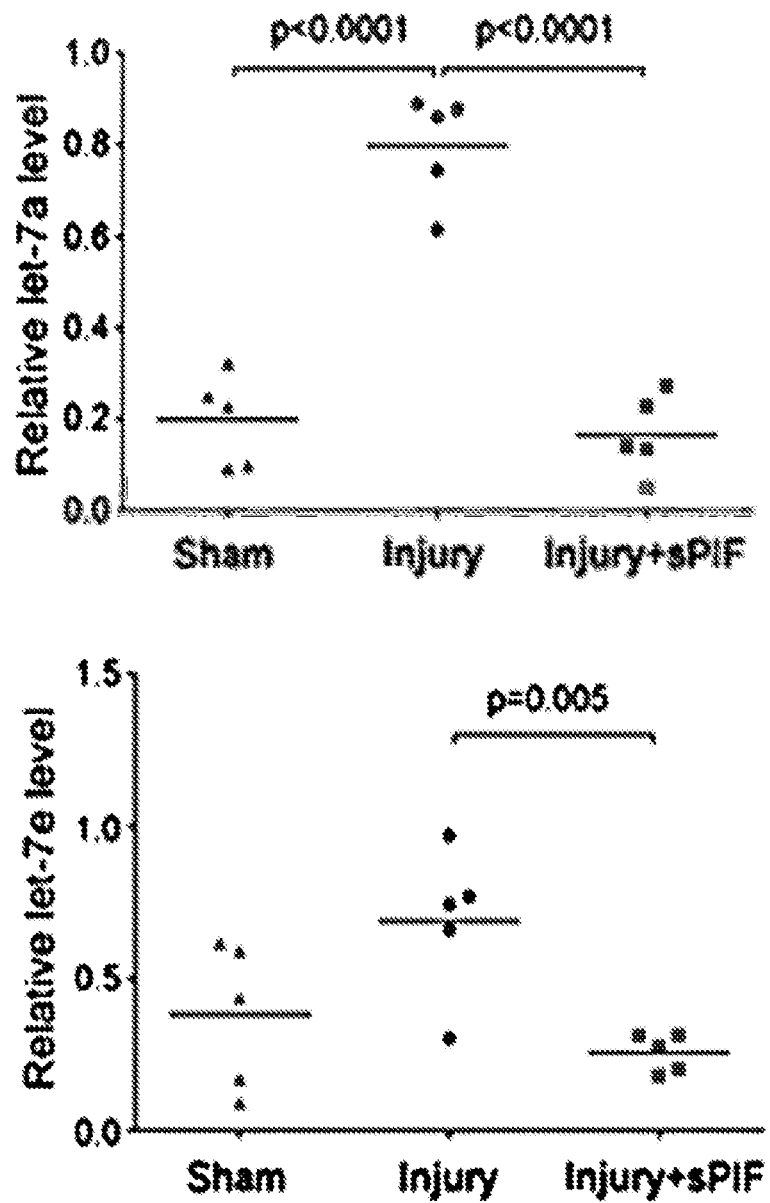
Figure 5F:
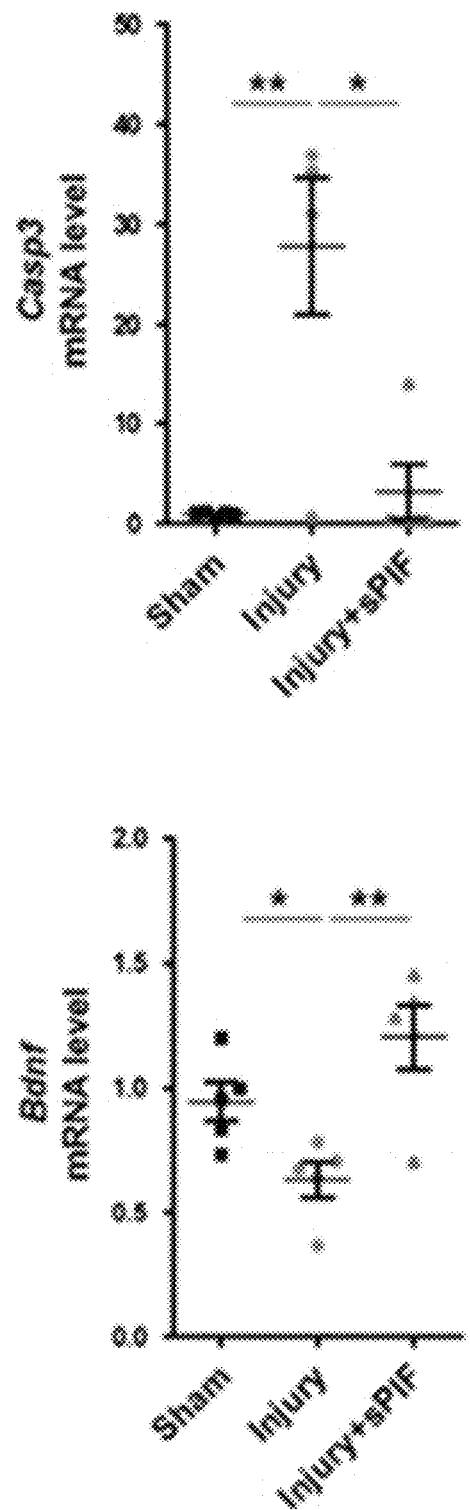
Figure 5G:
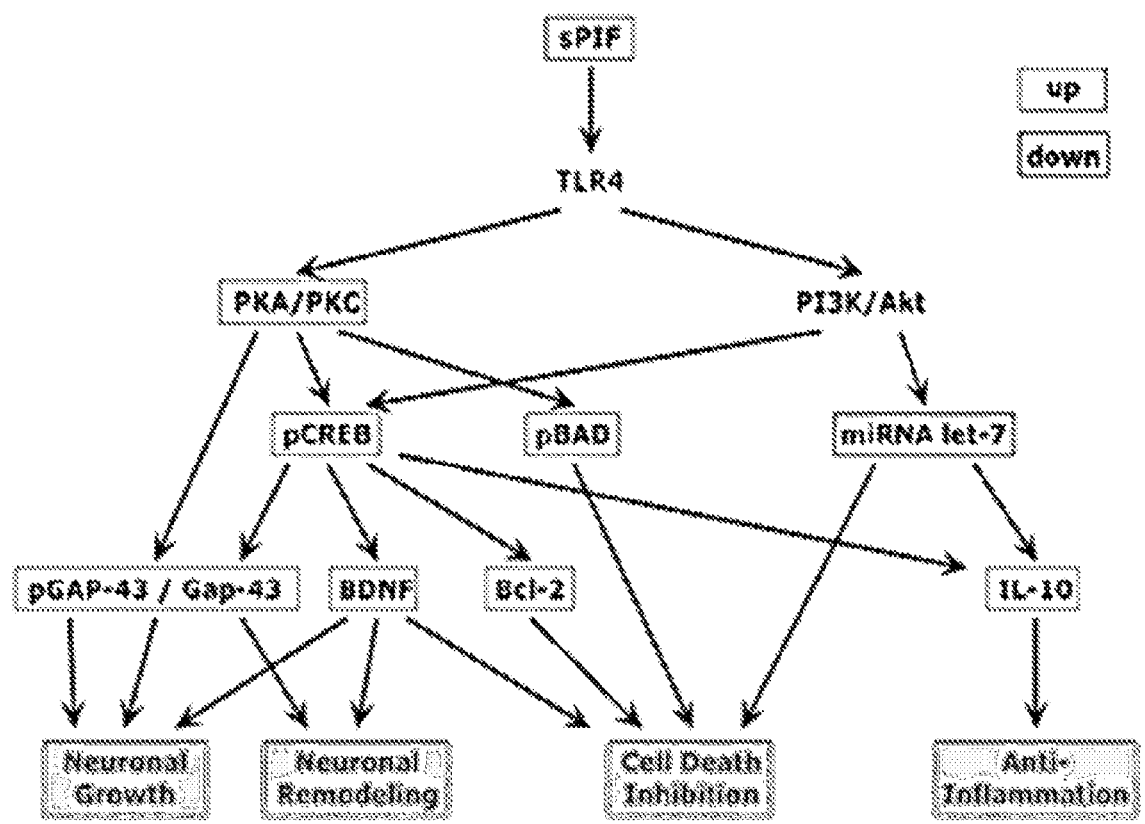

This direct effect on target cells was confirmed by targeting microglia and neuron cell line (Neu) in vitro (FIGS. 5C, D). Two major complementary mechanisms of clear relevance support sPIF induced neuroprotection; namely reduced pro-apoptotic let-7microRNA coupled with regulation of phosphorylated PKC/PKA pathways. sPIF reduced let-7 while increasing IL-10 expression—effects were TLR4/PI3-AKT dependent (FIGS. 5C-5E). sPIF activates (PKA)/(PKC) signaling, leading to increased phosphorylation of major neuroprotective substrates (GAP-43, BAD, and CREB). Phosphorylated CREB in turn facilitates expression of (Gap43, Bdnf and Bcl2) (FIG. 5F) that play important role regulating neuronal growth, survival, which is dependent on TLR4 signaling (FIG. 5G). PKA/PKC was reported to impart TBI (Lucke-Wold, Logsdon et al. 2014; Zohar, Lavy et al. 2011; Titus 2013). Overall, despite delayed intervention (3 days) sPIF reversed advanced brain injury—reflecting strong applicability to emergency scenario where immediate advanced intervention is not available. For currently used neuroprotective drugs ability to reach the brain in both intact and damaged settings is difficult. Therefore frequently drugs in order to pass the BBB they have to be very small, or have to be added to agents that would favor passage.

Figure 6:
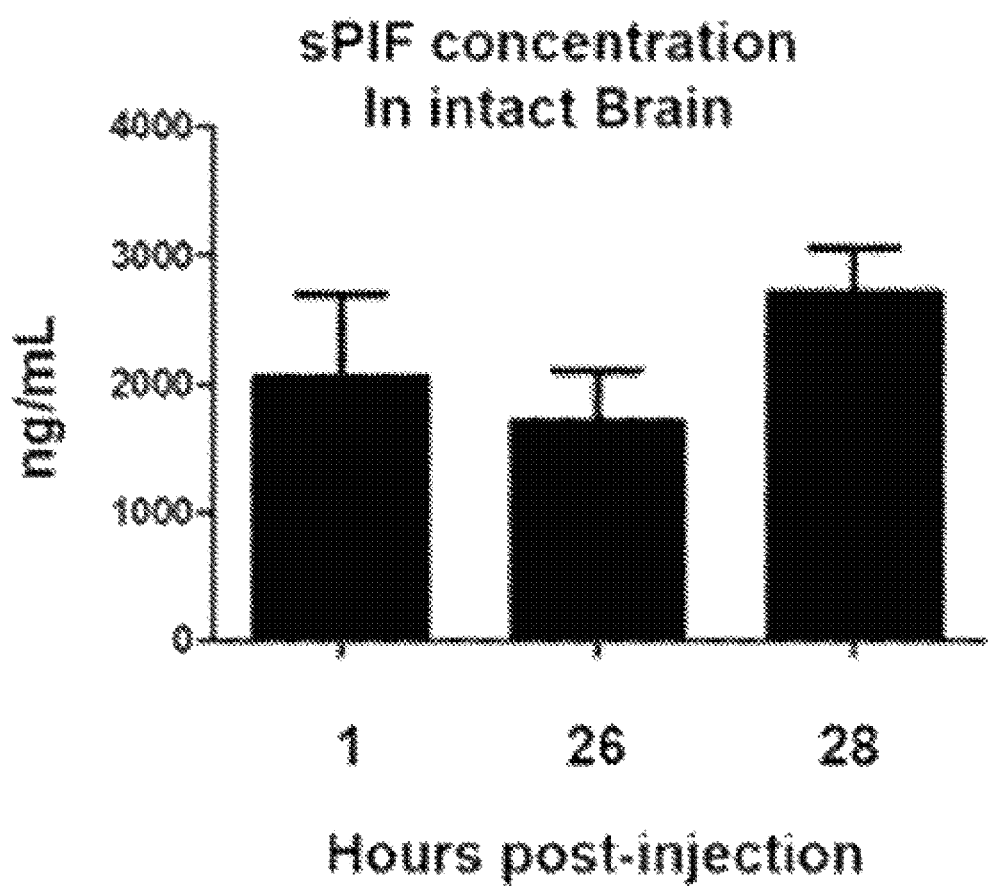
FIG. 6 depicts sPIF concentration in adult intact brains. Healthy adult CD-1 mice were injected with sPIF (0.75 mg/kg body weight) subcutaneously every 12 hours (n=3 each time point). sPIF was detected using liquid chromatography with tandem mass spectrometric detection. sPIF can be detected 1 hours after injection in brain tissue and the concentration does not change significantly after 26 (3 injections) and 28 hours (3 injections).
Figure 7:
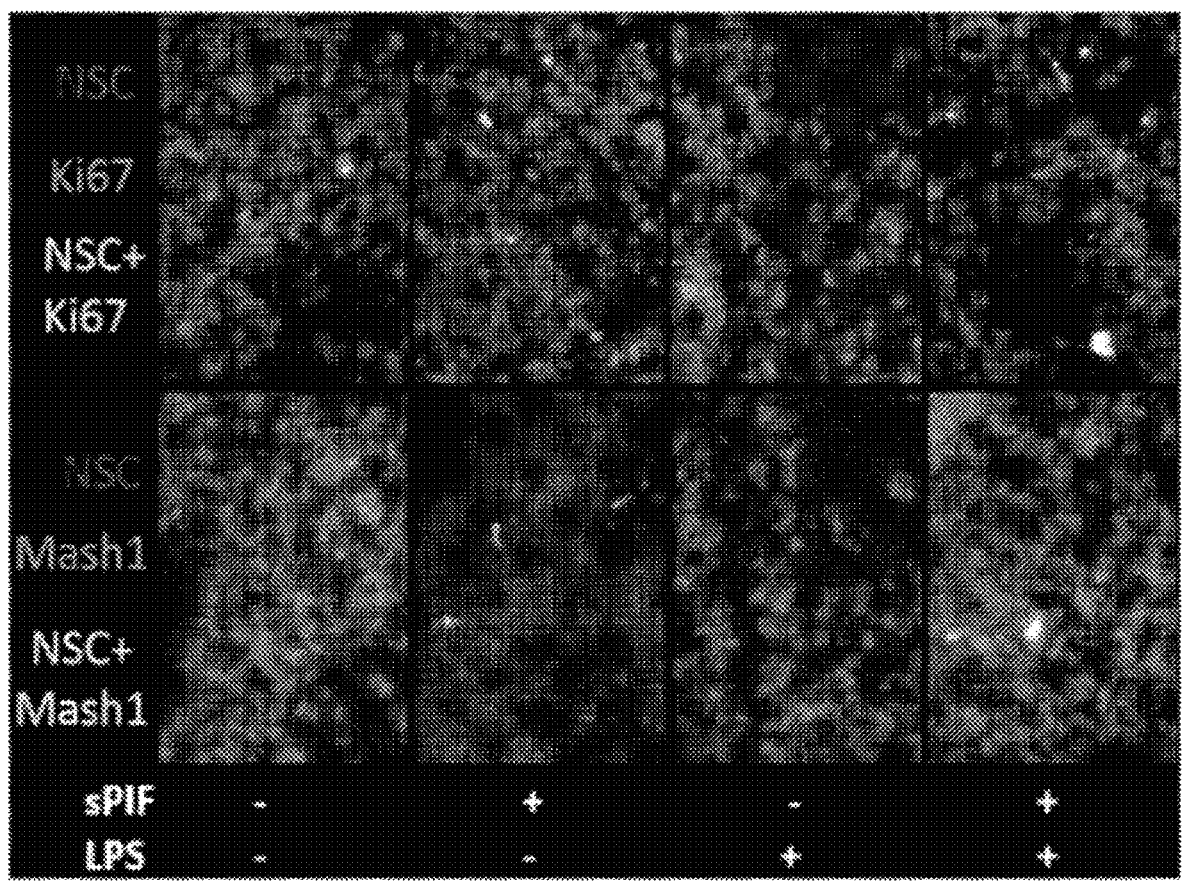
FIG. 7 depicts images of PIF effect on neural stem cell proliferation and differentiation. Animals were treated with LPS or NaCl on postnatal day 1. On the following day the sPIF treatment (0.75 mg/kg b.w. twice daily) was started for 5 days. LPS induces NPCs proliferation and differentiation (compared to healthy animals). sPIF induces increased NPCs proliferation and differentiation compared to NaCl or LPS treated animals. Brains were removed following mice sacrifice and placed in Mill machine observing brain architecture comparing LPS with PIF+LPS and sham control. Expression of H19 was also examined.
Figure 8:
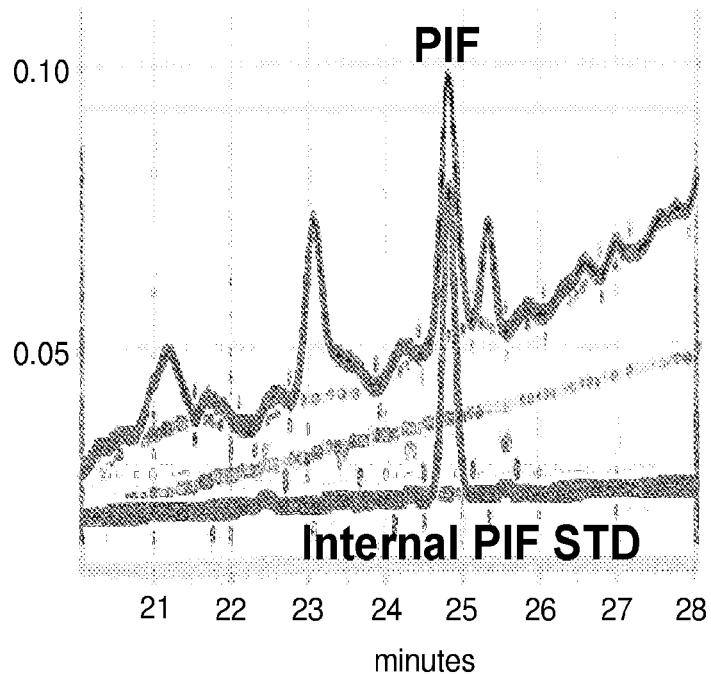
FIG. 8 shows the detection of PIF by mass spectrometry using an internal PIF-8 dalton larger standard. The clearance of PIF from mice circulation following high dose PIF administration is also shown.
Figure 8:
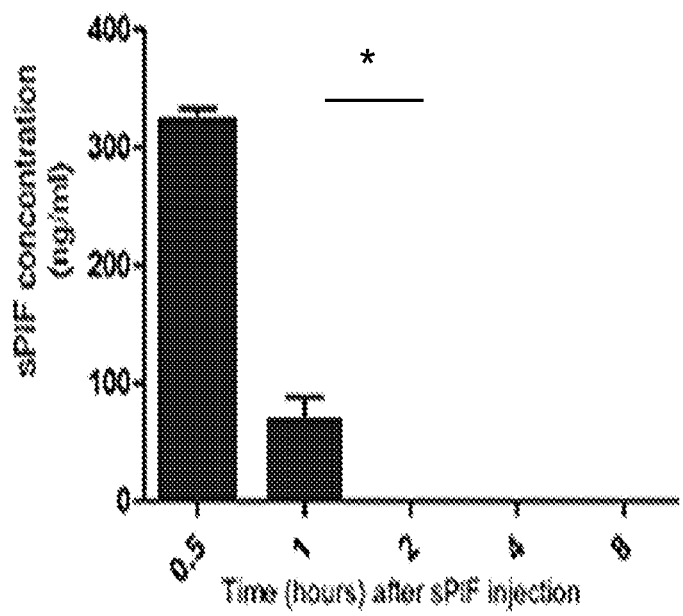

Highly critical for sPIF use for neurotrauma management is that it traverses BBB rapidly, intact that means it is NOT degraded. sPIF was injected into adult mice subcutaneously and at different time points brain tissue harvested was extracted using HPLC/mass-spectrometry using sPIF as internal standard. sPIF was found intact in the brain after 12-26 hrs after injection thus making the drug an attractive as a long-term neuroprotectant. (FIG. 6). Within 30 min reaches a peak after subcutaneous injection while at the same time point it also targets the systemic immunity. FIG. 7 shows the detection of PIF by mass spectrometry using an internal PIF-8 dalton larger standard. The clearance of PIF from mice circulation following high dose PIF administration is also shown. (HPLC/Masspectrometry method. FIG. 8 shows that while PIF reaches the brain detected by antiPIF monoclonal antibody documenting a target effect on both microglia and neurons at the same it has already been cleared from the circulation (FIG. 8). It further demonstrates that Rhodamine-PIF crosses the BBB to target the brain. Simultaneous local (brain) and systemic (immune) targeting reflect an integrated sPIF induced protection. This shows that sPIF can be easily and efficiently deployed and rapidly utilized post-acute neurotrauma.

sPIF Promotes Endogenous Stems Cells Proliferation/Differentiation: Chronic Neurotrauma Therapy.

Figure 9:
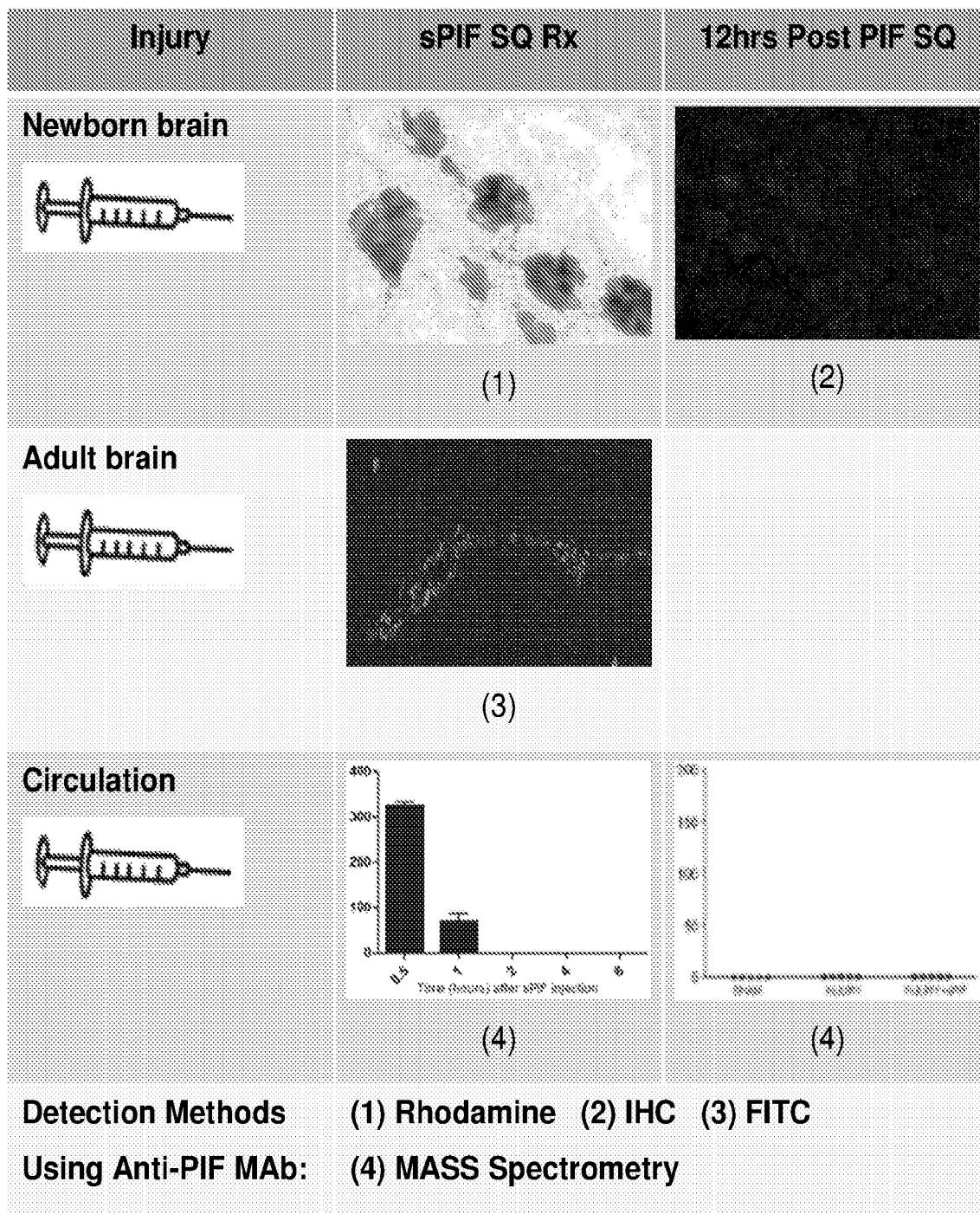
FIG. 9 depicts PIF penetrates the BBB in injured brain but absent in healthy circulation.

Neuronal loss frequently occurs post-CNS injury, due to the progressive uncontrolled inflammation. To restore neurotrauma disease, the challenge remains to repair or replace those cells and restore their communication with other cells to integrate function. sPIF has the potential to be effective in that respect. In the developing brain, radial glia act as neural stem cells (NSCs) and is located in the subventricular zone (SVZ). NSCs generate oligodendrocytes and restricted populations of neurons and importantly represent a large reservoir of cells for repair post-injury. However, NSCs progressively become quiescent post-natally. During self-renewal NSCs divide symmetrically into two NSCs or asymmetrically into one NSC and one transit amplifying cell (TAC). Electroporation in neonates is able to selectively target and manipulate radial glia-NSCs enabling accurate assessment of proliferative cells transfected (fluorescently labelled) NSCs examining their fate by TACs measurements (Mash1 positive cells). Activated dormant NSCs induce de novo gliogenesis and neurogenesis for endogenous repair following injury. (FIG. 8A) NSCs in the SVZ are resistant to hypoxia-ischemia while TACs, oligodendrocyte progenitors, and newborn neurons are vulnerable contributing to oligodendrocyte and neuron depletion. Thus, targeting NPCs and increasing TACs is an attractive repair strategy.

sPIF may activate NPCs via PI3/AKT-mTOR signaling. sPIF treatment (0.75 mg/kg twice daily s.c.) NPCs in healthy and LPS-pretreated animals (sham controlled design, n=8 each group) was examined. After 5 days brains were probed with Ki67 (proliferation marker) and Mash1 (TAC marker). Indeed sPIF treatment results in NSCs activation (both proliferation and differentiation into TACs) in healthy or LPS pretreated brains. (FIG. 9A) Collectively sPIF has strong potential to activate NSCs and may impart neuroregeneration post-TBI. The observations in this model were also translated to imaging using advanced MRI (FIG. 9B). Results showed that sPIF following exposure to LPS treatment has led to restored brain architecture as compared to (normal) LPS-treated animal. When the data on sPIF was compared to sham treated animal no significant differences were noted. This documents that sPIF induced protection is translated to significant brain repair. Mechanistically based on the data the effect may be due to the activation of the H19-related pathway.

sPIF Directly Targets Specific Proteins in the Brain. (HIE Model).

Figure 10:
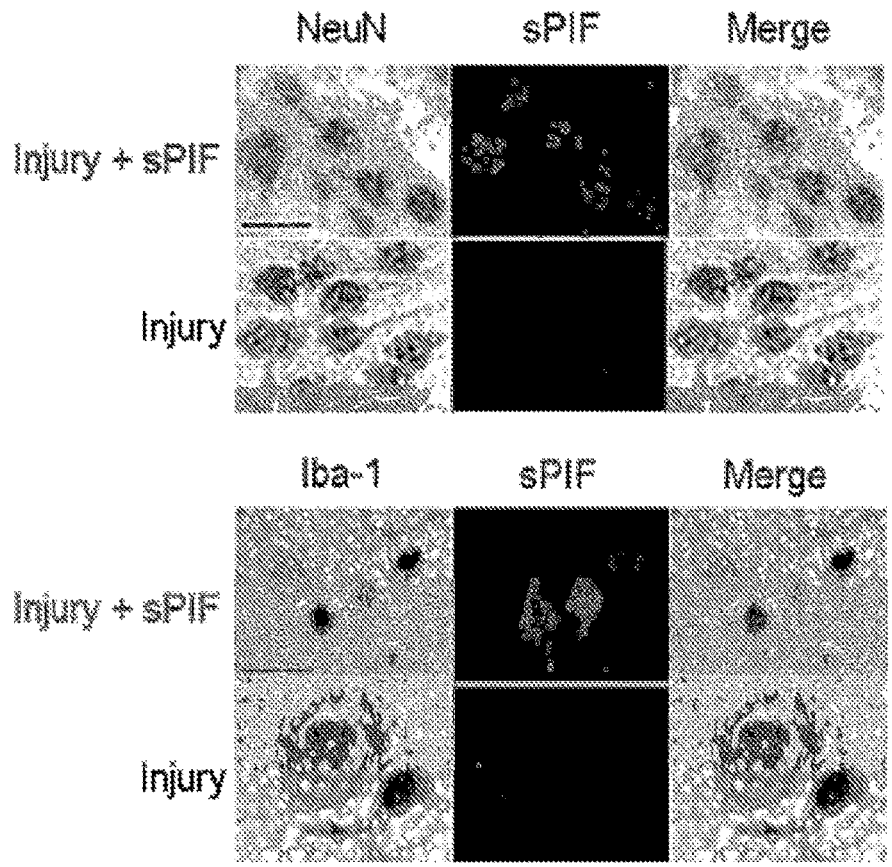
FIG. 10 depicts PIF presence in the brain targeting microglia and neurons as demonstrated by anti-PIF monoclonal antibody staining. Also injected Rhodamine-PIF crosses the BBB reaching the brain. In contrast, at the same time point 12 h post-injection in the HIE model PIF is not found in the serum.
Figure 10:
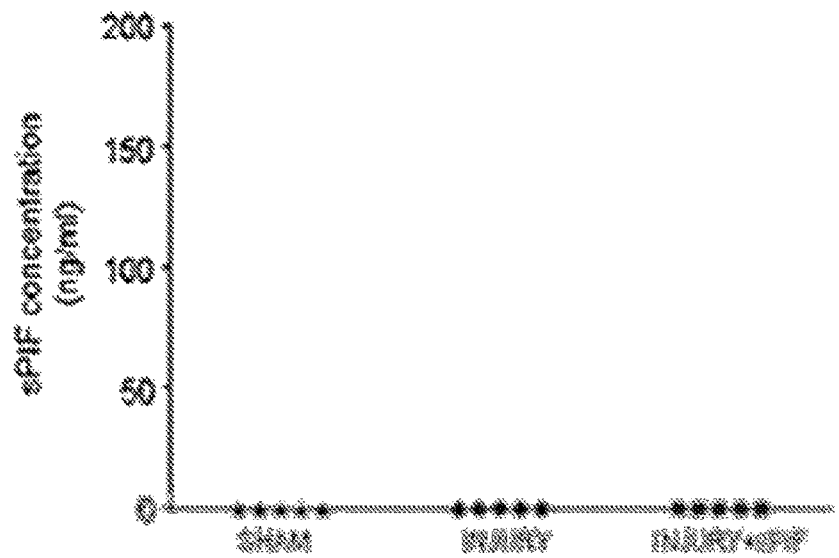
Figure 11:
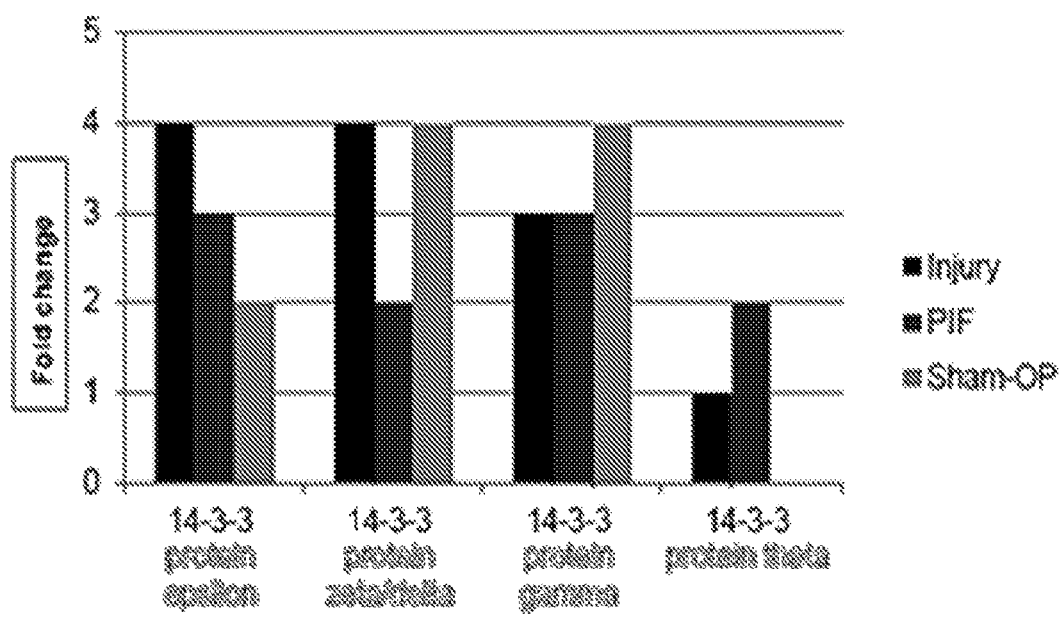
FIG. 11 depicts how PIF functions locally in the brain by regulating the phosphorylated 14-3-3. Identifies specific PIF binding targets in the brain and the effect of PIF on their regulation comparing injured vs intact hemisphere in the HIE model.
Figure 12:
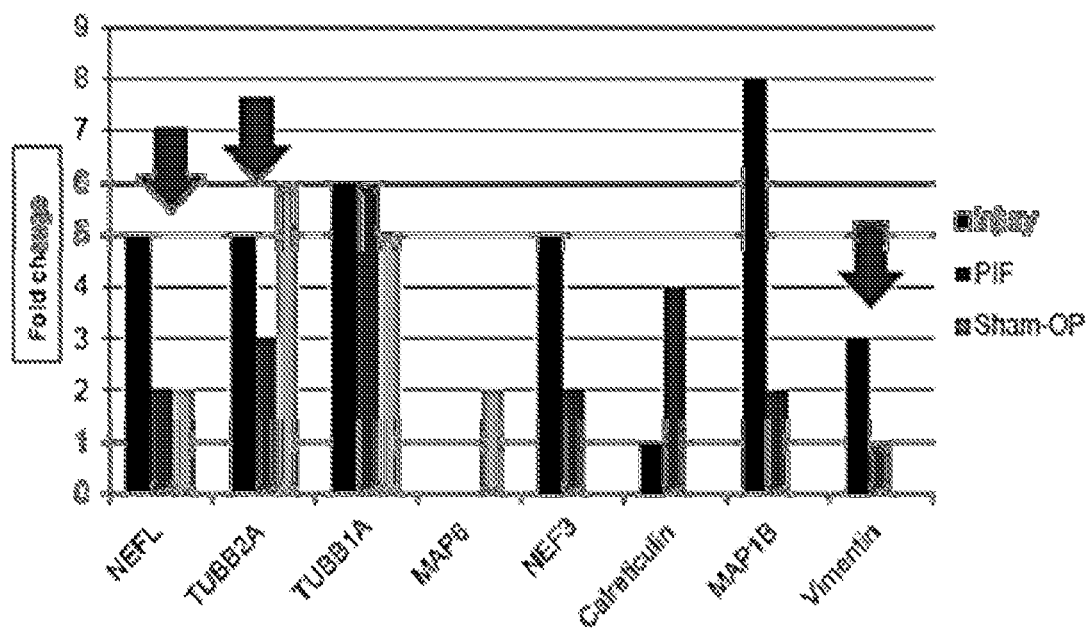
FIG. 12 depicts that PIF reverses TBI by regulating the PKA/PKC inflammatory pathways in the brain.

PIF modifies the brain protein ratio when comparing the intact to the injured part of the brain. Following harvesting, the brain was divided onto two hemispheres (injured and intact). PBS-treated and sham-operated rats were used as controls. The published method where sPIF was shown using an sPIF-affinity column which identifies specific targets binding to the peptide was utilized (Barnea 2014, PloS One). In this study, following extraction of the brain samples (treated and different controls) were passed through the PIF affinity column collecting different fractions. The fractions were passed through HPLC followed by mass spectrometry analysis. As figures show, sPIF has exerted its protective effects by affecting a specific limited number of signaling pathways. The main pathway is the 14-3-3 and PKC/PKA signaling. Pathways (FIGS. 10,11) The data generated provided important mechanistic insight into sPIF specific protein targets that affect the PKC/PKA pathway. Specifically sPIF reduced NEFL, NEF3, MAP1b, vimentin. In contrast, sPIF increased calreticulin concentration. The effect on this pathway leads to increase in brain maturation coupled with reduced neural death. In addition sPIF also affected the 14-3-3 pathway regulating several members of the group further reducing apoptosis. The change in the folding structure of a target protein may have a major contributing effect on sPIF activity. The inflammatory condition may affect the protein structure which could increase or decrease the ability for sPIF to bind to the target. Data substantiates the protective effect that sPIF exerts by directly targeting specific proteins.

sPIF Reverses HIE Induced Injury.

Figure 13:
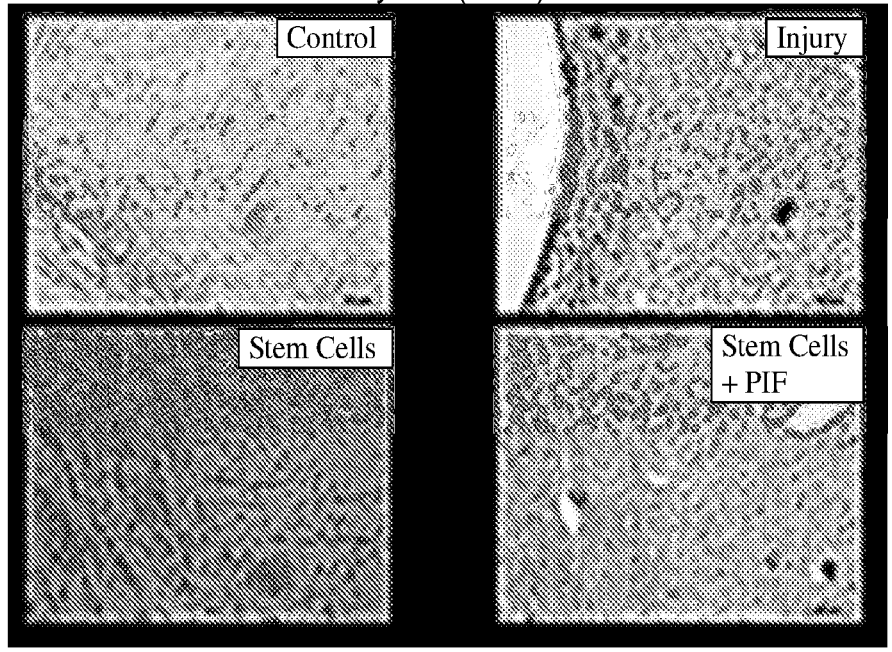
FIG. 13 depicts a comparison of treatment in rodents following brain injury where stem cells are provided as a control and stem cells with PIF as therapy. Brain cells were stained with myelin (HBP) and neuron markers (NeuN and Cux1) for viability and inflammatory elements.
Figure 13:
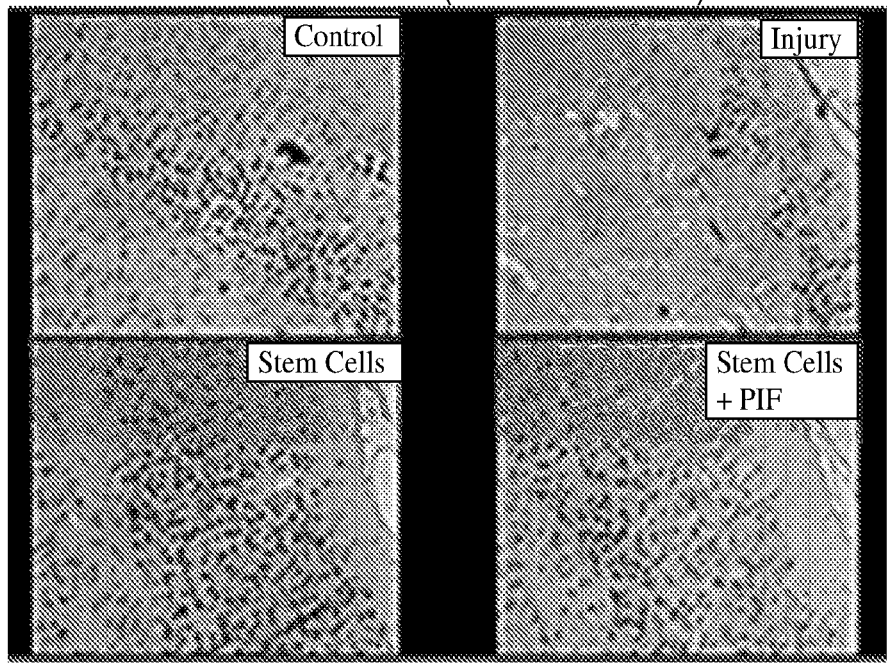
Figure 14:
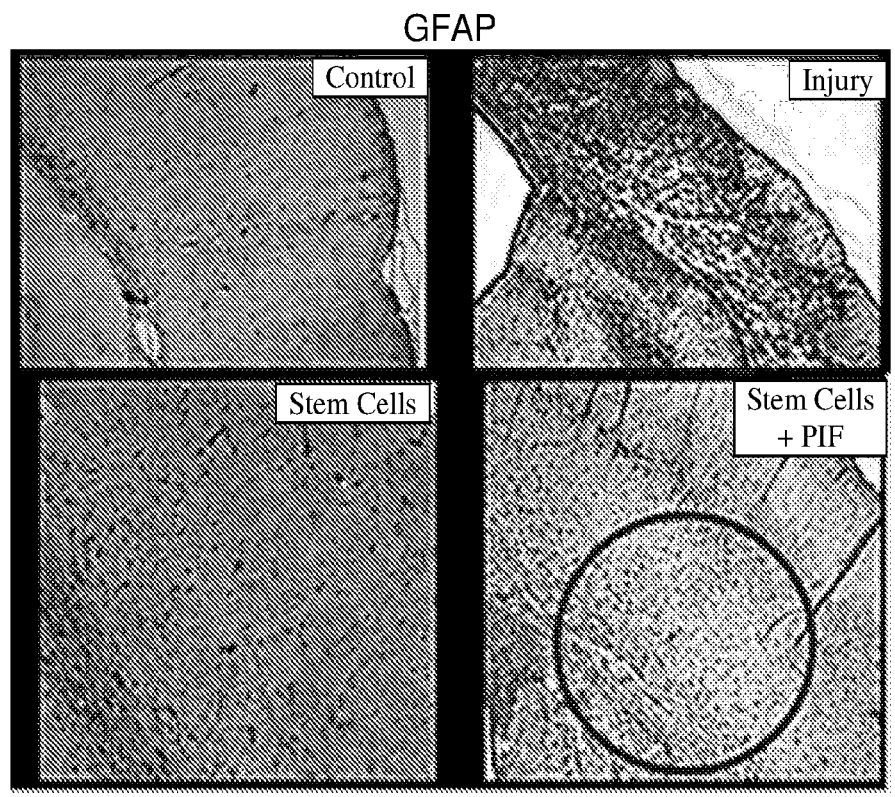
FIG. 14 depicts a comparison of treatment in rodents following brain injury where stem cells are provided as a control and stem cells with PIF as therapy. Brain cells were stained with glial fibrillary acidic protein (GFAP), a protein marker for nerve cells.

Subcutaneously injected sPIF is superior to intracranially injected stem cells—Chronic neurotrauma therapy. Stem cells use for treating neurotrauma has been advocated and has been used successfully in a limited number of well controlled clinical studies. To determine how sPIF is compared with stems cells, the HIE model was utilized. sPIF alone versus intracranially injected stem cells were compared. As shown, sPIF alone led to significant neural protection. sPIF was injected together with intracranially administered stem cells, starting therapy 3 days post-injury. Data showed that sPIF potentiated the stem cells effect as evidenced by increasing myelinization as well the Neun and Cux1 neuronal markers expression (IHC). (FIG. 13) In addition, by increasing the glial fibrillary acid protein sPIF promotes neuro-regeneration as compared to stems cells alone. (FIG. 14) Collectively, it indicated that a minimally invasive subcutaneous sPIF injection is more effective that the highly invasive stem cells injection. As such it makes sPIF an attractive drug for acute and chronic neurotrauma management since as shown above that the endogenous stems cells are being effectively activated by sPIF alone.

PIF Reduces/Regulates Inflammation to Promote Neural Repair—Chronic Neurotrauma—Therapy.

Figure 15:
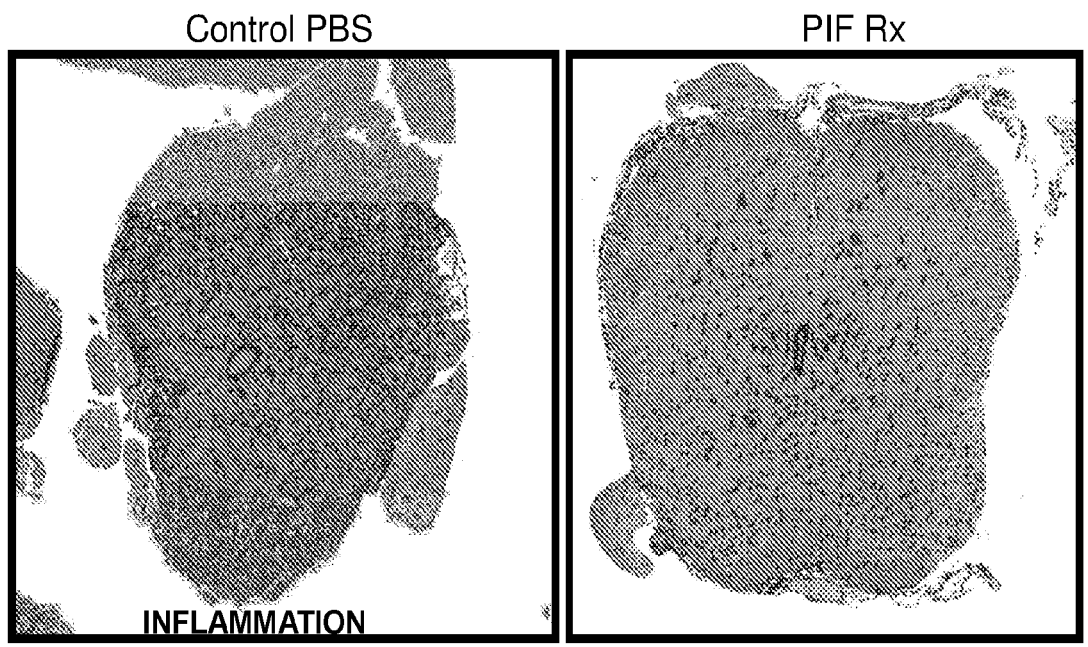
FIG. 15 depicts how PIF administration to animals prevents immune cell infiltration into the spinal cord in the EAE model (Weiss et al. 2012).
Figure 15:
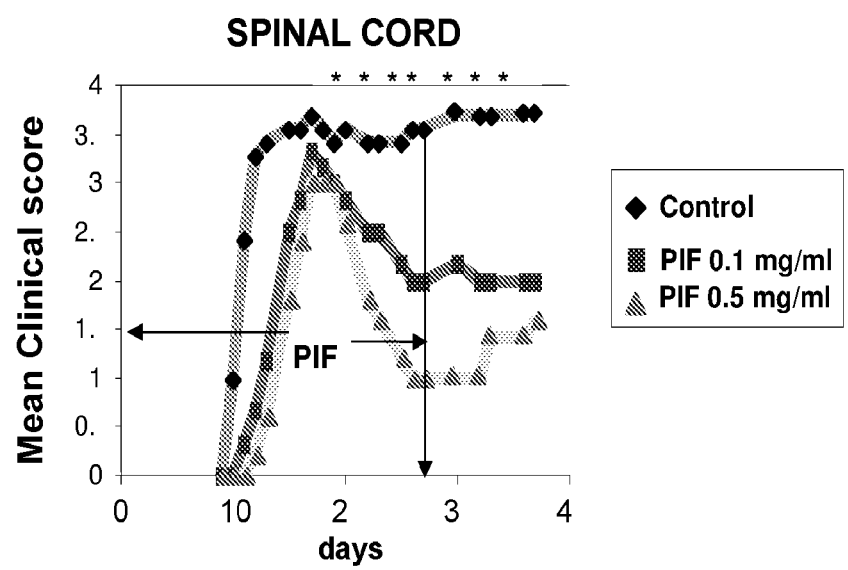

Based on current data post-acute neurotrauma if the subject survives is based on the extent of the trauma, it can remain conscious; can enter later in to a vegetative state, or vegetative state with minimal consciousness. Otherwise the long-term resulting motor, sensory and emotional state cannot be predicted in early stages of neurotrauma. Thus, a continuum occurs where it is not possible to predict prognosis whether partial or total recovery will ensue long-term following neurotrauma. Beyond the severe CNS (mentioned above) mild to moderate trauma can also have long-term sequela where the critical acute brain and spinal cord inflammation becomes progressive leading to and being associated with neurodegeneration. There is evidence that the resulting systemic inflammation causes or at least further compounds the destructive CNS process. The inflammatory cells activated perpetuate the damage by penetrating the CNS. Current measures to reverse this relentless course are widely ineffective beyond physical therapy and neuroleptic drugs as needed. The neuroinflammatory clinically relevant models used in the adult both antigen driven and infective which document for first time efficacy in this type of model aimed to address the chronic consequences of CNS related disorders. (Weiss et al. 2012, Shainer et al. 2015, Paidas, et al. 2012). PIF reverses chronic paralysis, including severe paralysis, and protects both brain and spinal cord-chronic neurotrauma management. This set of studies aimed to address early, mid and chronic phases of inflammation/ neurodegeneration seen frequently post-acute neurotrauma initiating shortly after and lasting long-term. The combination of PLP-neurotropic antigen, with pertussis, and tuberculin innoculum creates a particularly harsh neuroinflammation milieu evidenced both in the brain and the spinal cord. Unless treated, if inflammation is severe high mortality ensues. FIG. 15 shows that sPIF reduces access of inflammatory cells to the spinal cord and reduces the clinical score in a dose-dependent manner. The effect persists up to 12 days post-therapy without added therapy. Mechanistically, sPIF protected against proteins involved in oxidative phosphorylation thereby reducing oxidative stress and protein misfolding—similar to the HIE model. Increased MTAP protein promotes free tubulins-neuron backbone assembly to neurons. Increase in proteins involved in neural synaptic transmission was noted as well. PIF reduced circulating pro-inflammatory IL12—a macrophage marker and PLP activated-splenocytes (IL6, IL17) secretion also at 2 weeks post-therapy. Thus sPIF represents effective treatment regimen to reverse chronic consequences of CNS injury, including paralysis, where inflammation plays a critical role. Further data showing both local and systemic effects demonstrate a global (comprehensive) protective action.

sPIF Prevents and Reduces Mortality Long-Term.

Figure 16:
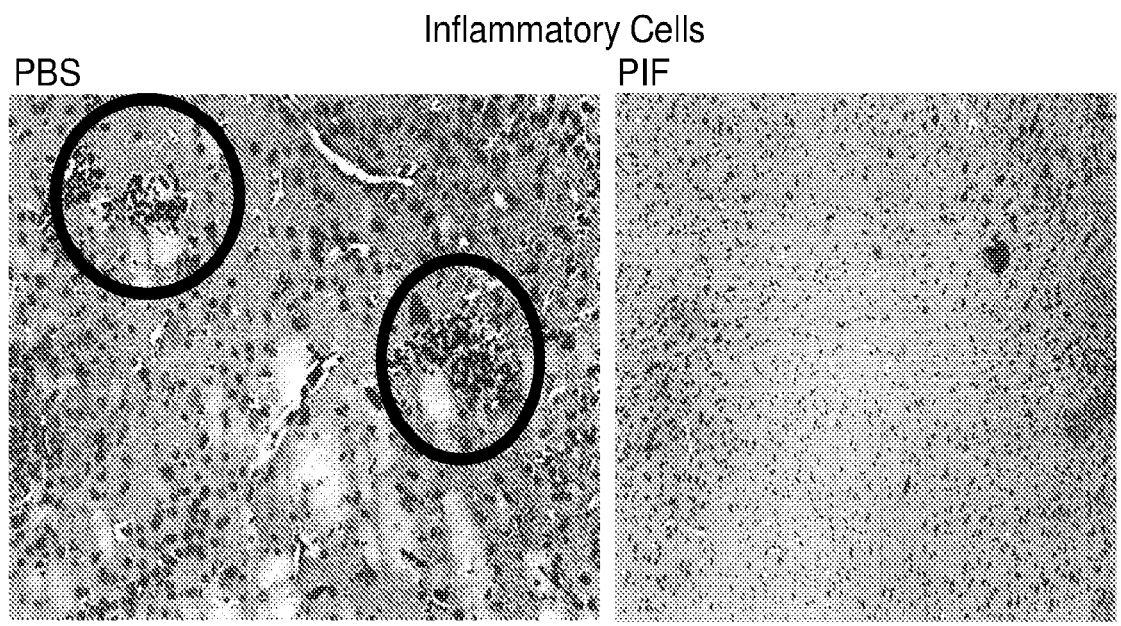
FIG. 16 depicts how PIF was successful in reversing brain infection by reducing inflammatory cells access to the brain.
Figure 16:
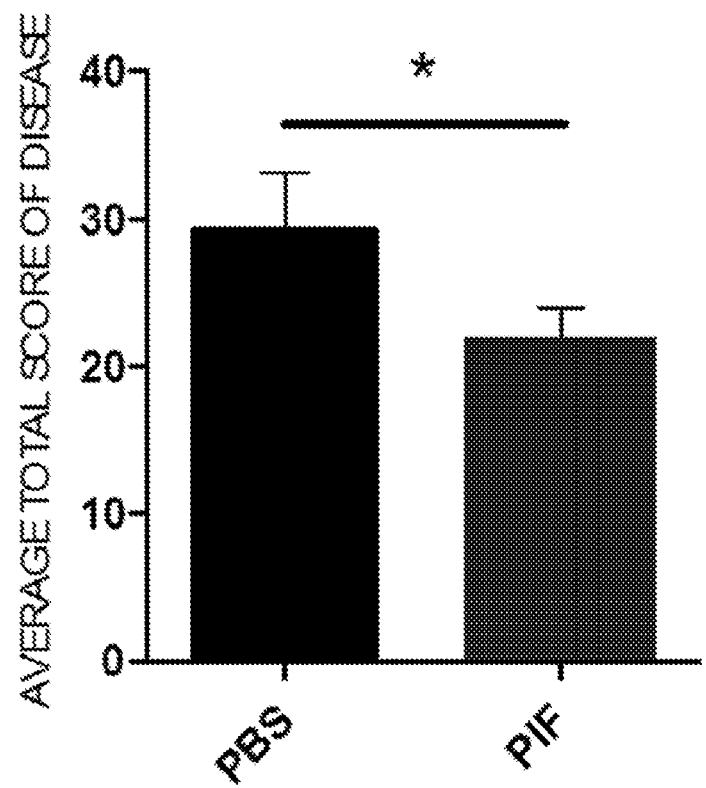
Figure 17:
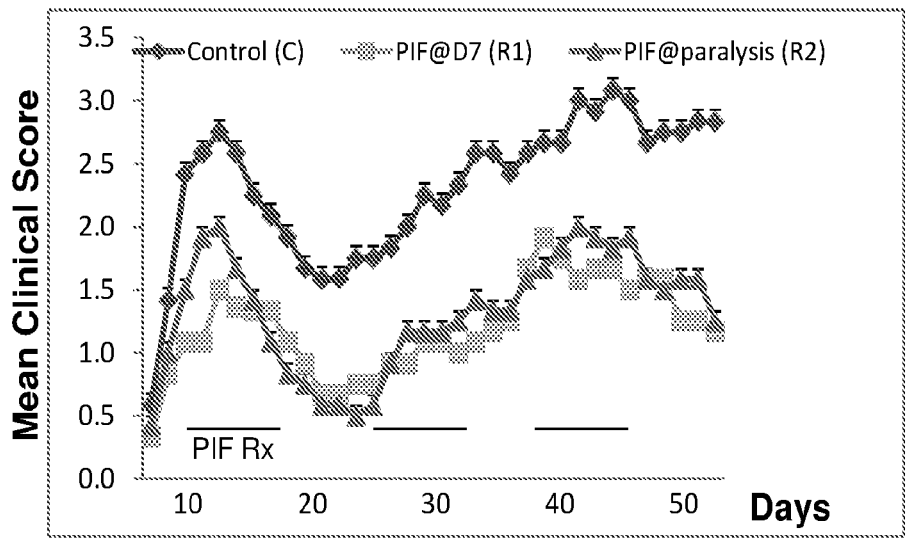
FIG. 17 depicts how PIF can reverse chronic paralysis over time in comparison to subcutaneous injection of Copaxone® effect on the clinical score.
Figure 17:
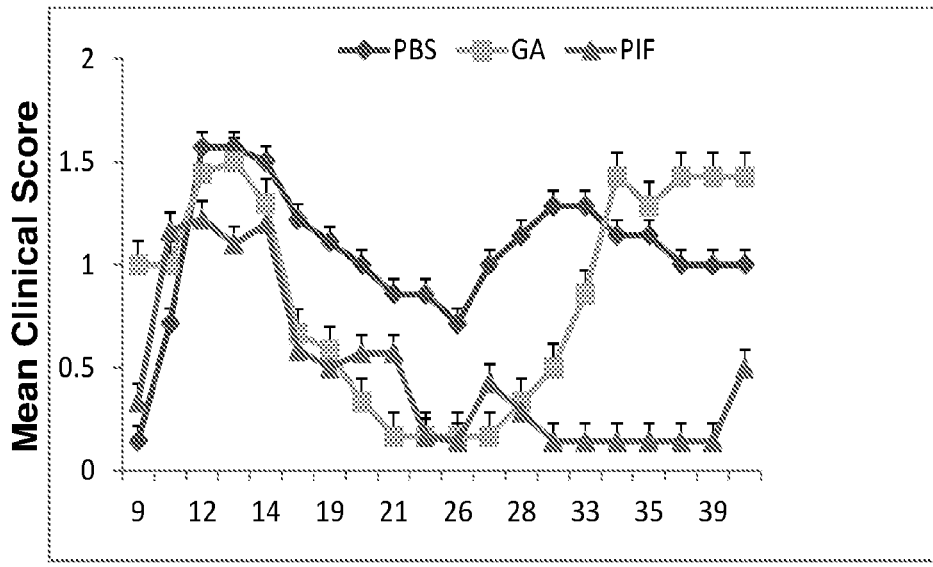

Episodic (short-term sPIF subcutaneous injections) completely reversed paralysis remarkably from paraplegia (stage 4/5) in 68% of cases vs. Copaxone (GA) and PBS used as controls (12.5%), P<0.007. (FIG. 16). An integrated local (brain and spinal cord) decrease in inflammation and inflammatory cells access was also noted. The brain was analyzed using global phosphorylated proteins analysis comparing sPIF to PBS treatment as well non-treated controls. In addition PIF also reduced the access of inflammatory cells into the brain (FIG. 17)

sPIF Reverses Paralysis and Reduces Brain Inflammation Post-Infection: Chronic CNS Neuro Injury Management.

Figure 18:
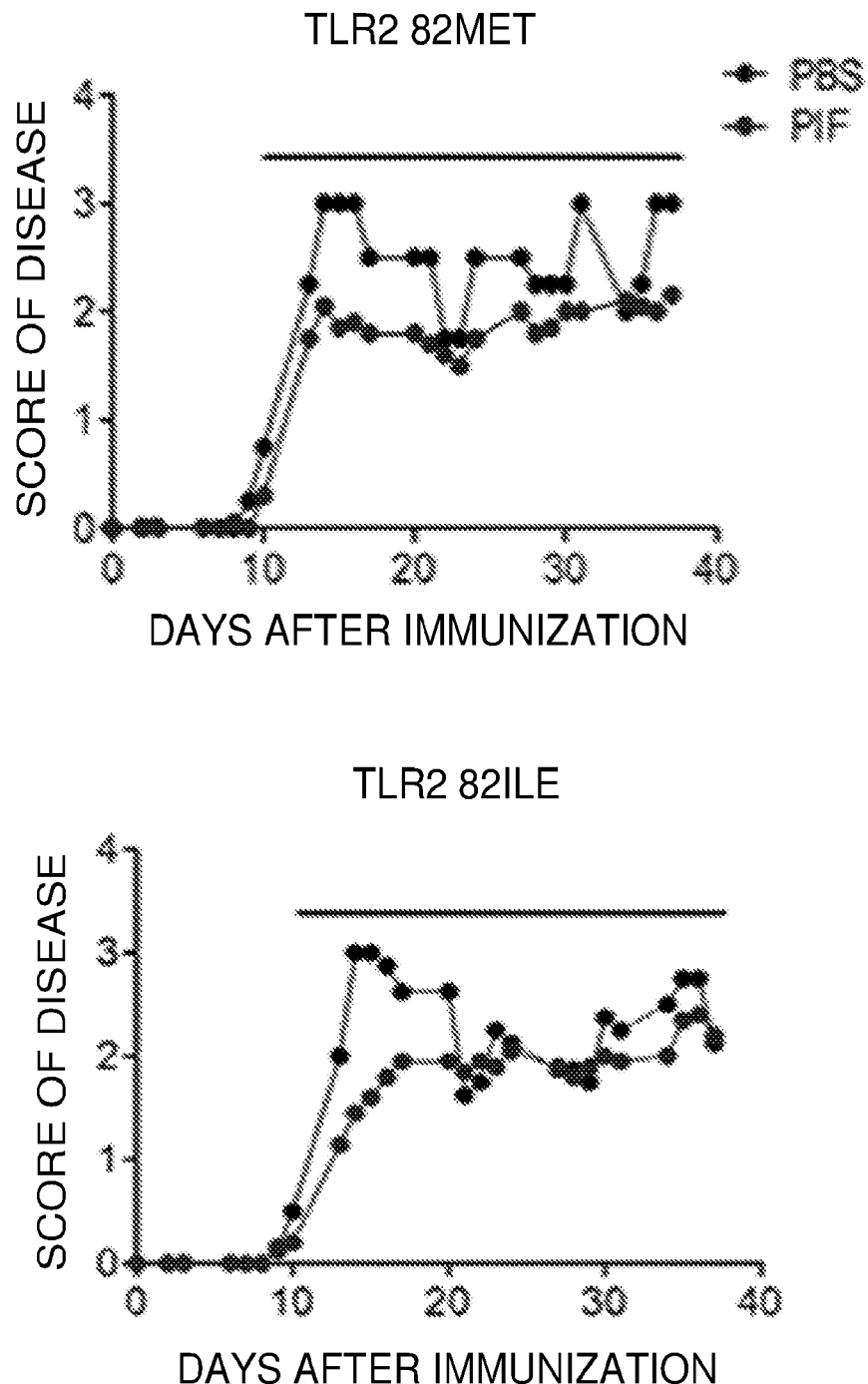
FIG. 18 depicts how two different mouse strains with a mutated TLR2 gene known to develop paralysis have reduced disease score when treated with PIF.
Figure 19:
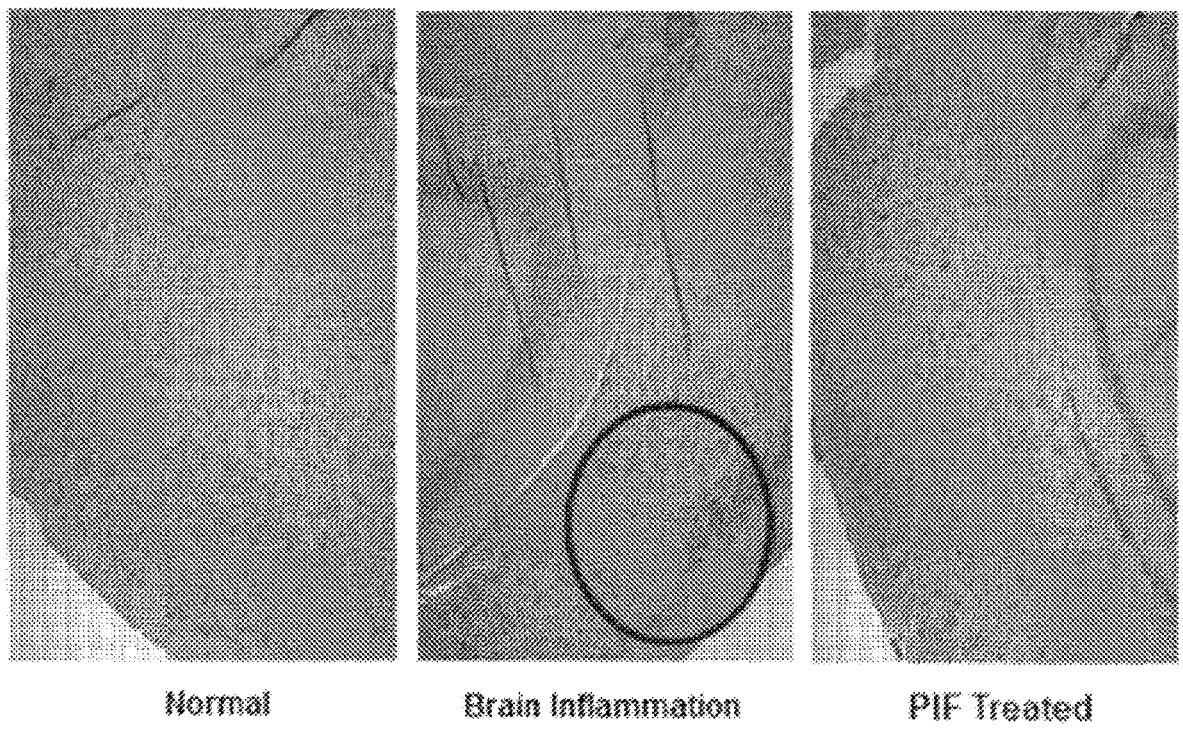
FIG. 19 depicts how in an infectious—Smegamtis EAE model—PIF administration to animals reverses chronic brain inflammation and protects the cortex.
Figure 20:
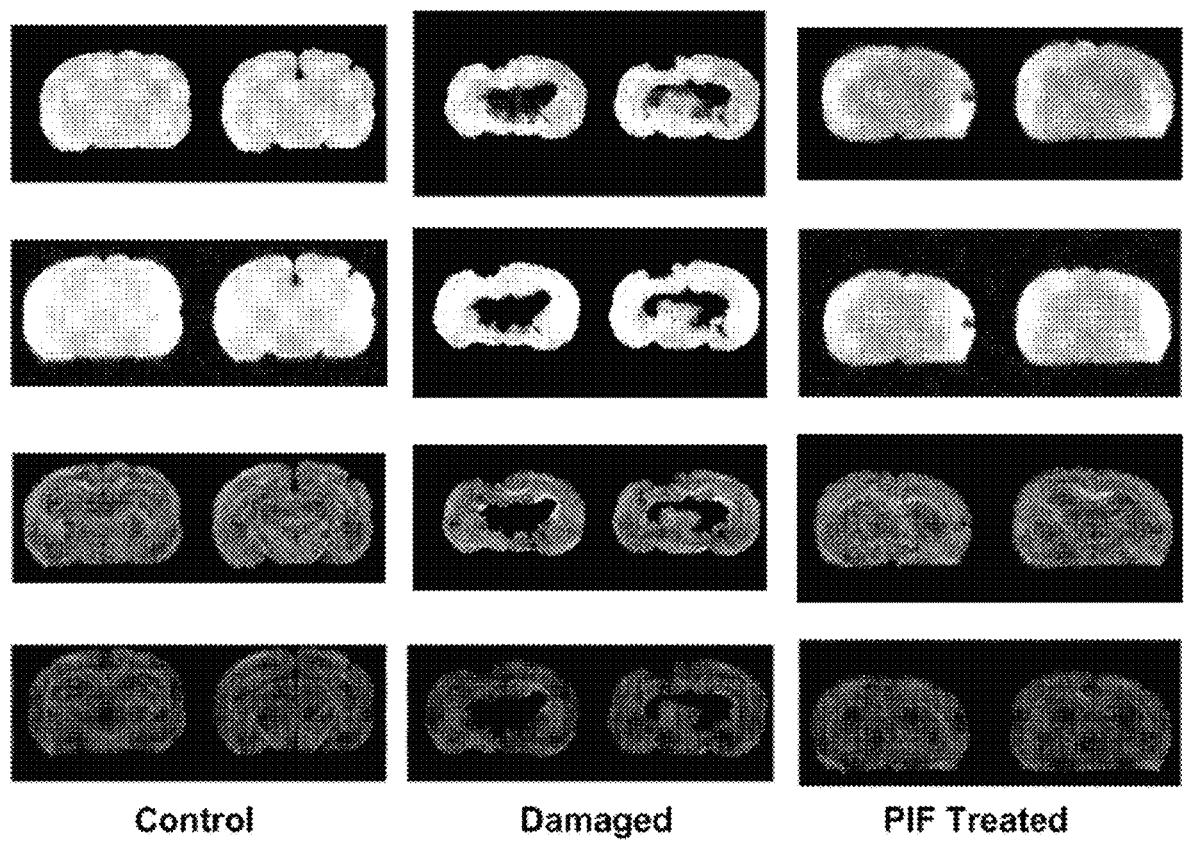
FIG. 20 depicts FITC-PIF directly targets the brain and the spinal cord.
Figure 21:
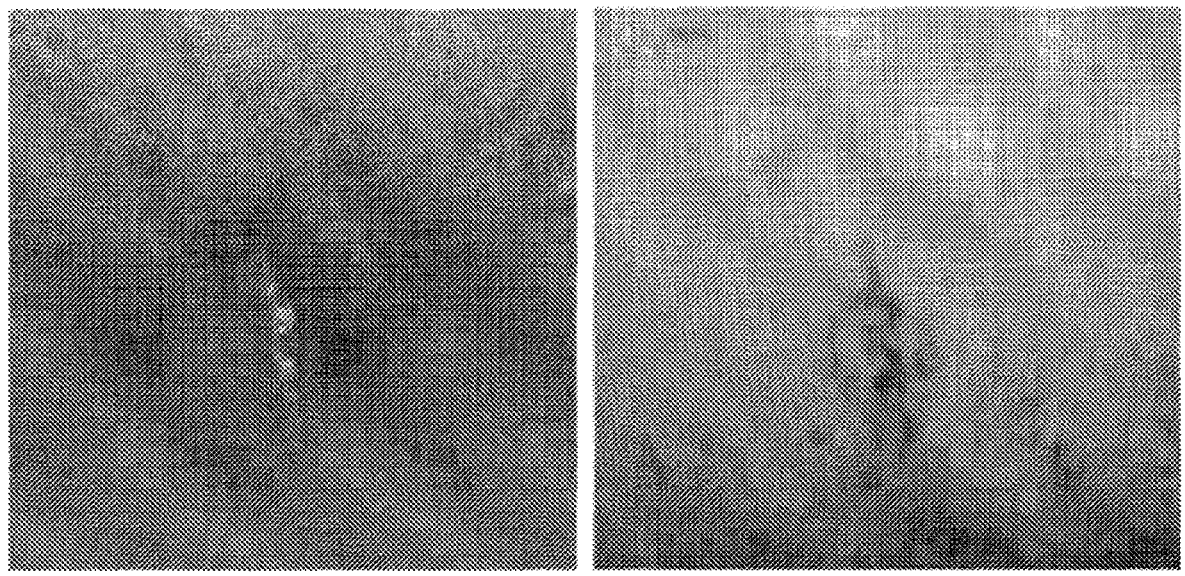
FIG. 21 depicts how PIF targets both the brain and the spinal cord in a *smegmatis* bacteria model.

Based on current evidence, environmental factors (bacteria, virus) may cause progressive neurodegenerative diseases in the CNS. The *Smegmatis* bacteria model in an important prototype where an innocuous bacterium activates the immune system and then the bacteria is subsequently eliminated while neurodegeneration continues to progress long-term. This clinically-relevant model could replicate also a neurodegenerative chronic neurotrauma including and multiple sclerosis—(MS) shown by (Nicollo, Ria J of immunology 2102). sPIF reversed brain infection, inflammation and paralysis post-inoculation with *Mycobacterium Smegmatis* (MPT64-PLP139-151). Brain IHC analysis showed that sPIF reduced the access of inflammatory cells into the brain. (FIGS. 18-19) Beyond the long-term reduction in paralysis observed, global brain gene analysis demonstrated reduced oxidative stress as well as up-regulated additional protective pathways. Systemically, PIF down-regulates the pro-inflammatory IL23 and IL17 expression in draining lymph nodes. Thus PIF has both a local (brain and spinal cord) and systemic neuroprotective effect.

Whether sPIF penetrates the brain (BBB) following chronic inflammation was furthermore studied. FITC-sPIF was injected IP and subsequently the brain was imaged. Imaging demonstrated that sPIF enters the brain, and very importantly it targets the CNS vasculature. This is highly relevant since sPIF was shown to prevent vascular inflammation. Thus, in addition to targeting the microglia and neurons, sPIF also protects against the ensuing vascular inflammation—offering an integrated protection against chronic neurotrauma.

sPIF Reverses Chronic Neuroinflammation in TLR-2 Mutated Mice—Chronic Neurotrauma Therapy.

Figure 22:
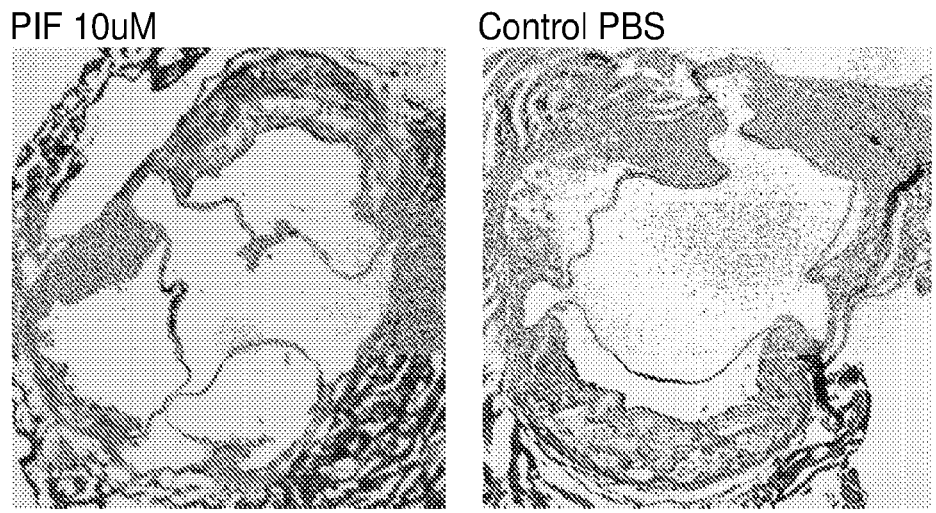
FIG. 22 depicts how PIF protects against vascular damage in a murine model for vascular disease. The data demonstrate that PIF is successful in reducing the volume of plaques in aortic roots of animals with a high fat diet.
Figure 22:
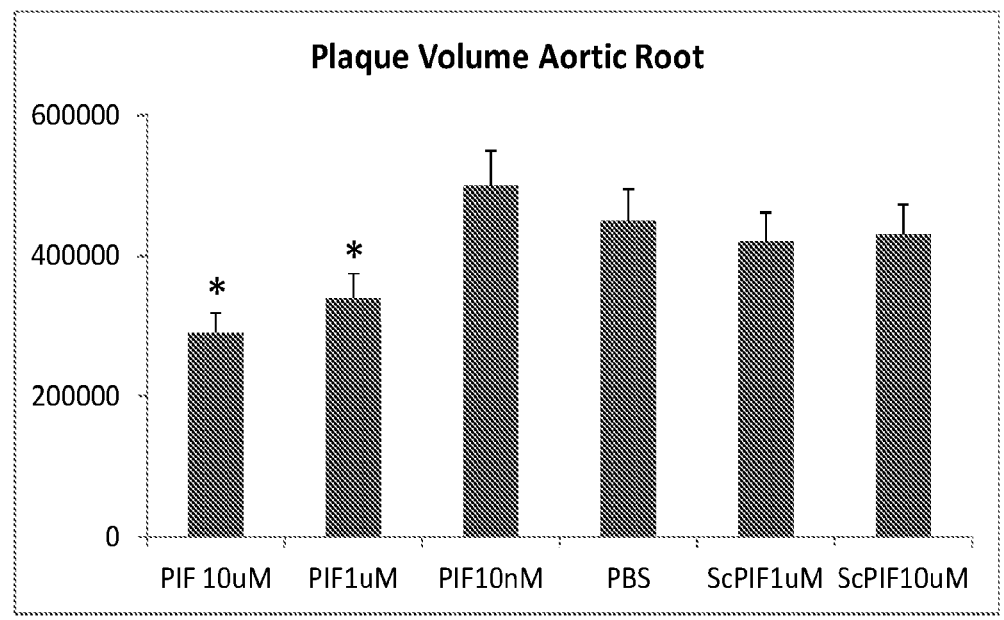
Figure 24:
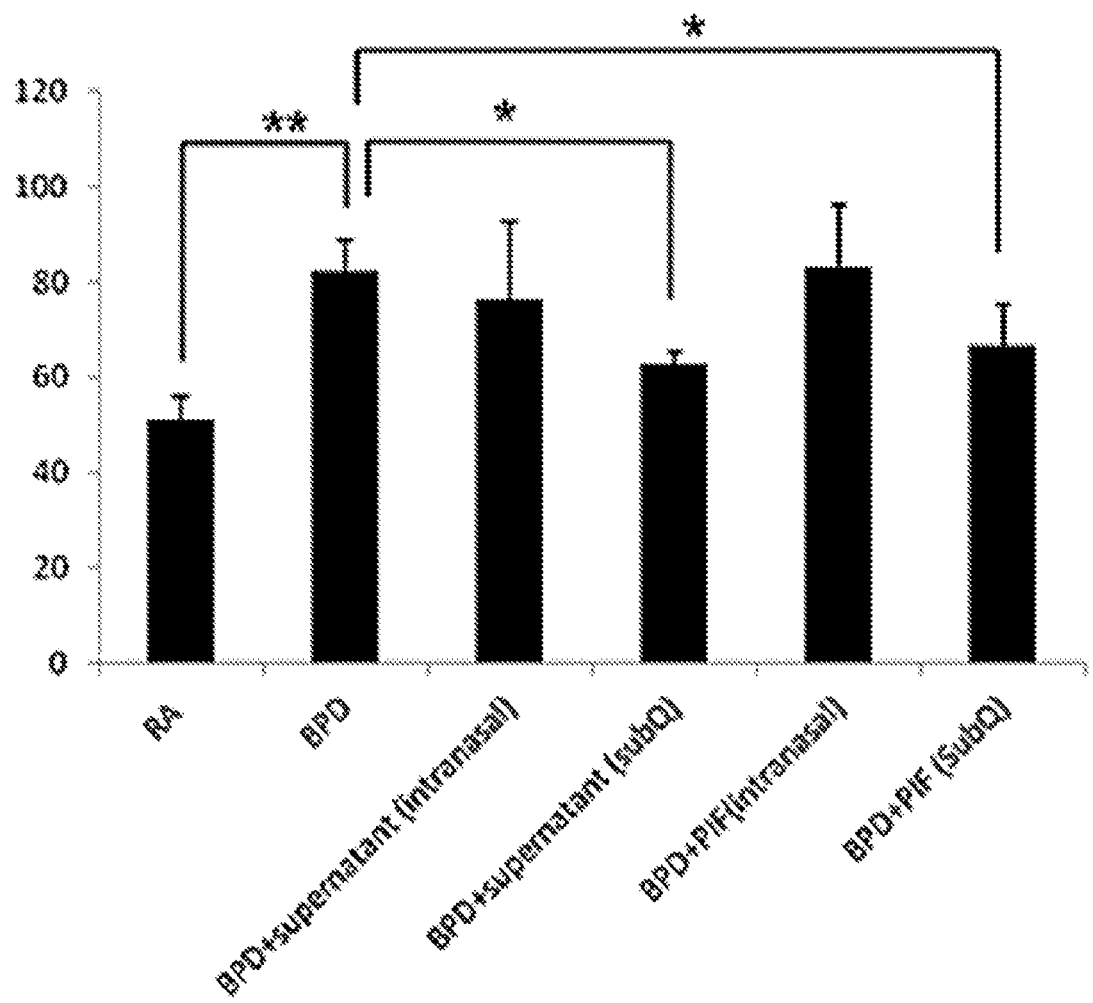
FIG. 24 depicts that chord length is a morphometric estimate of alveolar size (shorter is better) known to be increased in BPD.

Based on current evidence, modification of the TLR locus in mice followed by injection of PLP 139-151 in the SJL/B6 wt model leads to severe paralysis. Initiation of subcutaneous sPIF treated after 10 day post-induction has led to a therapeutic effect as shown by the decrease in the score of the disease (decrease of paralysis score). Irrespective of the two different TLR-2 mutations, sPIF decreased the clinical score. (FIG. 22). This data further substantiates that sPIF is an effective agent that could reverse chronic neuroinflammation irrespective of the underlying cause, inflammation., infection or pro-inflammatory cytokine mutation.

sPIF Reduces Bronchopulmonary Dysplasia Following Hyper-Oxygenation.

sPIF Reduces acute neurotrauma associated therapy side effects. Post-neurotrauma frequently there is a phase of significant apnea requiring exposure to high oxygen concentration. This standard of care aims to increase the oxygenated blood flow to the injured tissues assisting in the healing process. Due to the severity of the injury, the exposure to such high and prolonged levels of oxygen can lead to long-term damage including bronchopulmonary dysplasia (BPD).

sPIF's protective effect against BPD development was compared to conditioned media derived from MSC isolated from Wharton's Jelly (WJMSC). WJMSC were grown in DMEM+10% FBS until 70% confluency then washed and grown in DMEM without FBS for 24 hrs, and supernatant was concentrated. Newborn WT mice were exposed to hyperoxia from post-natal day 1-4 (saccular stage of murine lung development) and allowed to recover in room air for 10 days. Mice were sacrificed on post-natal day 14. Newborn mice were injected subcutaneously or intranasally daily with the supernatant (10 ul/day), or sPIF (1 mg/k/d) for 4 consecutive days during hyperoxia. Alveolar size was estimated from the mean+/−SD chord length of the airspace (N=4 for each group) analyzed Student two-tailed unpaired t-test, P<0.05 considered statistically significant. Chord length is a morphometric estimate of alveolar size (shorter is better) known to be increased in BPD. Average cord length was 50.97 μm in control animals and 82.54 μm in BPD animals. Subcutaneous injection of sPIF and conditioned media significantly reduced alveolar space as demonstrated by shorter cord length of 66.81 μm (sPIF) and 62.80 μm (conditioned media; p<0.05) and improved alveolar architecture (FIG. 24). Intranasal injection of sPIF and conditioned media showed no benefit. sPIF and conditioned media from WJMSC delivered subcutaneously are effective in treating alveolar damage secondary to BPD. Data shows that sPIF presents a beneficial effect in addition to neurodamage protection reducing the possible lung injury that is associated with hyper-oxygenation. Such beneficial effect provides further evidence that sPIF could be an effective drug for neurotrauma and/or BPD.

Summary

As recent data emerged that the central and leading consequence of neurotrauma is the progressive and not fully timed, predictable and or quantifiable inflammatory response to injury. This response is recognized as being both local (brain and spinal cord) and systemic (lymph nodes and circulatory elements). Even a mild trauma can lead to long-term impairment. Due to PIF's endogenous (embryonic origin) and inherent regulatory function, in particular its comprehensive neuroprotective properties and effect on systemic circulation, it could be an effective drug to treat both local and systemic neurotrauma manifestations.

This stems from the following observations and support data generated.

First, PIF's protective effect on the embryo translates to adult clinically relevant preclinical models. The observed protective effect is due to sPIF targeting proteins which reduce oxidative stress and associated protein misfolding. Such pathways are critical for protecting against neurotrauma. Inflammation is the primary response of the CNS/neurotrauma and current therapy following injury results in progressive neurodegeneration in the long-term. Paradoxically, the aim to self-repair actually perpetuates the ensuing inflammation. Second, in acute and chronic settings, sPIF is effective in reversing brain injury, brain inflammation and spinal cord inflammation. Thus long-term effect of sPIF in the treatment of neurotrauma is evidenced by the reduced mortality and resolution of high grade paralysis.

The ability of sPIF to exert these beneficial effects stems from the fact that PIF has a unique integrated mechanistic effect targeting specific proteins in the brain (FIGS. 6-10). The ratio of proteins from the intact to injured site is clearly evident. These proteins are involved in protecting against oxidative stress and neurodegeneration. In order for sPIF to exert such an effect first it has to be able to penetrate the BBB both in the injured and healthy brain. As demonstrated following PIF administration, it was found within the brain in an intact form—not degraded (sequence documented). In the brain in order to exert the reparative effect.

sPIF targets microglia to reduce inflammation as well neural cells to promote neuroprotection. This neuroprotection is due to activation the endogenous stems cells to proliferate and differentiate. Further PIF also protects against the neurodegenerative effect of LPS by imparting neuroprotection thereby almost doubling the brain size as compared to controls. PIF targets the vascular system within the brain. Such a direct effect on the vascular system was demonstrated to protect against inflammation reducing platelet and macrophage attachment as shown in the APoE-E model of atherosclerosis. Thus through local action in the brain and spinal cord following injury, sPIF has a direct effect on inflammatory elements, nerve cells, and vascularity. As such sPIF offers an integrated effect on CNS damage.

Systemic immune response is usually a delayed reaction to the CNS/neurotrauma) injury. PIF prevents the access of inflammatory cells both to the brain and the spinal cord. Thereby CNS inflammation is not further amplified which would perpetuate damage. Systemic reduction in response to CNS damage is evidenced both at the cellular level where sPIF reduces draining lymph nodes prime pro-inflammatory IL-17 and IL-23 cytokines. This reduction is coupled by the decrease noted in circulating and spleen-secreted splenocytes as well pro-inflammatory cytokine secretion. Such cell and circulating elements together with reduced access to the brain and spinal cord constitute an integral systemic protection against neurotrauma.

Each of the experiments above will be performed with varied concentrations of PIF analogs disclosed herein. If the results are similar to those results obtained by using wild-type PIF, we can conclude that PIF analogs behave in a similar fashion to wild-type PIF (SEQ ID NO: 11).

Example 3: sPIF Treatment in Graft Versus Host Disease (GvHD) (Prophetic)

Peptide synthesis; Synthetic PIF (SEQ ID NOS: 1-10) will be obtained by solid-phase peptide synthesis employing Fmoc (9-fluorenylmethoxycarbonyl) chemistry. Final purification will be carried out by reverse-phase HPLC and identity is verified by MALDI-TOF mass spectrometry and amino acid analysis and purified to >95%, by HPLC, and documented by mass spectrometry.

Mice: C57BL/6(H-2b) male and female and (C57BL/6× BALB/c) F1 male, five- to six-week-old mice (GVHD studies) and seven- to eight-week old SJL mice (MS studies) will be purchased, and male and female seven- to eight-week-old NOD mice will be obtained.

GvHD model: Recipients (C57BL/6×BALB/c) F1 mice will receive lethal whole-body irradiation by a single dose of 1000 rad/dose and will be reconstituted with $5-8\times10^6$ C57BL/6 bone marrow (BM) cells and $10-20\times10^6$ spleen cells. BM from C57BL/6 donor mice will be collected by flushing of femur, humerus and tibia into 10% FCS/PBS. BM mononuclear cells will be isolated from the interface after centrifugation on a Ficoll-Hipaque gradient. Spleens will be crushed through 70 μm screens into 10% FCS/PBS. BM cells plus spleen cells will be inoculated intravenously into whole-body irradiated mice one-day post radiation. PIF-1 therapy (0.1-1 mg/kg/day) will be administered in three separate animal trials 5-10/group vs. control by implanting under anesthesia an Alzet® pump in the dorsal subcutaneous region at the day of transplant for one to two weeks providing continuous release of PIF-1. Evaluation of GvHD model animals will be carried out by examining body weight, skin lesions, animal survival, and histological examination. Animal weight will be examined every three days following BM transplantation, scoring for skin manifestations of GVHD will be carried out from day 12 post BMT up to four months. Skin and liver samples will be fixed in 10% formalin embedded in paraffin and stained with hematoxylin and eosin and evaluated for ulcers, in the former and lymphocyte infiltration in the latter. Results will be evaluated by $X^2$ and ANOVA.

Assay for chimerism: Mice will be anesthetized and blood taken from the retro-orbital sinus of she eye. WBC (2-8× $10^5$/sample) will be separated, directly stained with anti-H-2K.sup.b-FITC ($IgG_{2a}$) or anti-H-2K.$_d$-FITC ($IgG2_a$) monoclonal antibodies (mAb) (Serotec, USA), and analyzed by FACS analysis (FACStar plus, Becton Dickinson, San Jose, Calif., USA). Background binding of each H-2K-specific mAb will be determined by staining with it the cells of non-relevant haplotype.

GVHD Model experiment I. Following low-burden BMT, GVHD development, mice will be examined following PIF-analog therapy (0.1-1 mg/kg/day) given for one week using an implanted Alzet® pump followed by one month observation. We predict that the PIF-analog-treated mice, 0.1 or 1 mg/kg/day for one week, will not develop GVHD, while control mice will develop GVHD.

Model experiment II (FIG. 1). We will examine whether PIF-1 could prevent GVHD development in a higher-burden BMT (double number of spleen cells transplanted than the low-burden BMT). We predict that following exposure to PIF-1 (0.1-1 mg/kg/day) for two weeks, mice will be protected against GVHD.

GVHD Model experiment III (FIG. 3). We will examine whether short-term treatment can lead to long term survival after cessation of therapy. Following high-burden BMT, PIF-analog mg/kg/day for two weeks will be administered and mice will be followed for an additional three and one-half months without therapy. We predict that PIF analog-treated mice will survive in much greater numbers than control mice. We also predict that the PIF analog-treated mice will have significant protection from weight loss.

Example 4: sPIF Analog Treatment in Diabetes Mellitus (DM) (Prophetic)

Materials and methods are the same as Example 2.

DM (adoptive transfer NOD) model. Male NOD mice will be irradiated (650 rad), and injected IV next day with 250 Mil spleen cells collected from female NOD diabetic mice. PIF analogs will be injected in two doses of about 0.83 mg/kg/day (N=5) and 2.73 mg/kg/day (N=7) for 28 days using an Alzet. pump, implanted subcutaneously providing continuous release of the peptide, followed by a 40-day observation period. Animals will be monitored for DM development by determining lasting glucose levels in both blood and urine. Results will be evaluated using ANOVA.

NOD diabetes model. We will examine the effect of PIF-1 in a different autoimmune model, NOD adoptive transfer. In this model, transfer of diabetic splenocytes from female to male mice leads progressively to the development of diabetes mellitus. Exposure to PIF-1 0.83-273 mg/kg/day for the first 28 days had a long-term protective effect against the destruction of pancreatic cells and the consequent high serum glucose levels. We predict that after 70 days, mice treated with PIF will not develop DM while control mice will develop diabetes, possibly in a time frame shorter than 70 days.

To further document PIF analogs immune-modulatory effects, we will use the NOD mouse adoptive transfer model, which results in the development of diabetes (rejected by high glucose levels) due to the destruction of the recipient's pancreas by transfer of autoreactive splenocytes from a diabetic mouse that targets specifically that organ. Using this aggressive model, we predict a long-term protection against DM development using PIF-1 therapy. Such a result would open the possibility of examining young adults that have recently developed DM in whom there has not been a total destruction of insulin-producing pancreas cells. Such an early intervention could lead to a decreased need for insulin administration, or even allow long-term oral anti-diabetic therapy.

Example 5: sPIF Treatment in Multiple Sclerosis (MS) (Prophetic)

Materials and methods are the same as Example 2.

MS EAE model: experimental autoimmune encephalomyelitis, SJL mice 7-8 weeks old will be injected in the tail base with 1:1 of 200 μs proteolytic protein peptide (PLP) together with 200 μg CFA and IFA (containing *Mycobacterium tuberculosis*). On the same day and two days later, mice will be injected IP with 250 ng pertussis toxin. Within nine days, animals typically develop paralysis. PIF analogs will be administered using a subcutaneously implanted Alzet® pump at 0.75 mg/kg/day for 28 days and its effect will be compared to a control group. Daily monitoring of the degree of paralysis (grade 0/no disease . . . 5/dead animal) occurred up to 40 days. PIF-1's protective effects will be calculated using the Mann-Whitney non parametric test.

MS model. We will further examine whether PIF analog therapy could be effective in an additional autoimmune model, experimental autoimmune encephalomyelitis (EAE) in which the majority of the damage occurs in poorly accessible region of the body, the central nervous system. By exposing mice to a combination of a toxic agent (PLP) for the nervous system together with boosting further the inflammatory response with two additional types of bacterial-toxins led to rapid paralysis <10 days The experimental myeloencephalitis, EAE, is recognized as a highly relevant and acute model for MS. The exposure to auto-antigens coupled by induction with two bacterial immunogens leads to progressive paralysis within short term. We predict that treatment with PIF analogs will lead to a significant, reduction in the paralysis score across the observation period which persisted even two weeks after cessation of therapy compared to controls.

MS is believed to be the result of a genetic predisposition followed by a viral insult that leads to CD4+ autoreactive cells followed by differentiation to the $T_{H1}$ phenotype. On the other hand, local damage to central nervous system may occur by CD8+ T cells, and other elements that are involved in the innate immune system. This leads to altered $T_{H2}$ cytokines, regulatory T, and NK cells and IFN-γ secretion.

Example 6: PIF Analog Treatment in Crohn's Disease (Prophetic)

Assess effect of PIF analogs on PBMC isolated from patients with Chron's disease. Established patients PBMC will be isolated and cultured in the presence of PIF analog alone using a dose dependent design and in presence of +/−PHA, or CD3MAb/CD28Mab, used as mitogens, using Cloning media, serum free. After 24 hours of exposure PBMC culture media will be collected and tested for a) cytokine release, both TH1 and TH2, using the Luminex 10 package b) PIF receptor expression exposing to FITC-PIF and labeled-CD14, CD4, CD8, or CD58, or CD19MAb followed by flow cytometry) c) in selective cases, mRNA will be extracted and using an Affymetrix chip global genome analysis will be carried out. Results will be compared with PBMC similarly treated derived from normal volunteers.

Assess effect of PIF analogs on colon biopsy of patients with Crohn's disease. In parallel, to obtaining PBMC also biopsies from the same patients will be obtained during colonoscopy. Biopsy samples will be placed in culture to generate explants using RPM11640 medium. Explant cultures will be carried out for 24 hours in the presence of PIF 0-200 nM. Subsequently the media will be collected and analyzed for cytokines using the 10 multiplex Luminex system (TH1 and TH2). The tissue itself will be placed in formalin and will be analyzed for cytokine content using IHC, as well as immune cell type presence using flow cytometry and specific CD markers.

Example 7 Treatment of *Mycobacterium tuberculosis* (Mtb) (Prophetic)

Cultured bone marrow derived phagocytes will be exposed to PIF analogs (SEQ ID NO. 1 through 10 in therapeutically effective concentrations with and without interferon-gamma (phagocyte-activating cytokine). To assess efficacy in treating Mtb the cytokine response in the presence or absence of Kv1.3, a potassium channel inhibitor. MCP-1 (a chemokine) interleukin (IL-)-6 and IL-5 are expected to be increased by Mtb; this induction will be expected to be augmented by PIF analogs and blocked by Kv1.3 inhibition. Modest augmentation of MIG and IP-10 chemokines when IFN activated phagocytes were exposed to Mtb will be measured in the presence and absence of PIF analogs. Inhibition of Kv1.3 will also be measured. PIF will induce VEGF and FGFp upregulation by Mtb (regardless of phagocyte activation by IFNy) and inhibition of Kv1.3 will augment this response. Levels of inflammatory cytokines TNF, IL-la, IL-Iβ, MlPlα and KC will be measured after inducion by Mtb, in the presence and absence of PIF analogs. it is expected that PIF analog-conditioned macrophages will exhibit an altered response to Mtb. If PIF analogs modulate the phagocyte response to Mtb and may therefore modulate disease development Example 8 PIF Analogs Control MTb-Infected Macrophages In vitro studies will use mouse bone marrow derived dendritic cells (BMDCs) and such cells will be exposed to Mtb+/−PIF analogs for 24 hrs in culture. Modulation of the phagocyte response to Mtb at low (nM) physiological PIF analog concentrations will be monitored. Pre-treatment with sPIF resulted in BMDCs augmented response to Mtb specifically: inflammatory cytokines TNF, IL-la, IL-lb and IL-6 and chemokines MCP-1 MlPla and KC were increased. Importantly, PIF analogs will be tested to observe whether there is an increase the response of BMDC even in absence of pre-activation by interferon-γ. VEGF and FGFb (growth factors) levels will also be tested by PIF analogs, where increased levels of the growth factors suggest PIF analog capability to modulate the remodeling activity of BMDCs. Hence, PIF analogs may exert a potent anti-mycobacterial response that is evidenced both in absence and presence of acquired immunity as represented by interferon-γ pre-treatment.

Whether binding to Kv1.3b is also relevant in the BMDC context will be demonstrated by using an anti-Kv1.3 inhibitor. A number of PIF analogs will be tested by measuring induced cytokine and chemokine secretion patterns in the presence of the inhibitor. Collectively the in vitro and in vivo data (BMDC Mtb data) will support PIF analog efficacy to control Mtb infection.

Example 9 PIF Analogs Treat Atherosclerosis

To demonstrate the therapeutic potential of PIF analogs in treating atherosclerosis, male ApoE−/− mice will be fed a high fat Western diet containing 22% fat and 0.15% cholesterol for 7 weeks. Mice will then be randomly assigned to one of six clusters; 3 intervention groups of varied PIF doses, and 3 control groups of scrambled PIF negative control or PBS. Treatments will be administered via 150 μE i.p. injection every 3rd day, for a total of 7 weeks.

PIF (0.1 mg/kg/day treatment) will significantly reduce the plaque area in the aortic root by about 30% as compared to the PBS control (D, p=0.0008). A greater reduction of 46% plaque area will in PIF (1 mg/kg/day) compared to PBS (D, p<0.0001). The higher dose of PIF also statistically significantly reduced plaque area compared to both doses of scrPIF (p<0.0001). PIF 1 mg/kg/day treatment significantly reduced the plaque area of the aortic arch by 43% compared to the PBS control (E, p<0.002). A reduction result will indicate that was again also efficacy of the PIF analogs with the statistic analysis (*p=0.0005 or **p<0.0001) Reduction of VCAM-1, MCP-1, CD68 and lipi levels will be measured in the aortic root and arch.

In conclusion, PIF analogs will reduce atherosclerosis formation in a mouse model that is prone to the disease and is fed a high fat diet. The protection will be direct and lead to reduced atherosclerotic plaques on both the aortic arch and root-target sites in PIF analogs behave in a similar fashion to wild-type PIF. A decrease in fat accumulation will be measured in the animals, as well as a decrease in inflammatory macrophages and a lower number of fat foam cells. The protective effect will not be related to changes in circulating lipids, if, after measuring the lipid levels did not change following PIF analog administration.

Example 10 PIF Analog Treatment of Peritonitis

To demonstrate that PIF inhibits MCP-1 induced monocyte migration, a mouse peritonitis model study will be conducted. In this model, 8-12 weeks old C57bl6 mice will be injected with either PIF analog, srambled PIF sequence negative control (0.3 nmol/g i.p.) or PBS as a vehicle control. Peritonitis will be induced by injecting 3 ml 4% thioglycolate i.p. and after 20 hours, the mice will be anaesthetized and the peritoneal cavity will be flushed with 5 ml sterile PBS. Subsequently, monocytes and macrophages were quantified with F4/80 and CD1 lb in flow cytometry.

As shown in FIG. 6, the results may show that PIF (1 μM & 10 μM) significantly reduces MCP-1 induced transmigration of THP-1 cells in an in vitro transwell migration assay (*p<0.01). PIF further inhibited leukocyte adhesion and rolling in mesenteric venules in intravital microscopy using the peritonitis model as described in and cell staining with rhodamine.

Example 11

Healthy pregnancy requires coordination of several soluble factors acting individually or in synergy with each other. Examples of those soluble factors include HLA-G, cytokines, and progesterone. The soluble factors are secreted during infection, which affects fetal development and often causes complications which may result in abortive pregnancy. PIF analogs may exert an autocrine trophic protective effect on the embryo and promotes embryo implantation and trophoblast invasion similar to wild-type PIF. A determination will be made as to whether PIFanalogs affect LPS-induced nitrous oxide (NO) secretion by macrophages and how PIF analogs may limit macrophage responses to LPS, which is the major endotoxin of gram negative bacteria.

A macrophage cell line will be cultured with 200 nM PIF (synthetic PIF analog) for 2 and 5 days. In the last 24 hours of the experiment, LPS will be added to the culture for cell activation. A Greiss reagent test was performed to detect NO secretion to the supernatant. Surface Plasmon Resonance spectroscopy (SPR) will be used to evaluate LPS and LPS receptors binding (TLR4-MD2 and CD 14) to the PIF analog-labeled sensor surface. Two chemotypes of LPS (From $E.\ coli$ 055:B5 and $E.\ coli$ EH100) at least 3 concentrations (5, 25 and 100 μM) will be tested.

If PIF analogs significantly down-regulated NO production following LPS activation the effect at 2 days will be more pronounced than at 5 days (P<0.05). Preliminary results indicated an apparent absence of binding of immobilized native or wild-type PIF to both LPS chemotypes tested; similarly, no binding was observed to the scrambled PIF sequence negative control used as the control (random peptide of same amino acid in random order). To ascertain PIF's structural integrity, a PIF-specific antibody will be incubated with purified PIF analogs and results showed that the antibody bound to PIF analogs. Under the conditions set up for the SPR analysis, PIF analogs may not exhibit no apparent LPS binding.

In conclusion, PIF analogs may block NO secretion, a major LPS-induced reactive nitrogen intermediate produced by iNOS, which is an enzyme absent in resting macrophages. PIF does not bind directly LPS, but its action might involve binding to LPS-associated receptors such as CD14, MD2 and macrophage scavenger receptor (SR). Such data supports a targeted anti-inflammatory effect of PIF analogs on the innate immune system.

Although the present invention has been described in considerable detail with reference to certain preferred embodiments thereof, other versions are possible. Therefore the spirit and scope of the appended claims should not be limited to the description and the preferred versions contain within this specification. Any patent applications or other journal articles disclosed herein are incorporated by reference in their entireties.

REFERENCES

1. Schoenfeld, A. J., M. D. Laughlin, B. J. McCriskin, J. O. Bader, B. R. Waterman, and P. J. Belmont, Jr., Spinal injuries in United States military personnel deployed to Iraq and Afghanistan: an epidemiological investigation involving 7877 combat casualties from 2005 to 2009. Spine (Phila Pa. 1976), 2013. 38(20): p. 1770-8.
2. Bell, R. S., A. H. Vo, C. J. Neal, J. Tigno, R. Roberts, C. Mossop, J. R. Dunne, and R. A. Armonda, Military traumatic brain and spinal column injury: a 5-year study of the impact blast and other military grade weaponry on the central nervous system. J Trauma, 2009. 66(4 Suppl): p. S104-11.
3. Barnea, E. R., Insight into early pregnancy events: the emerging role of the embryo. Am J Reprod Immunol, 2004. 51(5): p. 319-22.
4. Stamatkin, C. W., R. G. Roussev, M. Stout, C. B. Coulam, E. Triche, R. A. Godke, and E. R. Barnea, Preimplantation factor negates embryo toxicity and promotes embryo development in culture. Reprod Biomed Online, 2011. 23(4): p. 517-24.
5. Stamatkin, C. W., R. G. Roussev, M. Stout, V. Absalon-Medina, S. Ramu, C. Goodman, C. B. Coulam, R. O. Gilbert, R. A. Godke, and E. R. Barnea, Preimplantation Factor (PIF) correlates with early mammalian embryo development-bovine and murine models. Reprod Biol Endocrinol, 2011. 9: p. 63.
6. Barnea, E. R., Applying embryo-derived immune tolerance to the treatment of immune disorders. Ann N Y Acad Sci, 2007. 1110: p. 602-18.
7. Weiss, L., S. Bernstein, R. Jones, R. Amunugama, D. Krizman, L. Jebailey, O. Almogi-Hazan, Z. Yekhtin, R. Shiner, I. Reibstein, E. Triche, S. Slavin, R. Or, and E. R. Barnea, Preimplantation factor (PIF) analog prevents type I diabetes mellitus (TIDM) development by preserving pancreatic function in NOD mice. Endocrine, 2011. 40(1): p. 41-54.
8. Weiss, L., R. Or, R. C. Jones, R. Amunugama, L. JeBailey, S. Ramu, S. A. Bernstein, Z. Yekhtin, O. Almogi-Hazan, R. Shainer, I. Reibstein, A. O. Vortmeyer, M. J. Paidas, M. Zeira, S. Slavin, and E. R. Barnea, Preimplantation factor (PIF*) reverses neuroinflammation while promoting neural repair in EAE model. J Neurol Sci, 2012. 312(1-2): p. 146-57.
9. Azar, Y., R. Shainer, O. Almogi-Hazan, R. Bringer, S. R. Compton, M. J. Paidas, E. R. Barnea, and R. Or, Preimplantation Factor Reduces Graft-versus-Host Disease by Regulating Immune Response and Lowering Oxidative Stress (Murine Model). Biology of Blood and Marrow Transplantation, 2013. 19: p. 519-528.
10. Shainer, R., Y. Azar, O. Almogi-Hazan, R. Bringer, S. R. Compton, M. J. Paidas, E. R. Barnea, and R. Or, Immune Regulation and Oxidative Stress Reduction by Preimplantation Factor following Syngeneic or Allogeneic Bone Marrow Transplantation. Conference Papers in Medicine, 2013. 2013 (Article ID 718031): p. 1-8.
11. Mueller, M., J. Zhou, L. Yang, Y. Gao, F. Wu, A. Schoeberlein, D. Surbek, E. R. Barnea, M. Paidas, and Y. Huang, Preimplantation factor promotes neuroprotection by targeting microRNA let-7. Proc Natl Acad Sci USA, 2014. 111(38): p. 13882-7.
12. Mueller, M., A. Schoeberlein, A. Zhou, M. Joerger-Messerli, B. Oppliger, U. Reinhart, A. Bordey, D. Surbek, E. R. Barnea, Y. Huang, and M. Paidas, Preimplantation Factor Bolsters Neuroprotection via Modulating Q10 Protein Kinase A and Protein Kinase C Signaling. Cell Death Differ, 2015. DOI: 10.1038/cdd.2015.55.
13. Chen, Y. C., J. Rivera, M. Fitzgerald, C. Hausding, X. Wang, K. Todorova, S. Hayrabedyan, E. R. Barnea, and P. Karlheinz, Preimplantation Factor Prevents Atherosclerosis via it Anti-inflammatory Effects without Affecting Serum Lipids. 2015. (submitted).
14. Migliara, G., M. Mueller, M. J. Paidas, E. R. Barnea, and F. Ria, PIF Ameliorates Clinically Relevant B. *Smegmatis* Induced Brain Infection by Reducing Oxidative Stress and Protein Misfolding. 2015. (submitted).
15. Barnea, E. R., J. Simon, S. P. Levine, C. B. Coulam, G. S. Taliadouros, and P. C. Leavis, Progress in characterization of pre-implantation factor in embryo cultures and in vivo. Am J Reprod Immunol, 1999. 42(2): p. 95-9.
16. Barnea, E. R., Applying Embryo-Derived Immune Tolerance to the Treatment of Immune Disorders. Annals of the New York Academy of Sciences, 2007. 1110: p. 602-618.
17. Than, N. G., M. J. Paidas, S. Mizutani, S. Sharma, J. Padbury, and E. R. Barnea, Embryo-placento-maternal interaction and biomarkers: from diagnosis to therapy—a workshop report. Placenta, 2007. 28 Suppl A: p. S107-10.
18. Barnea, E. R., D. Kirk, S. Ramu, B. Rivnay, R. Roussev, and M. J. Paidas, PreImplantation Factor (PIF) orchestrates systemic antiinflammatory response by immune cells: effect on peripheral blood mononuclear cells. Am J Obstet Gynecol, 2012. 207(4): p. 313 el-11.
19. Moindjie, H., E. D. Santos, L. Loeuillet, H. Gronier, P. de Mazancourt, E. R. Barnea, F. Vialard, and M. N. Dieudonne, Preimplantation factor (PIF) promotes human trophoblast invasion. Biol Reprod, 2014. 91(5): p. 118.
20. Paidas, M. J., G. Krikun, S. J. Huang, R. Jones, M. Romano, J. Annunziato, and E. R. Barnea, A genomic and proteomic investigation of the impact of preimplantation factor on human decidual cells. Am J Obstet Gynecol, 2010. 202(5): p. 459 el-8.
21. Duzyj, C. M., E. R. Barnea, M. Li, S. J. Huang, G. Krikun, and M. J. Paidas, Preimplantation factor promotes first trimester trophoblast invasion. Am J Obstet Gynecol, 2010. 203(4): p. 402 el-4.
22. Duzyj, C. M., M. J. Paidas, L. Jebailey, J. S. Huang, and E. R. Barnea, PreImplantation Factor (PIF*) promotes embryotrophic and neuroprotective decidual genes: effect negated by epidermal growth factor. Journal of Neurodevelopmental Disorders, 2014. 6(1): p. 36.
23. Shainer, R., Z. Yekhtin, L. Weiss, O. Almogi-Hazan, M. Mueller, M. J. Paidas, R. Or, and E. R. Barnea, Episodic PreImplantation Factor (PIF*) Administration Reverses Chronic Paralysis by Reducing Brain PKA/PKC Phosphorylation 2015. (in preparation).
24. Roussev, R. G., B. V. Dons'koi, C. Stamatkin, S. Ramu, V. P. Chernyshov, C. B. Coulam, and E. R. Barnea, Preimplantation factor inhibits circulating natural killer cell cytotoxicity and reduces CD69 expression: implications for recurrent pregnancy loss therapy. Reprod Biomed Online, 2013. 26(1): p. 79-87.
25. Barnea, E. R., D. Kirk, K. Todorova, J. McElhinney, S. Hayrabedyan, and N. Fernandez, PIF direct immune regulation: Blocks mitogen-activated PBMCs proliferation, promotes T2/T1 bias, independent of Ca. Immunobiology, 2015. DOI:10.1016/j.imbio.2015.01.010.
26. Barnea, E. R., D. M. Lubman, Y. H. Liu, V. Absalon-Medina, S. Hayrabedyan, K. Todorova, R. O. Gilbert, J. Guingab, and T. J. Barder, Insight into Preimplantation Factor (PIF*) mechanism for embryo protection and development: target oxidative stress and protein misfolding (PDI and HSP) through essential RIPK binding site. PLoS One, 2014. 9(7): p. e100263.
27. Almogi-Hazan, O., R. Shainer, E. R. Barnea, and R. Or, The Role of Nitric Oxide Toxicity and Oxidative Stress in Graft vs Host Disease, in Oxidative Stress: Causes, Role in Diseases and Biological Effects. 2014, Nova Science Publishers, Inc.
28. Barnea, E. R., S. Hayrabedyan, K. Todorova, O. Almogi-Hazan, R. Or, J. Guingab, J. McElhinney, N. Fernandez, and T. J. Barder, PIF Regulates Systemic Immunity and Targets Protective Regulatory and Cytoskeleton Proteins. Scientific Reports, Nature, 2015. (under revision).
29. Kuluz, J., A. Samdani, D. Benglis, M. Gonzalez-Brito, J. P. Solano, M. A. Ramirez, A. Luqman, R. De los Santos, D. Hutchinson, M. Nares, K. Padgett, D. He, T. Huang, A. Levi, R. Betz, and D. Dietrich, Pediatric spinal cord injury in infant piglets: description of a new large animal model and review of the literature. J Spinal Cord Med, 2010. 33(1): p. 43-57.
30. Cheriyan, T., D. J. Ryan, J. H. Weinreb, J. Cheriyan, J. C. Paul, V. Lafage, T. Kirsch, and T. J. Errico, Spinal cord injury models: a review. Spinal Cord, 2014. 52(8): p. 588-95.
31. Abou-Donia, M. B., M. M. Abou-Donia, E. M. ElMasry, J. A. Monro, and M. F. Mulder, Autoantibodies to nervous system-specific proteins are elevated in sera of flight crew members: biomarkers for nervous system injury. J Toxicol Environ Health A, 2013. 76(6): p. 363-80.

LIST OF ABBREVIATIONS USED FOR THE PURPOSE OF THE PATENT DISCLOSURE

BPD Bronchopulmonary Dysplasia
FDA Food & Drug Administration
NK Natural Killer
OEF Operation Enduring Freedom
OIF Operation Iraqi Freedom
OND Operation New Dawn
PBS Phosphate buffered saline
PIF Preimplantation Factor
sPIF Synthetic Preimplantation Factor
SC Spinal Cord
SCI Spinal Cord Injury
TI Traumatic Injury

The invention claimed is:

1. A composition comprising a pre-implantation factor (PIF) analog, wherein the PIF analog comprises an amino acid sequence, wherein:
   (a) the amino acid sequence is at least 93% identical to the amino acid sequence of SEQ ID NO: 7, SEQ ID NO: 8, or SEQ ID NO: 9; or
   (b) the amino acid sequence selected from the group consisting of SEQ ID NO: 1, SEQ ID NO: 2, SEQ ID NO: 3, SEQ ID NO: 4, SEQ ID NO: 5, and SEQ ID NO: 6, or a pharmaceutically acceptable salt thereof, and
   wherein the composition is free of a peptide comprising or consisting of the amino acid sequence of SEQ ID NO: 11.

2. The composition of claim 1, wherein the PIF analog comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9, or a pharmaceutically acceptable salt thereof.

3. A pharmaceutical composition comprising:
   i) a therapeutically effective amount of the composition of claim 1; and
   ii) a pharmaceutically acceptable carrier.

4. The pharmaceutical composition of claim 3, wherein the PIF analog comprises the amino acid sequence that is at least 93% identical to the amino acid sequence of SEQ ID NO: 8 or SEQ ID NO: 9, or a pharmaceutically acceptable salt thereof.

5. The pharmaceutical composition of claim 3, wherein the therapeutically effective amount is from about 1 milligram to about 4 grams.

6. The pharmaceutical composition of claim 3, wherein the therapeutically effective amount is about 70 milligrams.

7. A method of treating autoimmune disease in a subject in need thereof, wherein the method comprises administering to the subject a pharmaceutical composition comprising:
   i) a therapeutically effective amount of at least one PIF analog, wherein the PIF analog comprises an amino acid sequence, wherein:
      (a) the amino acid sequence is at least 93% identical to the amino acid sequence of SEQ ID NO: 7, SEQ ID NO: 8, or SEQ ID NO: 9; or
      (b) the amino acid sequence is selected from the group consisting of SEQ ID NO: 1, SEQ ID NO: 2, SEQ ID NO: 3, SEQ ID NO: 4, SEQ ID NO: 5, and SEQ ID NO: 6,
   or a pharmaceutically acceptable salt thereof; and
   ii) a pharmaceutically acceptable carrier;
   wherein the pharmaceutical composition is free of a peptide comprising or consisting of the amino acid sequence of SEQ ID NO: 11,
   and wherein the autoimmune disease is graft-versus-host disease, type 1 diabetes, or multiple sclerosis.

8. The method of claim 7, wherein the pharmaceutically acceptable carrier is sterile and pyrogen-free water or sterile and pyrogen-free Lactated ringer's solution.

9. The method of claim 7, wherein the therapeutically effective amount is from about 0.1 mg/kg to about 1.0 mg/kg.

10. The method of claim 7, wherein the therapeutically effective amount is from about 0.1 mg/kg to about 5.0 mg/kg.

11. The method of claim 7, wherein the PIF analog is at least one of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9, or a pharmaceutically acceptable salt thereof.

12. The method of claim 7, wherein the step of administering to the subject the pharmaceutical composition comprises administering a therapeutically effective amount of the PIF analog or pharmaceutically acceptable salt thereof from about 0.001 mg/kg to about 200 mg/kg.

13. The method of claim 7, wherein the step of administering to the subject the pharmaceutical composition comprises administering a therapeutically effective amount of the PIF analog or pharmaceutically acceptable salt thereof from about 0.5 mg/kg to about 5 mg/kg.

14. The method of claim 7, wherein the autoimmune disease is multiple sclerosis.

15. The method of claim 7, wherein the autoimmune disease is type 1 diabetes.

16. The method of claim 7, wherein the autoimmune disease is graft-versus-host disease.

17. A method of treating diabetes in a subject in need thereof, wherein the method comprises administering to the subject a pharmaceutical composition comprising:
   i) a therapeutically effective amount of at least one PIF analog, wherein the PIF analog comprises an amino acid sequence, wherein:
      (a) the amino acid sequence is at least 93% identical to the amino acid sequence of SEQ ID NO: 7, SEQ ID NO: 8, or SEQ ID NO: 9; or (b) the amino acid sequence is selected from the group consisting of SEQ ID NO: 1, SEQ ID NO: 2, SEQ ID NO: 3, SEQ ID NO: 4, SEQ ID NO: 5, and SEQ ID NO: 6, or a pharmaceutically acceptable salt thereof; and ii) a pharmaceutically acceptable carrier;

and wherein the pharmaceutical composition is free of a peptide comprising or consisting of the amino acid sequence of SEQ ID NO: 11.

18. The method of claim 17, wherein the pharmaceutically acceptable carrier is sterile and pyrogen-free water or sterile and pyrogen-free Lactated ringer's solution.

19. The method of claim 17, wherein the therapeutically effective amount is from about 0.1 mg/kg to about 1.0 mg/kg.

20. The method of claim 17, wherein the therapeutically effective amount is from about 0.1 mg/kg to about 5.0 mg/kg.

21. The method of claim 17, wherein the PIF analog is at least one of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9, or a pharmaceutically acceptable salt thereof.

22. The method of claim 17, wherein the pharmaceutical composition is administered intravenously, intramuscularly, topically, intradermally, transmucosally, subcutaneously, sublingually, transdermally, orally, buccally, intraocularly, intravaginally, intrarectally, intraductally, intrathecally, subdurally, extradurally, intraventricularly, intraarticularly, intraperitoneally; into the pleural cavity; by inhalation; by depot injections; or by implants.

23. A method of binding an insulin degrading enzyme (IDE) in a subject in need thereof, wherein the method comprises administering to the subject a pharmaceutical composition comprising:

i) a therapeutically effective amount of at least one pre-implantation factor (PIF) analog, wherein the PIF analog comprises an amino acid sequence, wherein:

(a) the amino acid sequence is at least 93% identical to the amino acid sequence of SEQ ID NO: 7, SEQ ID NO: 8, or SEQ ID NO: 9; or (b) the amino acid sequence is selected from the group consisting of SEQ ID NO: 1, SEQ ID NO: 2, SEQ ID NO: 3, SEQ ID NO: 4, SEQ ID NO: 5, and SEQ ID NO: 6, or a pharmaceutically acceptable salt thereof; and ii) a pharmaceutically acceptable carrier;

wherein the pharmaceutical composition is free of a peptide comprising or consisting of the amino acid sequence of SEQ ID NO: 11.

24. The method of claim 23, wherein the PIF analog is at least one of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9, or a pharmaceutically acceptable salt thereof.

* * * * *